(12) United States Patent
Oishi

(10) Patent No.: US 7,909,946 B2
(45) Date of Patent: Mar. 22, 2011

(54) COPPER ALLOY

(75) Inventor: Keiichiro Oishi, Yao (JP)

(73) Assignee: Mitsubishi Shindoh Co., Ltd., Tokyo (JP)

( * ) Notice: Subject to any disclaimer, the term of this patent is extended or adjusted under 35 U.S.C. 154(b) by 54 days.

(21) Appl. No.: 10/597,454

(22) PCT Filed: Aug. 10, 2005

(86) PCT No.: PCT/JP2005/014691
§ 371 (c)(1),
(2), (4) Date: Jan. 30, 2007

(87) PCT Pub. No.: WO2006/016624
PCT Pub. Date: Feb. 16, 2006

(65) Prior Publication Data
US 2007/0169855 A1    Jul. 26, 2007

(30) Foreign Application Priority Data
Aug. 10, 2004   (JP) ................ 2004-233952

(51) Int. Cl.
C22C 9/04   (2006.01)
(52) U.S. Cl. ..................................... 148/434
(58) Field of Classification Search .............. None
See application file for complete search history.

(56) References Cited

U.S. PATENT DOCUMENTS

| | | | | |
|---|---|---|---|---|
| 4,047,978 A * | 9/1977 | Parikh et al. | | 148/684 |
| 4,055,445 A | 10/1977 | Pops | | |
| 4,110,132 A * | 8/1978 | Parikh et al. | | 148/434 |
| 4,515,204 A * | 5/1985 | Ohno | | 164/483 |
| 4,710,349 A * | 12/1987 | Yamazaki et al. | | 420/495 |
| 4,770,718 A * | 9/1988 | Verhoeven et al. | | 75/247 |
| 4,826,736 A | 5/1989 | Nakamura et al. | | |
| 5,288,458 A * | 2/1994 | McDevitt et al. | | 420/477 |
| 2002/0069942 A1 | 6/2002 | Oishi | | |
| 2002/0159912 A1* | 10/2002 | Oishi | | 420/477 |

FOREIGN PATENT DOCUMENTS

| | | |
|---|---|---|
| JP | 38-20487 | 4/1963 |
| JP | 49-40226 | 4/1974 |
| JP | 58-037143 A | 3/1983 |
| JP | 59-136439 A | 8/1984 |
| JP | 61048547 | 3/1986 |
| JP | 02-170954 A | 7/1990 |
| JP | 04-224645 A | 8/1992 |
| JP | 10-152735 | 6/1998 |
| JP | 2004-100041 A | 4/2004 |

OTHER PUBLICATIONS

International Search Report, Issued in the Corresponding Application PCT/JP2005/014691, Completed Oct. 28, 2005 and Mailed Nov. 15, 2005.
F.A. Fasoyinu, Effects of Grain Refinement of Hot Tear Resistance and Shrinkage Characteristics of Permanent Mold Cast Yellow Brass (C85800), pp. 327-337.
M. Sadayappan, Fading of Grain Refinement in Permanent Mold Cast Copper Alloys, AFS Transactions 2004 © American Foundry Society, Des Plaines IL USA, pp. 521-526.
Prof. Dr.-Ing. W. Reif, A New Grain Refiner for Copper-Zinc Alloys containing 25-42%Zinc, Metall 41. Jahrgang Heft Nov. 11, 1987, pp. 1131-1137.
M. Sadayappan, GrainRefinement of Copper Base Alloys, vol. 1-Plenary Lectures/Movement of Copper and Industry Outlook/Copper Applications and Fabrication, 1999, pp. 279-291.
M. Sadayappan, Grain Refinement of Permanent Mold Cast Silicon Brass, Silicon Bronze and Red Brass, AFS Transactions, pp. 337-342.
A. Couture, Grain Refinement of Sand Cast Bronzes and its Influence on Their Properties, AFS Cast Metals Research Journal, Mar. 1974, pp. 1-5.
M. Sadayappan, Grain Refinement Studies on Leaded and Bi/Se Modified Yellow Brasses, pp. 45-58.
M. Sahoo, An Overview of ICA-Funded Research and Development at MTL/Canmet, pp. 1-12.
European Office Action issued in corresponding application No. EP 05 770 520.4, mailed May 18, 2009.
F. Romankiewicz et al. "Kornfeinung von kupferlegierungen," Metallwissenschaft und Technik, 48. Jahrgang, Nr. Nov. 1994, pp. 865-871, XP9115894.
Restricton/Election Office Action issued in related co-pending U.S. Appl. No. 10/597,233, dated Aug. 18, 2009.
Office Action issued in co-pending related U.S. Appl. No. 10/596,849, mailed Oct. 16, 2009.
Metal Handbook Ninth Edition, vol. 9, Metallography and Microstructures, pp. 629-631, filed herewith as Exhibit A.
Metal Handbook Ninth Edition, vol. 9, Metallography and Microstructures (American Society for Metals), pp. 641-642, filed herewith as Exhibit B.
pp. 290 & C-2 of Metal Handbook 8th Edition, vol. 7, Atlas of Microstructures of Industrial Alloys (American Society for Metals), filed herewith as Exhibit C. pp. 286 of Metal Handbook 8th Edition, vol. 7, Atlas of Microstructures of Industrial Alloys (American Society for Metals), filed herewith as Exhibit D.
U.S. Patent 4,055,445 to Pops, issued Oct. 25, 1977, filed herewith as Exhibit E.
Office Action dated Feb. 23, 2010 in co-pending related U.S. Appl. No. 10/597,233, filed Jul. 17, 2006.
Office Action issued in co-pending related U.S. Appl. No. 10/597,233, mailed Oct. 1, 2010.

* cited by examiner

*Primary Examiner* — Melvin C Mayes
*Assistant Examiner* — Stefanie Cohen
(74) *Attorney, Agent, or Firm* — Griffin & Szipl, P.C.

(57) ABSTRACT

A copper alloy consists essentially of Cu: 69 to 88 mass %, Si: 2 to 5 mass %, Zr: 0.0005 to 0.04 mass %, P: 0.01 to 0.25 mass %, and Zn: balance; has relation of, in terms of content of element a, [a] mass %, f0=[Cu]−3.5[Si]−3[P]=61 to 71, f1=[P]/[Zr]=0.7 to 200, f2=[Si]/[Zr]=75 to 5000, and f3=[Si]/[P]=12 to 240; has a metal structure containing α phase and, κ phase and/or γ phase, and has relation of, in terms of a content of phase b, [b]%, in an area rate, f4=[α]+[γ]+[κ]≧85 and f5=[γ]+[κ]+0.3[μ]−[β]=5 to 95; and has an average grain diameter of 200 μm or less in a macrostructure when melted and solidified.

140 Claims, 7 Drawing Sheets (A)

(B)

(A)

(B)

COPPER ALLOY

This is a National Phase Application in the United States of International Patent Application No. PCT/JP2005/14691 filed Aug. 10, 2005, which claims priority on Japanese Patent Application No. 2004-233952, filed Aug. 10, 2004. The entire disclosures of the above patent applications are hereby incorporated by reference.

BACKGROUND OF THE INVENTION

1. Field of the Invention

The present invention relates to a Cu—Zn—Si based alloy having excellent castability, mechanical properties (strength, ductility etc.), corrosion resistance, wear resistance, machinability and the like.

2. Description of the Related Art

It has been known that copper alloys are improved in yield strength by grain refinement like ordinary metal materials, and that in accordance with the Hall-Petch law the copper alloys are improved in strength in proportion to the inverse of the square root of the grain diameter.

And the copper alloys are generally subjected to two basic types of grain refinement as follows: (A) when the copper alloys are melted and solidified, (B) when the copper alloys (ingots such as slabs, castings such as die castings, melted castings etc.) after melt-solidification are subjected to either deforming such as rolling or heating, and the resultant stored energy such as distorted energy acts as a driving force. In either case of (A) or (B), Zirconium (Zr) is known as an element that effectively affects the grain refinement.

However, in the case of (A), since the grain refinement effect of Zr in the step of melt-solidification is considerably influenced by other elements and their contents, a desired level of grain refinement is not achieved. For this reason, generally, the technique of (B) has been widely used, wherein the grain refinement is facilitated by performing heat treatment on the ingots, castings and so forth after melt-solidification, and then endowing distortion again.

According to teachings of Japanese Examined Patent Application Publication No. 38-20467, a copper alloy containing Zr, P and Ni is subjected to melting treatment, cold working at a rate of 75%, and examination of its average grain diameter, in which the average grain diameter is decreased in proportion to increase of a content of Zr, for example, 280 μm when not containing Zr, 170 μm (Zr content: 0.05 mass %), 50 μm (Zr content: 0.13 mass %), 29 μm (Zr content: 0.22 mass %) and 6 μm (Zr content: 0.89 mass %). In this document, it is proposed to contain 0.05 to 0.3 mass % Zr in order to avoid an adverse effect caused by excessive content of Zr.

Further, it is disclosed in Japanese Unexamined Patent Application Publication No. 2004-100041 that when a copper alloy to which 0.15 to 0.5 mass % Zr is added is subjected to casting, melting treatment, and deformation processing for distortion addition, its average grain diameter is refined to a level of about 20 μm or less.

However, as in the technique of (B), these treatment and working after casting for refining the grain diameter result in increased costs. Further, some castings can not be subjected to the deformation processing for distortion addition due to their shapes. As such, the grains are preferably refined by the technique of (A) when the copper alloy is melted and solidified. However, in the case of the technique of (A), as set forth above, Zr is greatly influenced by other elements and their contents in the step of melt-solidification. Hence, although the content of Zr is increased, the grain refinement corresponding to the increase is not necessarily achieved. Further, Zr has very strong affinity for oxygen. Accordingly, when being melted and added in the atmosphere, Zr easily forms an oxide and is very low in yield. As such, although a very small quantity of Zr is contained in products after casting, it is required to charge a considerable quantity of raw material in the step of casting. Meanwhile, when being too much produced during melting, the oxide is easily entangled when casting, there is a chance to generate casting defects. In order to avoid production of the oxide, the melting and casting may be carried out under a vacuum or inert gas atmosphere, which causes increase of costs. In addition, because Zr is an expensive element, its addition amount is preferably restrained to be as small as possible from the economic point of view.

For this reason, there is required a copper alloy having the content of Zr as small as possible and simultaneously the average grain diameter refined in the following step after melt-solidification of the casting process.

Further, in the case of the Cu—Zn—Si based alloy, Si serves to improve mechanical property etc., but during melt-solidification, has problems that it is easy to generate a crack or porosity, that a shrinkage cavity is great, and that it is easy to generate casting defects such as a blow hole. The main reason is because as a content of Si increases, a solidification temperature range (a difference between a liquidus temperature and a solidus temperature) becomes wide, and a thermal conductivity is also deteriorated. Further, taking a view of a solidification structure of a conventional Cu—Zn—Si based alloy, a dendrite is generated in a tree-like branching pattern. Arms of the dendrite make it difficult to discharge generated air bubbles into the air, which is responsible for residual of blow holes, and local generation of great shrinkage cavity.

The present invention provides a Cu—Zn—Si based alloy capable of significantly improving copper alloy properties such as castability, various mechanical properties, corrosion resistance, machinability, workability etc. by means of refinement of grains, and simultaneously a method of fabricating the same.

SUMMARY OF THE INVENTION

In order to accomplish the objective, the present invention proposes a copper alloy and method of fabricating the same as follows:

First, the present invention proposes a copper alloy (hereinafter, referred to as a "first copper alloy") consisting essentially of Cu: 69 to 88 mass % (preferably 70 to 84 mass %, more preferably 71.5 to 79.5 mass %, and most preferably 73 to 79 mass %), Si: 2 to 5 mass % (preferably 2.2 to 4.8 mass %, more preferably 2.5 to 4.5 mass %, and most preferably 2.7 to 3.7 mass %), Zr: 0.0005 to 0.04 mass % (preferably 0.0008 to 0.029 mass %, more preferably 0.001 to 0.019 mass %, still more preferably 0.0025 to 0.014 mass %, and most preferably 0.004 to 0.0095 mass %), P: 0.01 to 0.25 mass % (preferably 0.02 to 0.2 mass %, more preferably 0.03 to 0.16 mass %, and most preferably 0.04 to 0.12 mass %), Zn: balance, and meeting the following conditions of (1) to (7). In the first copper alloy, it is preferable to additionally meet the following conditions of (10) to (15), inclusive of the conditions of (1) to (7). When the first copper alloy requires cutting, it is preferable to additionally meet a condition of (17), inclusive of the conditions of (1) to (7) and (10) to (15).

Secondly, the present invention proposes a copper alloy (hereinafter, referred to as a "second copper alloy"), containing at least one element from Sn, As and Sb in addition to the constituent elements of the first copper alloy, that is, consisting essentially of Cu: 69 to 88 mass % (preferably 70 to 84 mass %, more preferably 71.5 to 79.5 mass %, and most preferably 73 to 79 mass %); Si: 2 to 5 mass % (preferably 2.2 to 4.8 mass %, more preferably 2.5 to 4.5 mass %, and most preferably 2.7 to 3.7 mass %); Zr: 0.0005 to 0.04 mass % (preferably 0.0008 to 0.029 mass %, more preferably 0.001 to 0.019 mass %, still more preferably 0.0025 to 0.014 mass %, and most preferably 0.004 to 0.0095 mass %); P: 0.01 to 0.25 mass % (preferably 0.02 to 0.2 mass %, more preferably 0.03 to 0.16 mass %, and most preferably 0.04 to 0.12 mass %); at least one element selected from Sn: 0.05 to 1.5 mass % (preferably 0.1 to 0.9 mass %, more preferably 0.2 to 0.7 mass %, and most preferably 0.25 to 0.6 mass %), As: 0.02 to 0.25 mass % (preferably 0.03 to 0.15 mass %), and Sb: 0.02 to 0.25 mass % (preferably 0.03 to 0.15 mass %); and Zn: balance, and meeting the following conditions of (1) to (7). In the second copper alloy, it is preferable to additionally meet the following conditions of (10) to (15), inclusive of the conditions of (1) to (7). When the second copper alloy requires cutting, it is preferable to additionally meet a condition of (17), inclusive of the conditions of (1) to (7) and (10) to (15).

Thirdly, the present invention proposes a copper alloy (hereinafter, referred to as a "third copper alloy"), containing at least one element selected from Al, Mn and Mg in addition to the constituent elements of the first copper alloy, that is, consisting essentially of Cu: 69 to 88 mass % (preferably 70 to 84 mass %, more preferably 71.5 to 79.5 mass %, and most preferably 73 to 79 mass %); Si: 2 to 5 mass % (preferably 2.2 to 4.8 mass %, more preferably 2.5 to 4.5 mass %, and most preferably 2.7 to 3.7 mass %); Zr: 0.0005 to 0.04 mass % (preferably 0.0008 to 0.029 mass %, more preferably 0.001 to 0.019 mass %, still more preferably 0.0025 to 0.014 mass %, and most preferably 0.004 to 0.0095 mass %); P: 0.01 to 0.25 mass % (preferably 0.02 to 0.2 mass %, more preferably 0.03 to 0.16 mass %, and most preferably 0.04 to 0.12 mass %); at least one element selected from Al: 0.02 to 1.5 mass % (preferably 0.1 to 1.2 mass %), Mn: 0.2 to 4 mass % (preferably 0.5 to 3.5 mass %) and Mg: 0.001 to 0.2 mass %; and Zn: balance, and meeting the following conditions of (1) to (7). In the third copper alloy, it is preferable to additionally meet the following conditions of (10) to (15), inclusive of the conditions of (1) to (7). When the third copper alloy requires cutting, it is preferable to additionally meet a condition of (17), inclusive of the conditions of (1) to (7) and (10) to (15).

Fourthly, the present invention proposes a copper alloy (hereinafter, referred to as a "fourth copper alloy"), containing at least one element selected from Sn, As and Sb and at least one element selected from Al, Mn and Mg in addition to the constituent elements of the first copper alloy, that is, consisting essentially of Cu: 69 to 88 mass % (preferably 70 to 84 mass %, more preferably 71.5 to 79.5 mass %, and most preferably 73 to 79 mass %); Si: 2 to 5 mass % (preferably 2.2 to 4.8 mass %, more preferably 2.5 to 4.5 mass %, and most preferably 2.7 to 3.7 mass %), Zr: 0.0005 to 0.04 mass % (preferably 0.0008 to 0.029 mass %, more preferably 0.001 to 0.019 mass %, still more preferably 0.0025 to 0.014 mass %, and most preferably 0.004 to 0.0095 mass %); P: 0.01 to 0.25 mass % (preferably 0.02 to 0.2 mass %, more preferably 0.03 to 0.16 mass %, and most preferably 0.04 to 0.12 mass %); at least one element selected from Sn: 0.05 to 1.5 mass % (preferably 0.1 to 0.9 mass %, more preferably 0.2 to 0.7 mass %, and most preferably 0.25 to 0.6 mass %), As: 0.02 to 0.25 mass % (preferably 0.03 to 0.15 mass %) and Sb: 0.02 to 0.25 mass % (preferably 0.03 to 0.15 mass %); at least one element selected from Al: 0.02 to 1.5 mass % (preferably 0.1 to 1.2 mass %), Mn: 0.2 to 4 mass % (preferably 0.5 to 3.5 mass %) and Mg: 0.001 to 0.2 mass %; and Zn: balance, and meeting the following conditions of (1) to (7). In the fourth copper alloy, it is preferable to additionally meet the following conditions of (10) to (15), inclusive of the conditions of (1) to (7). When the fourth copper alloy requires cutting, it is preferable to additionally meet a condition of (17), inclusive of the conditions of (1) to (7) and (10) to (15).

Fifthly, the present invention proposes a copper alloy (hereinafter, referred to as a "fifth copper alloy") containing at least one element selected from Pb, Bi, Se and Te in addition to the constituent elements of the first copper alloy, that is, consisting essentially of Cu: 69 to 88 mass % (preferably 70 to 84 mass %, more preferably 71.5 to 79.5 mass %, and most preferably 73 to 79 mass %), Si: 2 to 5 mass % (preferably 2.2 to 4.8 mass %, more preferably 2.5 to 4.5 mass %, and most preferably 2.7 to 3.7 mass %); Zr: 0.0005 to 0.04 mass % (preferably 0.0008 to 0.029 mass %, more preferably 0.001 to 0.019 mass %, still more preferably 0.0025 to 0.014 mass %, and most preferably 0.004 to 0.0095 mass %); P: 0.01 to 0.25 mass % (preferably 0.02 to 0.2 mass %, more preferably 0.03 to 0.16 mass %, and most preferably 0.04 to 0.12 mass %), at least one element selected from Pb: 0.005 to 0.45 mass % (preferably 0.005 to 0.2 mass %, and more preferably 0.005 to 0.1 mass %), Bi: 0.005 to 0.45 mass % (preferably 0.005 to 0.2 mass %, and more preferably 0.005 to 0.1 mass %), Se: 0.03 to 0.45 mass % (preferably 0.05 to 0.2 mass %, and more preferably 0.05 to 0.1 mass %) and Te: 0.01 to 0.45 mass % (preferably 0.03 to 0.2 mass %, and more preferably 0.05 to 0.1 mass %); and Zn: balance, and meeting the following conditions of (1) to (8). In the fifth copper alloy, it is preferable to additionally meet the following conditions of (9) to (16), inclusive of the conditions of (1) to (8). When the fifth copper alloy requires cutting, it is preferable to additionally meet a condition of (17), inclusive of the conditions of (1) to (8) and (9) to (16).

Sixthly, the present invention proposes a copper alloy (hereinafter, referred to as a "sixth copper alloy"), containing at least one element selected from Sn, As and Sb in addition to the constituent elements of the fifth copper alloy, that is, consisting essentially of Cu: 69 to 88 mass % (preferably 70 to 84 mass %, more preferably 71.5 to 79.5 mass %, and most preferably 73 to 79 mass %); Si: 2 to 5 mass % (preferably 2.2 to 4.8 mass %, more preferably 2.5 to 4.5 mass %, and most preferably 2.7 to 3.7 mass %); Zr: 0.0005 to 0.04 mass % (preferably 0.0008 to 0.029 mass %, more preferably 0.001 to 0.019 mass %, still more preferably 0.0025 to 0.014 mass %, and most preferably 0.004 to 0.0095 mass %); P: 0.01 to 0.25 mass % (preferably 0.02 to 0.2 mass %, more preferably 0.03 to 0.16 mass %, and most preferably 0.04 to 0.12 mass %); Pb: 0.005 to 0.45 mass % (preferably 0.005 to 0.2 mass %, and more preferably 0.005 to 0.1 mass %), Bi: 0.005 to 0.45 mass % (preferably 0.005 to 0.2 mass %, and more preferably 0.005 to 0.1 mass %); Se: 0.03 to 0.45 mass % (preferably 0.05 to 0.2 mass %, and more preferably 0.05 to 0.1 mass %); Te: 0.01 to 0.45 mass % (preferably 0.03 to 0.2 mass %, and more preferably 0.05 to 0.1 mass %); at least one element selected from Sn: 0.05 to 1.5 mass % (preferably 0.1 to 0.9 mass %, more preferably 0.2 to 0.7 mass %, and most preferably 0.25 to 0.6 mass %), As: 0.02 to 0.25 mass % (preferably 0.03 to 0.15 mass %) and Sb 0.02 to 0.25 mass % (preferably 0.03 to 0.15 mass %); and Zn: balance, and meeting the following conditions of (1) to (8). In the sixth copper alloy, it is preferable to additionally meet the following conditions of (9) to (16), inclusive of the conditions of (1) to (8). When the sixth copper alloy requires cutting, it is preferable to additionally meet a condition of (17), inclusive of the conditions of (1) to (8) and (9) to (16).

Seventhly, the present invention proposes a copper alloy (hereinafter, referred to as a "seventh copper alloy"), containing at least one element selected from Al, Mn and Mg in addition to the constituent elements of the fifth copper alloy, that is, consisting essentially of Cu: 69 to 88 mass % (preferably 70 to 84 mass %, more preferably 71.5 to 79.5 mass %, and most preferably 73 to 79 mass %); Si: 2 to 5 mass % (preferably 2.2 to 4.8 mass %, more preferably 2.5 to 4.5 mass %, and most preferably 2.7 to 3.7 mass %); Zr: 0.0005 to 0.04 mass % (preferably 0.0008 to 0.029 mass %, more preferably 0.001 to 0.019 mass %, still more preferably 0.0025 to 0.014 mass %, and most preferably 0.004 to 0.0095 mass %); P: 0.01 to 0.25 mass % (preferably 0.02 to 0.2 mass %, more preferably 0.03 to 0.16 mass %, and most preferably 0.04 to 0.12 mass %); Pb: 0.005 to 0.45 mass % (preferably 0.005 to 0.2 mass %, and more preferably 0.005 to 0.1 mass %); Bi: 0.005 to 0.45 mass % (preferably 0.005 to 0.2 mass %, and more preferably 0.005 to 0.1 mass %); Se: 0.03 to 0.45 mass % (preferably 0.05 to 0.2 mass %, and more preferably 0.05 to 0.1 mass %); Te: 0.01 to 0.45 mass % (preferably 0.03 to 0.2 mass %, and more preferably 0.05 to 0.1 mass %); at least one element selected from Al: 0.02 to 1.5 mass % (preferably 0.1 to 1.2 mass %), Mn: 0.2 to 4 mass % (preferably 0.5 to 3.5 mass %) and Mg: 0.001 to 0.2 mass %; and Zn: balance, and meeting the following conditions of (1) to (8). In the seventh copper alloy, it is preferable to additionally meet the following conditions of (9) to (16), inclusive of the conditions of (1) to (8). When the seventh copper alloy requires cutting, it is preferable to additionally meet a condition of (17), inclusive of the conditions of (1) to (8) and (9) to (16).

Eighthly, the present invention proposes a copper alloy (hereinafter, referred to as a "eighth copper alloy"), containing at least one element selected from Sn, As and Sb and at least one selected from Al, Mn and Mg in addition to the constituent elements of the fifth copper alloy, that is, consisting essentially of Cu: 69 to 88 mass % (preferably 70 to 84 mass %, more preferably 71.5 to 79.5 mass %, and most preferably 73 to 79 mass %); Si: 2 to 5 mass % (preferably 2.2 to 4.8 mass %, more preferably 2.5 to 4.5 mass %, and most preferably 2.7 to 3.7 mass %); Zr: 0.0005 to 0.04 mass % (preferably 0.0008 to 0.029 mass %, more preferably 0.001 to 0.019 mass %, still more preferably 0.0025 to 0.014 mass %, and most preferably 0.004 to 0.0095 mass %); P: 0.01 to 0.25 mass % (preferably 0.02 to 0.2 mass %, more preferably 0.03 to 0.16 mass %, and most preferably 0.04 to 0.12 mass %); Pb: 0.005 to 0.45 mass % (preferably 0.005 to 0.2 mass %, and more preferably 0.005 to 0.1 mass %); Bi: 0.005 to 0.45 mass % (preferably 0.005 to 0.2 mass %, and more preferably 0.005 to 0.1 mass %); Se: 0.03 to 0.45 mass % (preferably 0.05 to 0.2 mass %, and more preferably 0.05 to 0.1 mass %); Te: 0.01 to 0.45 mass % (preferably 0.03 to 0.2 mass %, and more preferably 0.05 to 0.1 mass %); at least one element selected from Sn: 0.05 to 1.5 mass % (preferably 0.1 to 0.9 mass %, more preferably 0.2 to 0.7 mass %, and most preferably 0.25 to 0.6 mass %), As: 0.02 to 0.25 mass % (preferably 0.03 to 0.15 mass %) and Sb: 0.02 to 0.25 mass % (preferably 0.03 to 0.15 mass %), at least one element selected from Al: 0.02 to 1.5 mass % (preferably 0.1 to 1.2 mass %), Mn: 0.2 to 4 mass % (preferably 0.5 to 3.5 mass %) and Mg: 0.001 to 0.2 mass %; and Zn: balance, and meeting the following conditions of (1) to (8). In the eighth copper alloy, it is preferable to additionally meet the following conditions of (9) to (16), inclusive of the conditions of (1) to (8). When the eighth copper alloy requires cutting, it is preferable to additionally meet a condition of (17), inclusive of the conditions of (1) to (8) and (9) to (16).

In the following description, [a] represents the content of an element a, wherein the content of the element a is expressed by [a] mass %. For example, the content of Cu is expressed by [Cu] mass %. Further, [b] represents a content in terms of the area rate of a phase b, wherein the content (area rate) of the phase b is expressed by [b]%. For example, the content (area rate) of a phase, $\alpha$, is expressed by [$\alpha$]%. In addition, the content or area rate of each phase b is measured by an image analysis, and particularly obtained by binarization using an image processing software WinROOF (available from TECH-JAM Co., Ltd.) and is an average value of the area rates measured with three views.

(1) $f0=[Cu]-3.5[Si]-3[P]+0.5([Pb]+0.8([Bi]+[Se])+0.6[Te])-0.5([Sn]+[As]+[Sb])-1.8[Al]+2[Mn]+[Mg]=61$ to 71 (preferably f0=62 to 69.5, more preferably f0=62.5 to 68.5, and most preferably f0=64 to 67). Further, in the case of f0, [a]=0 as to a non-contained element a.

(2) $f1=[P]/[Zr]=0.7$ to 200 (preferably f1=1.2 to 100, more preferably f1=2.3 to 50, and most preferably f1=3.5 to 30).

(3) $f2=[Si]/[Zr]=75$ to 5000 (preferably f2=120 to 3000, more preferably f2=180 to 1500, and most preferably f2=300 to 900).

(4) $f3=[Si]/[P]=12$ to 240 (preferably f3=16 to 160, more preferably f3=20 to 120, and most preferably f3=25 to 80).

(5) Containing $\alpha$ phase and, $\kappa$ phase and/or $\gamma$ phase and $f4=[\alpha]+[\gamma]+[\kappa] \geqq 85$ (preferably $f4 \geqq 95$). Further, in the case of f4, [b]=0 as to a non-contained phase b.

(6) $f5=[\gamma]+[\kappa]+0.3[\mu]-[\beta]=5$ to 95 (preferably f5=10 to 70, more preferably f5=15 to 60, and most preferably f5=20 to 45). Further, in the case of f5, [b]=0 as to a non-contained phase b.

(7) Having an average grain diameter of 200 μm or less (preferably 150 μm or less, more preferably 100 μm or less, and most preferably 50 μm or less) in a macrostructure during melt-solidification. Here, the average grain diameter in the macrostructure (or microstructure) during melt-solidification refers to an average value of grain diameters in a macrostructure (or microstructure) in a state where deforming (extruding, rolling etc.) or heating is not carried out after melt-solidification by casting (including conventionally known various castings such as permanent mold casting, sand casting, horizontal continuous casting, upward casting (up-casting), semi-solid metal casting, semi-solid metal forging, melting forging), welding or melting cutting. Further, the term "casting" or "casting" used herein refers to any object the whole or part of which is melted and solidified, and for example includes a sand casting, a metal mold casting, a low pressure casting, a die-cast casting, a lost wax casting, a semi-solid casting (e.g., a thixo casting, a rheocasting, a semi-solid metal casting, a squeeze casting, a centrifugal casting, and a continuous casting (e.g., a rod, a hollow rod, an irregular shaped rod, an irregular shaped hollow rod, a coil, a wire etc. made by horizontal continuous casting, upward casting or up-casting), or a casting made by melting forging (direct forging), metallizing, build-up spraying, lining or overlay, including a rolling or extruding ingot, a slab and a billet. In addition, it should be understood that welding is included in the casting in a broad sense because a base metal is partly melted, solidified and bonded.

(8) $f6=[Cu]-3.5[Sl]-3[P]+3([pb]+0.8([Bi]+[Se])+0.6[Te])^{1/2} \geqq 62$ (preferably $f6 \geqq 63.5$), and $f7=[Cu]-3.5[Si]-3[P]-3([Pb]+0.8([Bi]+[Se])+0.6[Te])^{1/2} \leqq 68.5$ (preferably $f7 \leqq 67$). Further, in the cases of f6 and f7, [a]=0 as to a non-contained element a.

(9) $f8=[\gamma]+[\kappa]+0.3[\mu]-[\beta]+25([Pb]+0.8([Bi]+[Se])+0.6[Te])^{1/2} \geqq 10$ (preferably $f8 \geqq 20$) and $f9=[\gamma]+[\kappa]+0.3[\mu]-[\beta]-25([Pb]+0.8([Bi]+[Se])+0.6[Te])^{1/2} \leqq 70$ (preferably $f9 \leqq 50$). Further, in the cases of f7 and f8, [a]=0 or [b]=0 as to a non-contained element a or a non-contained phase b.

(10) A primary crystal generated during melt-solidification is $\alpha$ phase.

(11) Generating a peritectic reaction during melt-solidification.

(12) During melt-solidification, having a crystalline structure where a dendrite network is divided and a grain whose two-dimensional shape is a circular shape, a non-circular shape near the circular shape, an elliptical shape, a crisscross shape, an acicular shape or a polygonal shape.

(13) Having a matrix whose phase α is divided finely and whose phase K and/or phase γ are (is) uniformly distributed.

(14) In a semi-melted state having a solid phase fraction of 30 to 80%, having a crystalline structure where a dendrite network is at least divided and a solid phase whose two-dimensional shape is a circular shape, a non-circular shape near the circular shape, an elliptical shape, a crisscross shape or a polygonal shape.

(15) In a semi-melted state having a solid phase fraction of 60%, having a solid phase of an average grain diameter of 150 μm or less (preferably 100 μm or less, more preferably 50 μm or less, and most preferably 40 μm or less) and/or of an average maximum length of 200 μm or less (preferably 150 μm or less, more preferably 100 μm or less, and most preferably 80 μm or less).

(16) In the case that Pb or Bi is contained, having a matrix in which Pb or Bi particles of a fine and uniform size are uniformly distributed, wherein the Pb or Bi particles have an average grain diameter of 1 μm or less (but preferably have a maximum grain diameter not exceeding 3 μm (preferably 2 μm).

(17) In the case that cutting is carried out in a dry atmosphere by a lathe equipped with a bite of a rake angle: −6° and a nose radius: 0.4 mm under the conditions of a cutting speed: 80 to 160 m/min, a cutting depth: 1.5 mm and a feed speed: 0.11 mm/rev., having generated chips taking a small segment shape (FIG. 5A) of a trapezoidal or triangular shape, a tape shape (FIG. 5B) having a length of 25 mm or less or an acicular shape (FIG. 5C).

And, in the first to eighth copper alloys, Cu is a main element of each copper alloy, and is required to contain 69 mass % or more in order to secure corrosion resistance (dezincification corrosion resistance, and stress corrosion crack resistance) and mechanical properties as an industrial material. However, when the content of Cu exceeds 88 mass %, strength and wear resistance are deteriorated, so that there is a chance of hindering a grain refinement effect by co-addition of Zr and P as described below. In consideration of this, the content of Cu is required to have 69 to 88 mass %, preferably 70 to 84 mass %, more preferably 71.5 to 79.5 mass %, and most preferably 73 to 79 mass %. Further, in order to facilitate grain refinement, it is necessary to make great account of relation with other elements to be contained and to meet the condition of (1). In other words, the contents of Cu and other constituent elements are required to obtain relation of f0=[Cu]−3.5[Si]−3[P]+0.5([Pb]+0.8([Bi]+[Se])+0.6[Te])−0.5([Sn]+[As]+[Sb])−1.8[Al]+2[Mn]+[Mg]=61 to 71, preferably f0=62 to 69.5, more preferably f0=62.5 to 68.5, and most preferably f0=64 to 67. Further, a lower limit of f0 is a value indicating whether a primary crystal is a phase α or not, and an upper limit is a value indicating whether the peritectic reaction is generated or not.

In the first to eighth copper alloys, Zn is a main element of each copper alloy together with Cu and Si, and acts to lower stacking fault energy of the alloy, generate the peritectic reaction, and provide refinement of grains in a melted and solidified material, improvement of fluidity and decrease of melting point in a molten metal, prevention of oxidation loss of Zr, improvement of corrosion resistance and improvement of machinability. In addition, Zn serves to improve mechanical strengths such as tensile strength, yield strength, impact strength and fatigue strength. In consideration of this, a content of Zn is set to a balance excluding the content of each constituent element.

In the first to eighth copper alloys, when being added together with Zr, P, Cu and Zn, Si is an element serving to lower stacking fault energy of the alloy, to widen a composition range taking part in the peritectic reaction and exert a significant refinement effect of grains. Si has an effect when its addition amount is 2% or more. However, even when Si is added above 5%, grain refinement caused by co-addition with Cu and Zn is saturated or deteriorated in reverse, and furthermore causes deterioration of ductility. Further, when the content of Si exceeds 5%, thermal conductivity is deteriorated and a solidification temperature range is widened, so that there is a chance of deteriorating castability. Meanwhile, Si acts to improve fluidity of a molten metal, prevent oxidation of the molten metal, and lower a melting point. In addition, Si serves to improve corrosion resistance, and particularly dezincification corrosion resistance, and stress corrosion crack resistance. Furthermore, Si contributes to improvement of machinability as well as mechanical properties such as tensile strength, yield strength, impact strength and so on. These actions cause a synergy effect on grain refinement of castings. For the purpose of effective exertion of this addition function of Si, the content of Si is required to have a range of 2 to 5 mass %, preferably 2.2 to 4.8 mass %, more preferably 2.5% to 4.5%, and most preferably 2.7 to 3.7 mass % on the condition of meeting the condition of (1).

In the first to eighth copper alloys, Zr and P are co-added in order to facilitate refinement of copper alloy grains, and particularly during melt-solidification. In other words, Zr and P individually facilitate the refinement of copper alloy grains to a somewhat degree like other ordinary addition elements, but exerts a very significant grain refinement function in a co-existence state.

In regard to Zr, this grain refinement function is exerted at 0.0005 mass % or more, effectively at 0.0008 mass % or more, significantly at 0.001 mass % or more, more significantly at 0.0025 mass % or more, and very significantly at 0.004 mass % or more. In regard to P, this grain refinement function is exerted at 0.01 mass % or more, effectively at 0.02 mass % or more, more significantly at 0.03 mass % or more, and very significantly at 0.04 mass % or more.

Meanwhile, when the addition amount of Zr amounts to 0.04 mass % and that of P amounts to 0.25 mass %, the grain refinement function by co-addition of Zr and P is saturated regardless of kinds and contents of other constituent elements. Therefore, the addition amounts of Zr and P which are required to effectively exert this function are 0.04 mass % or more for Zr and 0.25 mass % or more for P. Further, when the addition amounts of Zr and P are small as set to the range, Zr and P can uniformly distribute a high concentration of Sn, which is allotted to a phase γ with priority, in a matrix without continuation by means of the grain refinement, for example, even when the copper alloy contains Sn without deteriorating properties of the alloy exerted by other constituent elements, so that it is possible to prevent a casting crack, obtain a sound casting having low porosity, shrinkage cavity, blow hole and micro-porosity, and improve working performance such as cold stretching or drawing performed after casting, and thus it is possible to further improve the properties of the alloy of interest. Further, from an industrial point of view of adding a very small amount of Zr, the grain refinement effect is not still more exerted even when Zr is added in excess of 0.019 mass %. The grain refinement effect may be damaged when Zr exceeds 0.029 mass %, and is clearly deprived when Zr exceeds 0.04 mass %.

Further, because Zr has very strong affinity with oxygen, it is easy to generate oxide and sulfide of Zr when Zr is melted in the air or uses scraps as a raw material. When Zr is excessively added, viscosity of the molten metal is increased to cause casting defects by inclusion of the oxide and sulfide during casting, so that it is easy to generate the blow hole or micro porosity. In order to avoid this, it can be considered to carry out melting and casting under vacuum or complete inert gas atmosphere. In this case, versatility disappears, and costs are considerably increased in the copper alloy where Zr is merely added as the refinement element. In this regard, the addition amount of Zr which is not formed of the oxide and sulfide is preferably set to 0.029 mass % or less, more preferably 0.019 mass % or less, still more preferably 0.014 mass % or less, and most preferably 0.0095 mass %. Furthermore, when the amount of Zr is set to this range, the generation of the oxide or sulfide of Zr is decreased even when the corresponding copper alloy is melted in the air as a recycling material without new addition of a virgin material (or is cast using the raw material consisting only of the corresponding recycling materials). Thereby, it is possible to obtain the sound first to eighth copper alloys formed of fine grains again.

In this respect, the addition amount of Zr is required to have a range of 0.0005 to 0.04 mass %, preferably 0.0008 to 0.029 mass %, more preferably 0.001 to 0.019 mass %, still more preferably 0.0025 to 0.014 mass %, and most preferably 0.004 to 0.0095 mass %.

Further, P is added to exert the grain refinement function by the co-addition with Zr and exerts an influence on the corrosion resistance, castability and so on. Thus, considering the influence exerted on the corrosion resistance, castability etc. in addition to the grain refinement function by the co-addition with Zr, the addition amount of P is required to have a range of 0.01 to 0.25 mass %, preferably 0.02 to 0.2 mass %, more preferably 0.03 to 0.16 mass %, and most preferably 0.04 to 0.12 mass %. P has important relation with Zr, but is not favorable in that even when it is added in excess of 0.25 mass %, the refinement effect is small, and rather the ductility is damaged.

And, the grain refinement effect by the co-addition of Zr and P is not exerted only by individually determining the contents of Zr and P in the above-mentioned range, but is required to meet the condition of (2) in their mutual contents. The grain refinement is achieved by causing a nucleation speed of the $\alpha$ phase of the primary crystal crystallized from a melted melting to be still higher than a growth speed of a dendrite crystal. In order to generate this phenomenon, it is insufficient only to individually determine the addition amounts of Zr and P, and it is necessary to consider a co-addition ratio of (f1=[P]/[Zr]). By determining the contents of Zr and P to have an appropriate addition ratio in an appropriate range, it is possible to remarkably facilitate crystallization of the $\alpha$ phase of the primary crystal by means of the co-addition function or interaction of Zr and P. As a result, the nucleation of the corresponding $\alpha$ phase exceeds the growth of the dendrite crystal. When the contents of Zr and P are within the appropriate range and their combined ratio ([P]/[Zr]) is stoichiometric, the addition of Zr reaching several ppm allows intermetallic compounds of Zr and P (e.g., ZrP, $ZrP_{1-x}$ etc.) to be generated in the $\alpha$ phase crystal, and the nucleation speed of the corresponding $\alpha$ phase is increased as the value f1 of [P]/[Zr] reaches a range of 0.7 to 200, more increased when f1=1.2 to 100, significantly increased when f1=2.3 to 50, and drastically increased when f1=3.5 to 30. In other words, the co-addition ratio of Zr and P is an important factor in facilitating the grain refinement, and the crystal nucleation during melt-solidification greatly exceeds the crystal growth when f1 is within the range. Further, in order to make the grains fine, co-addition ratios of Zr and Si and of P and Si (f2=[Si]/[Zr] and f3=[Si]/[P]) are sufficiently important and are required to be considered.

And when the melt-solidification proceeds to increase a fraction of the solid phase, the crystal growth begins to occur frequently. This begins to generate amalgamation of grains in part. In general, the $\alpha$ phase grains are gradually increased in size. Here, while the melting is solidified, the peritectic reaction occurs. Then, a solid-liquid reaction between the melted melting left without being solidified and the solid $\alpha$ phase is generated, thereby creating a phase, $\beta$, by consuming the solid $\alpha$ phase. As a result, the $\alpha$ phase is enclosed by the $\beta$ phase, and thus the $\alpha$ phase grain itself begins not only to be decreased in size but also take an angled elliptical shape. In this manner, when the solid phase takes the fine elliptical shape, gases are easy to escape, and shrinkage is smoothly generated with tolerance to the crack resulting from solidification shrinkage when solidified, which has a good influence on the various properties such as the strength, corrosion resistance etc. at a room temperature. Of course, when the solid phase takes the fine elliptical shape, fluidity is ameliorated, and thus it is optimal to use a semi-solid metal solidification. When the solid phase of the fine elliptical shape and the melted melting are left in the final step of solidification, the solid phase and melted melting are sufficiently supplied every nook and corner even when a mold has a complicated shape, so that the casting of a good shape is formed. That is, the casting is formed up to a near net shape (NNS). Further, whether to take part in the peritectic reaction or not is generally generated at a composition wider than that of an equilibrium state, unlike that of the equilibrium state from the practical point of view. Here, a relation f0 plays an important role, and an upper limit of f0 has a main interrelation with a size of a grain after melt-solidification and a criterion capable of taking part in the peritectic reaction. A lower limit of f0 has a main interrelation with a size of a crystal after melt-solidification and a boundary value whether a primary crystal is a phase $\alpha$ or not. As f0 falls to the above-mentioned preferable range (f0=62 to 69.5), more preferable range (f0=62.5 to 68.5), and most preferable range (f0=64 to 67), the primary crystal, $\alpha$ phase, is increased in quantity, and thus the peritectic reaction generated in a non-equilibrium reaction is still more activated. Consequently, the grain obtained at a room temperature becomes smaller.

Of course, these series of melt-solidification phenomena are dependent on a cooling rate. Specifically, in a rapid cooling where the cooling rate has an order of $10^{5°}$ C./sec or more, there is no time to perform nucleation of the crystal, so that there is a chance that the grain is not refined. In contrast, in a slow cooling where the cooling rate has an order of $10^{-3°}$ C./sec or less, the grain growth or the grain amalgamation is promoted, so that there is a chance that the grain is not refined. Further, approach to the equilibrium state causes the composition range taking part in the peritectic reaction to become narrow. More preferably, the cooling rate in the step of melt-solidification has a range from $10^{-2}$ to $10^{4°}$ C./sec, and most preferably a range from $10^{-1}$ to $10^{3°}$ C./sec. Among this range of the cooling rate, the nearer the upper limit the cooling rate reaches, the wider the composition range where the grain is refined becomes, thereby the grains are further refined. The $\beta$ phase generated in the peritectic reaction serves to suppress the grain growth. However, when the $\beta$ phase stays in the metal structure at a high temperature, and when the K phase and/or γ phase are precipitated and generated by a solid phase reaction, thus K and γ phases constitute a large fraction of the total structure, the crystal growth is suppressed, and α grain is made finer. The conditional expressions for this are as follows: f4=[α]+[γ]+[K] and f5=[γ]+[K]+0.3[μ]−[β]. As f5 falls to the above-mentioned preferable range (f5=10 to 70), more preferable range (f5=15 to 60), and most preferable range (f5=20 to 45), the grain is made finer. In the condition of (8), f6 and f7 are similar to f0, and in the condition of (9), f5 is similar to f5. Thus, meeting the conditions of (8) and (9) leads to meeting the condition of (1) for to and the condition of (6) for f5. Further, the K phase and the γ phase formed in the Cu—Zn—Si based alloy having the composition range specified in the present invention are Si-rich hard phases. When cutting, these K and γ phases act as a stress concentration source and generate thin cutting chips of a shear type, so that parted cutting chips are obtained, and, consequently, the low cutting resistance is shown at the same time. Accordingly, when the K and γ phases are uniformly distributed even without existence of soft Pb or Bi particles as a machinability improving elements (i.e., without containing the machinability improving elements such as Pb, Bi etc.), the machinability that is satisfactory industrially is obtained. A condition for exerting a machinability improving effect that is not dependent on this machinability improving elements of Pb etc. is the condition of (1) and the condition of (6) for f5. However, today, there is a demand on high-speed cutting. To this end, the hard K and γ phases and the soft Pb or Bi particles are uniformly distributed in a matrix. This coexistence exerts an abrupt synergy effect, particularly, under the condition of the high-speed cutting. In order to exert this co-addition effect, it is required to meet the condition of (8), and preferably to additionally meet the condition of (9).

As seen from the foregoing, in the first to eighth copper alloys, by at least meeting the conditions of (1) to (6), even the melted solidified substance can facilitate the same grain refinement as a hot-worked material or recrystallized material, and by meeting the condition of (10), it is possible to facilitate making the grain still finer. Further, in the fifth to eighth copper alloys, by meeting the condition of (8) (preferably, the condition of (9) in addition to the condition of (8)), it is possible to facilitate the grain refinement together with improvement of the machinability by trace addition of Pb etc. Further, when the K and γ phases has higher concentration of Si than the α phase, and when these three phases do not amount to 100%, the balance generally includes at least one of β, μ and δ phases.

In the fifth to eighth copper alloys, as well-known, Pb, Bi, Se and Te improve the machinability and simultaneously exert excellent wear resistance by improving conformability and slidability to the other member in an abrasion engagement member such as a bearing or the like. For the purpose of exertion of this function, mass addition of Pb etc. is required, but by meeting the condition of (8) the trace addition of Pb etc. is carried out without the mass addition of Pb etc., so that it is possible to secure the machinability that can be industrially satisfactory together with the grain refinement. In order to facilitate still more improving the machinability by the trace addition of Pb etc., it is preferable to meet the conditions of (9) and (16) in addition to the condition of (8). By meeting these conditions, the grains are made finer, and by distributing the particles of Pb etc. in the matrix at a finer uniform size, it is possible to improve the machinability without the mass addition of Pb etc. These effects are remarkably exerted under the condition of, particularly, the high-speed cutting together with existence of the hard K and γ phases and the non-solid melting soft Pb and Bi, which are formed within the present composition range effective for the machinability. In general, Pb, Bi, Se and Te are subjected to individual addition, or common addition by any combination of Pb and Te; Bi and Se; or Bi and Te. In this respect, on condition of meeting the condition of (8) etc. the addition amount of Pb is required to have a range from 0.005 to 0.45 mass %, preferably from 0.005 to 0.2 mass %, and more preferably from 0.005 to 0.1 mass %. Further, the addition amount of Bi is required to have a range from 0.005 to 0.45 mass %, preferably from 0.005 to 0.2 mass %, and more preferably from 0.005 to 0.1 mass %. Further, the addition amount of Se is required to have a range from 0.03 to 0.45 mass %, preferably from 0.05 to 0.2 mass %, and more preferably from 0.05 to 0.1 mass %. In addition, the addition amount of Te is required to have a range from 0.01 to 0.45 mass %, preferably from 0.03 to 0.2 mass %, and more preferably 0.05 to 0.1 mass %.

Pb and Bi are not entered into solid melting at a room temperature, exist as the Pb particle or the Bi particle as well as are distributed in a granular form in a melted state in the step of melt-solidification and exist between solid phases. The more the particles of Pb and Bi, the easier a crack is generated in the step of melt-solidification (by generation of tensile stress depending on the shrinkage by the solidification). Further, Pb and Bi mainly exist at a grain boundary in the melted state after solidification, so that when their particles are increased, it is easy to generate a hot crack. In order to solve this problem, it is very effective to refine the grain to relieve stress (i.e., to increase an area of the grain boundary), and to cause the particles of Pb and Bi to be decreased in size and uniformly distributed. Further, Pb and Bi have an adverse influence on the copper alloy properties except the machinability, as set forth above. In regard to ductility at a room temperature, the stress is concentrated on the particles of Pb and Bi, so that the ductility is damaged (It goes without saying that when the grain is large, the ductility is geometrically damaged). It should be paid attention that this problem can be overcome by the grain refinement.

In the second, fourth, sixth and eighth copper alloys, Sn, As and Sb are added to mainly improve cavitation erosion resistance, corrosion resistance (in particular, dezincification corrosion resistance). This function is exerted by adding 0.05 mass % or more for Sn and 0.02 mass % or more for Sb and As. However, although Sn, As and Sb are added in excess of a certain amount, it is impossible to obtain an effect suitable for the addition amount, and ductility is rather deteriorated. Sn alone has a small influence on the refinement effect, but can exert the refinement function of the grain under the existence of Zr and P. Sn is to improve mechanical properties (strength, etc.), corrosion resistance, and wear resistance. Further, Sn serves to more effectively perform the peritectic reaction by widening the composition range of Cu or Zn which divides the dendrite arm to generate the peritectic reaction, and decreases stacking fault energy of the alloy to thus more effectively realize granulation and refinement of the grain. Sn is a low melting point metal, which forms Sn-concentrated phase or concentrated part to impede castability even if being added at a small amount. However, when Sn is added under the addition of Zr and P, this has effect on the grain refinement by Sn, and simultaneously this grain refinement causes the Sn-concentrated phases to be uniformly distributed in spite of the formation of the Sn-concentrated part, thus showing excellent cavitation erosion resistance without greatly damaging castability or ductility. In order to exert an effect of the cavitation erosion resistance, Sn requires its addition amount of 0.05% or more, preferably 0.1% or more, and more preferably 0.25% or more. Meanwhile, when exceeding 1.5%, the addition amount of Sn causes trouble on the castability or ductility at a room temperature no matter how fine the grain may be made, and preferably is 0.9% or less, more preferably 0.7% or less, and most preferably 0.6% or less. The addition amount of Sn is necessary to be set to a range from 0.05 to 1.5 mass %, preferably from 0.1 to 0.9 mass %, more preferably from 0.2 to 0.7 mass %, and most preferably from 0.25 to 0.6 mass %. Further, the addition amounts of As and Sb are necessary to be set to a range from 0.02 to 0.25 mass %, and preferably from 0.03 to 0.15 mass % considering their toxicity having an adverse influence on a human body.

In the third, fourth, seventh and eighth copper alloys, Al, Mn and Mg are added to mainly facilitate improvement of strength, improvement of melt fluidity, deoxidation, desulfurization effect, improvement of cavitation erosion resistance under a high-speed flow rate, and improvement of wear resistance. Further, Al forms a hard corrosion resistant thin film of Al—Sn on a casting surface to improve the wear resistance. Further, Mn has the effect generating a corrosion resistant thin film between itself and Sn. Besides, Mn combines with Si in the alloy to form an intermetallic compound of Mn—Si (atomic ratio: 1:1 or 2:1), and has the effect improving the wear resistance of the alloy. However, a scrap material (e.g. a disused heating pipe etc.) is often used as a part of a copper alloy raw material, and an S component (sulfur component) is often contained in this scrap material. When the S component is included in a molten metal, Zr, an element for the grain refinement, forms a sulfide. Thereby, there is a chance that an effective grain refinement function by Zr is lost. Further, the melt fluidity is deteriorated, and thus it is easy to generate casting defects such as a blow hole, crack and so forth. Mg has a function of improving the melt fluidity in casting when using the scrap material containing this S component as the alloy raw material, in addition to the function of improving the corrosion resistance. Further, Mg can remove the S component in a form of MgS which is more unharmful, wherein MgS is not harmful to the corrosion resistance even if it remains behind in the alloy, and can effectively prevent decrease of the corrosion resistance caused by the S component contained in the raw material. Further, when the S component is contained in the raw material, there is a chance that because S is easy to exist at a grain boundary, intergranular corrosion is generated. However, the intergranular corrosion can be effectively prevented by addition of Mg. In addition, Al and Mn act also to remove the S component included in the molten metal although being inferior to Mg. Furthermore, when a large quantity of oxygen exists in the molten metal, there is a chance that Zr forms an oxide and thus the refinement function of the grain is lost. However, Mg, Al and Mn exert an effect of preventing the formation of the Zr oxide. In consideration of this, the contents of Al, Mn and Mg are set to the above-mentioned range. Further, there is a chance that S concentration of the molten metal is increased and thus Zr is consumed by S, but when Mg of 0.001 mass % or more is contained in the molten metal prior to charging of Zr, the S component of the molten metal is removed or fixed in the form of MgS, and thus this problem does not occur. However, when Mg is added in excess of 0.2 mass %, Mg is subjected to oxidation like Zr, and the molten metal is increased in viscosity, and there is a chance of generating casting defects by, for example, inclusion of the oxide. Considering this and improvement of the strength, the cavitation erosion resistance and the wear resistance in all, the addition amount of Al is necessary to be set to a range from 0.02 to 1.5 mass %, and preferably from 0.1 to 1.2 mass %. Further, considering effects of improving the wear resistance by formation of Si and an intermetallic compound of MnSi (at an atomic ratio of 1:1 or 1:2) in the alloy in all, the addition amount of Mn is necessary to be set to a range from 0.2 to 4 mass %, and preferably from 0.5 to 3.5 mass %. Mg is necessary to be added at a range from 0.001 to 0.2 mass %.

In the first to eighth copper alloys, by adding Zr and P, the refinement of the grain is realized. By meeting the condition of (7), that is by setting the average grain diameter in a macrostructure during melt-solidification to 200 μm or less (preferably 150 μm or less, more preferably 100 μm or less, and most preferably 50 μm or less in a microstructure), a high quality of casting can be obtained, and provision and practical use of the casting by continuous casting such as horizontal continuous casting, upward casting (up-casting) etc. are possible. When the grain is not refined, the heat treatment is required several times for the purpose of removing the dendrite structure characteristic of the casting or facilitating division, subdivision of the K phase and the γ phase, and its surface state becomes bad because the grain is coarsened. In contrast, when the grain is refined as set forth above, it is not necessary to perform this heat treatment because segregation is merely micro-structural, and the surface state becomes good. Further, the K phase and the γ phase are mainly present at a phase boundary with the γ phase. Thus, the more the grains are minute and uniformly distributed, the shorter lengths of their phases become. For this reason, a peculiar processing process for dividing the K phase and the γ phase are not required or can be minimized even if required. In this manner, it is possible to sharply reduce the number of processes required for production to thus decrease production costs as much as possible. Further, by meeting the condition of (7), the following problems do not occur, and excellent properties of the copper alloy are exerted. In other words, when the K phase and the γ phase are not uniformly distributed, a strength difference from the α phase of the matrix easily generates a crack and damages ductility at a room temperature. Further, since particles of Pb or Bi exist at a boundary with the α phase or at a grain boundary, a large-size phase easily generates a solidification crack and damages the ductility at the room temperature.

Further, when the K and γ phases or the Pb and Bi particles meet the condition of (13) (and additionally the condition of (16) in the fifth to eighth copper alloys) are uniformly distributed in the matrix in a uniform size and fine shape, it is natural for cold workability to be improved. As such, castings of the first to eighth copper alloys can be appropriately used for application requiring caulking (for example, in the case of a hose nipple, the caulking is often carried out when installed).

Further, in the castings of the first to eighth copper alloys, there are many cases of using the scrap material in the raw material. In the case of using this scrap material, impurities are often contained inevitably, which is allowed from the practical point of view. However, in the case where the scrap material is a nickel plating material or the like, when Fe and/or Ni are contained as the inevitable impurities, it is necessary to restrict their contents. That is, this is because, when the contents of their impurities are high, Zr and P useful to refinement of the grain are spent by Fe and/or Ni. For instance, this is because, although Zr and P are excessively added, there is a problem of hindering the refinement action of the grain. Accordingly, when any one of Fe and Ni is contained, its content is preferably restricted to 0.3 mass % or less (preferably 0.2 mass % or less, more preferably 0.1 mass % or less, and most preferably 0.05 mass % or less). Further, when Fe and Ni are contained together, their total content is preferably restricted to 0.35 mass % or less (preferably 0.25 mass % or less, more preferably 0.15 mass % or less, and most preferably 0.07 mass % or less).

In the exemplary embodiment, the first to eighth copper alloys are provided, for example, as a casting obtained in the casting process or a plastic worked material which additionally performs plastic working on the casting once or more.

The casting is provided as a wire, a rod or a hollow bar which is cast by the horizontal continuous casting, upward casting or up-casting, as well as what is cast in a near net shape. Further, the casting is provided as a casting, semi-solid metal casting, a semi-solid metal formed material, a melt forged material, or a die-cast formed material. In this case, it is preferable to meet the conditions of (14) and (15). When the solid phase in a semi-melted state is granulated, it is natural for semi-solid metal castability to become excellent, and thus it is possible to carry out the semi-solid metal casting. Further, the fluidity of the melt including the solid phase in the final solidification step is mainly dependent on a shape of the solid phase in the semi-melted state, and viscosity or composition of the liquid phase. However, regarding the good or bad (high precision) of formability or complicated shape by casting is required, the former (the shape of the solid phase) has more influence on whether a sound casting can be cast or not. In other words, when the solid phase in the semi-melted state begins to form a network of the dendrite, the melt including the solid phase is difficult to spread to all the corners. In this respect, the formability by casting is deteriorated, and thus it is difficult to obtain the casting having the high precision or complicated shape. Meanwhile, the solid phase in the semi-melted state is granulated, and as the solid phase becomes more spheroidized (the circular shape in a two-dimensional shape) and smaller in grain diameter, castability including the semi-solid metal castability becomes excellent, and it is possible to obtain the sound casting having the high precision or complicated shape (of course, to obtain the semi-melted casting having the high precision). Therefore, by knowing the shape of the solid phase in the semi-melted state, it is possible to evaluate the semi-solid metal castability. By the good or bad of the semi-solid metal castability, it is possible to check the good or bad of other castability (complicated shape castability, precision castability, and melting forgeability). In general, in the semi-melted state having a solid phase fraction from 30 to 80%, the dendrite network at least has a divided crystalline structure. Further, when the two-dimensional shape of the solid phase has a non-circular shape near the circular shape, an elliptical shape, a crisscross shape or a polygonal shape, the semi-solid metal castability is good. Furthermore, in particular, in the semi-melted state having a solid phase fraction of 60%, when the corresponding solid phase falls to at least one of one having an average grain diameter of 150 µm or less (preferably 100 µm or less, more preferably 50 µm or less, and most preferably 40 µm or less) and one having an average maximum length of 300 µm or less (preferably 150 µm or less, more preferably 100 µm or less, and most preferably 80 µm or less) (particularly, in the elliptical shape, when an average ratio of a major side to a minor side is 3:1 or less (preferably 2:1 or less), the semi-solid metal castablilty is excellent.

Further, the plastic worked material is provided, for example, as a hot extruded material, a hot forged material or a hot rolled material. In addition, the plastic worked material is provided as the wire, the rod or the hollow bar formed by drawing the casting. Further, when the plastic worked material is provided as a plastic worked material obtained by cutting, i.e. a cut material, it is preferable to meet the condition of (17), namely it is preferable that, when the cutting is performed in a dry atmosphere by a lathe using a bite having a rake angle of −6° and a nose radius of 0.4 mm under the conditions: a cutting speed from 80 to 160 m/min, a cutting depth of 1.5 mm and a feed speed of 0.11 mm/rev., cut chips having a trapezoidal or triangular small segment shape, and a tape or acicular shape having a length of 25 mm or less are generated. This is because processing (collection or reuse) of the cut chips is easy, and the good cutting can be carried out without generating troubles that the cut chips stick to the bite, damage a cutting surface or the like.

The first to eighth copper alloys are provided as a water contact fitting that is used in contact with water at all times or temporally. For example, the water contact fitting is provided as a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a main cock, a handle cock, a gland cock, a two-way cock, a three-way cock, a four-way cock, a gas cock, a ball valve, a safety valve, a relief valve, a pressure reducing valve, an electromagnetic valve, a steam trap, a water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case or their constituent member. Further, the first to eighth copper alloys are provided as a frictional engagement member that performs relative movement in contact with the other member at all times or temporally. For example, the frictional engagement member is provided as a gear, a sliding bush, a cylinder, a piston shoe, a bearing, a bearing part, a bearing member, a shaft, a roller, a rotary joint part, a bolt, a nut, or a screw shaft or their constituent member. Furthermore, it is provided as a pressure sensor, a temperature sensor, a connector, a compressor part, a carburetor part, a cable fixture, a mobile phone antenna part, or a terminal.

Further, the present invention proposes a casting method of a copper alloy casting having excellent machinability, strength, corrosion resistance and wear resistance, characterized in that, in the case of producing the first to eighth copper alloys, Zr (contained for the purpose of still more refinement of a grain and stable refinement of the gain) is added in a form of a copper alloy material containing the same just before casting or in the final step of fusing a raw material in a casting process, thereby preventing Zr from being added in a form of an oxide and/or sulfide in casting. As the copper alloy material containing Zr, Cu—Zn alloy, Cu—Zn—Zr alloy, and the alloys further containing at least one selected from P, Mg, Al, Sn, Mn and B are preferable.

In other words, in the casting process of the first to eighth copper alloys or the components thereof (materials to be shaped), the loss of Zr, generated while Zr is added, is decreased as much as possible by adding Zr as an intermediate alloy material (copper alloy material) in the shape of granular material, thin sheet-like material, rod-like material or wire-like material just before the casting. Then, Zr is not added in the form of oxide and/or sulfide when casting, thereby the amount of Zr necessary and sufficient to refine the grains can be obtained. And in the case of adding Zr just before the casting in this manner, since a melting point of Zr is 800 to 1000° C. higher than that of the corresponding copper alloy, it is preferable to use a low melting alloy material that is an intermediate alloy material shaping like granule (grain diameter from about 2 to 50 mm), thin sheet (thickness from about 1 to 10 mm), rod (diameter from about 2 to 50 mm) or wire and having the melting point near that of the corresponding copper alloy and a lot of necessary components (for example, Cu—Zn alloy or Cu—Zn—Zr alloy containing 0.5 to 65 mass % of Zr or the alloys further containing at least one element (0.1 to 5 mass % of each is contained) selected from P, Mg, Al, Sn, Mn and B). In particular, in order to lower the melting point to facilitate melting and simultaneously prevent any loss by oxidation of Zr, it is preferable used in the form of an alloy material based on the Cu—Zn—Zr alloy containing 0.5 to 35 mass % Zr and 15 to 50 mass % Zn (more preferably 1 to 15 mass % Zr and 25 to 45 mass % Zn). While being dependent on a combined ratio of itself and co-added P, Zr is an element of hindering electric thermal conductivity as intrinsic property of the copper alloy. However, when an amount of Zr that does not take the form of the oxide and/or sulfide is less than 0.04 mass % and particularly 0.019 mass %, reduction of the electric thermal conductivity by addition of Zr is not almost caused. For instance, even when the electric thermal conductivity is reduced, the reduced rate will do if it is a very low rate compared with the case of not adding Zr.

Further, in order to obtain the first to eighth copper alloys of meeting the condition of (7), it is preferable to appropriately determine casting conditions, particularly a casting temperature and a cooling rate. Specifically, in terms of the casting temperature, it is preferable to determine it to be higher than a liquidus temperature of the corresponding copper alloy by 20 to 250° C. (more preferably 25 to 150° C.). In other words, the casting temperature is preferably determined in the following range: (liquidus temperature+20° C.)≦the casting temperature≦(liquidus temperature+250° C.), and more preferably (liquidus temperature+25° C.)≦the casting temperature≦(liquidus temperature+150° C.). In general, while being dependent on alloy components, the casting temperature is less than 1150° C., preferably 1100° C. and more preferably 1050° C. The lower side of the casting temperature is not particularly restricted as long as a molten metal is filled up to all the corners of a mold. However, as the casting is performed at a lower temperature, there shows a tendency that the grain is refined. It should be understood that these temperature conditions are varied according to the amount of each constituent element of an alloy.

BRIEF DESCRIPTION OF THE DRAWINGS

FIG. 1 is a photograph of an etched surface (cut surface) of a copper alloy No. 79 of an embodiment, wherein FIG. 1A illustrates a macrostructure, and FIG. 1B illustrates a microstructure;

FIG. 2 is a photograph of an etched surface (cut surface) of a copper alloy No. 228 of a comparative example, wherein FIG. 2A illustrates a macrostructure, and FIG. 2B illustrates a microstructure;

DESCRIPTION OF THE EMBODIMENTS

As an embodiment, copper alloy Nos. 1 to 92 of compositions shown in Tables 1 to 8 were obtained as castings A, B, C, D, E and F, and a plastic worked material G Further, as a comparative example, copper alloy Nos. 201 to 236 of compositions shown in Tables 9 to 12 were obtained as castings A1, B1, C1, D1, E1, F1 and G1, and a plastic worked material G2.

The castings A (copper alloy Nos. 1 to 46) and the castings A1 (copper alloy Nos. 201 to 214) were rods having a diameter of 40 mm, which were continuously cast at a low speed (0.3 m/min.) using a casting apparatus where a horizontal continuous casting machine was attached to a melting furnace (melting capacity of 60 kg). Further, the castings B (copper alloy Nos. 47 to 52) and the castings B1 (copper alloy Nos. 217 and 218) were rods having a diameter of 8 mm, which were continuously cast at a low speed (1 m/min.) using the casting apparatus where the horizontal continuous casting machine was attached to the melting furnace (melting capacity of 60 kg). In either case, the casting was continuously performed using a graphite mold while adjusting and adding an addition element to become a predetermined component if necessary. Further, in the casting process of the castings A, B, A1 and B1, when the casting was performed, Zr was added in a form of a Cu—Zn—Zr alloy (containing Zr of 3 mass %) and simultaneously a casting temperature was set to be higher than a liquidus temperature of a constituent material of the corresponding casting by 100° C. In addition, the castings A1 (copper alloy Nos. 215 and 216) were horizontal continuous rods having a diameter of 40 mm which were put on the market (wherein No. 215 corresponds to CAC406C).

Figure 6:
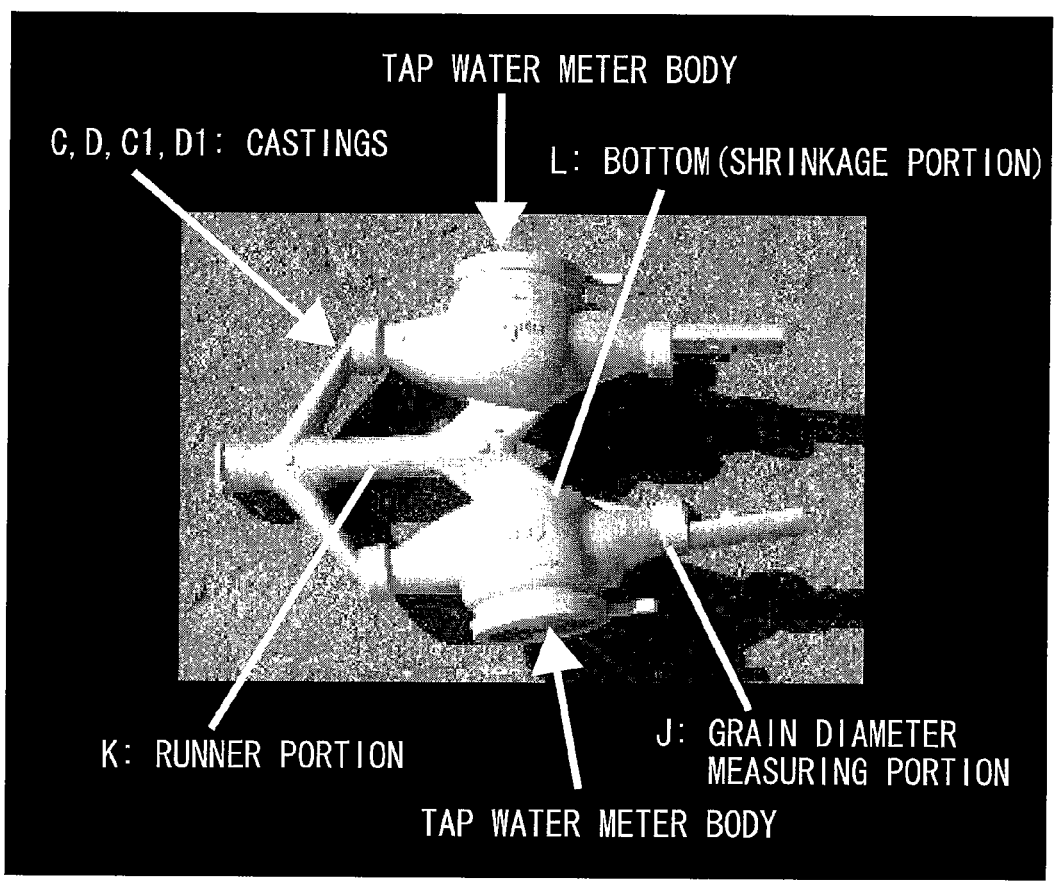
FIG. 6 is a perspective view showing a casting C, D, C1 or D1 (body of a tap water meter)

Any one of the castings C (copper alloy Nos. 53 to 73), the castings D (copper alloy Nos. 74 to 78), the castings C1(copper alloy Nos. 219 to 224) and the castings D1(copper alloy Nos. 225 and 226) was obtained by low-pressure casting (molten metal temperature of 1005° C.±5° C., pressure of 390 mbar, pressurizing time of 4.5 seconds, and holding time of 8 seconds) of actual operation, and was a casting product having the body of a paired tap water meter as shown in FIG. 6. Further, the castings C and C1 were cast using a metal mold, while the castings D and D1 were cast using sand mold.

The castings E (copper alloy Nos. 79 to 90) and the castings E1 (copper alloy Nos. 228 to 233) were ingots of a cylindrical shape (diameter of 40 mm and length of 280 mm), each of which was obtained by melting a raw material in an electric furnace and then casting the molten metal into a metal mold preheated at a temperature of 200° C.

The casting F (No. 91) and the casting F1 (No. 234) were large-size castings (ingots having a thickness of 190 mm, a width of 900 mm and a length of 3500 mm) obtained by low-pressure casting of actual operation.

The plastic-worked material G (copper alloy No. 92) was a rod having a diameter of 100 mm which was obtained by hot extruding an ingot (billet having a diameter of 240 mm). Any one of the plastic-worked materials G1 (copper alloy Nos. 235 and 236) was an extruded-drawn rod (having a diameter of 40 mm) which was put on the market. Further, No. 235 corresponded to JIS C3604, and No. 236 corresponded to JIS C3711. Also, in the following description, the castings A, B, C, D, E and F, and the plastic worked material G may be referred to as an "embodiment material," while the castings A1, B1, C1, D1, E1, F1 and G1, and the plastic worked material G2 may be referred to as a "comparative example material."

And, No. 10 test specimens specified in JIS Z 2201 were sampled from the embodiment materials A, B, C, D, E, F and G, and the comparative example materials A1, B1, C1, D1, E1, F1, G1 and G2. In terms of the test specimens, a tensile test was performed by an Amsler universal testing machine, and tensile strength (N/mm$^2$), 0.2% yield strength (N/mm$^2$), elongation (%) and fatigue strength (N/mm$^2$) were measured. The results were as shown in Tables 13 to 18, and it was identified that the embodiment materials were excellent in mechanical properties such as tensile strength etc. Further, in terms of the castings C, D, C1 and D1, the test specimens were sampled from a runner portion K shown in FIG. 6.

Further, in order to compare and identify machinability of the embodiment materials and the comparative example materials, the following cutting test was performed to measure a cutting main component of force N.

Specifically, outer circumferential surfaces of specimens sampled from the embodiment materials A, B, E and G and the comparative example materials A1, B1, E1 and G1 were dry-cut by a lathe equipped with a point nose straight tool (having a rake angle of −6° and a nose radius of 0.4 mm) under the conditions: a cutting speed of 80 m/min, a cutting depth of 1.5 mm and a feed speed of 0.11 mm/rev., and under the conditions: a cutting speed from 160 m/min, a cutting depth of 1.5 mm and a feed speed of 0.11 mm/rev., measured by a three-component force dynamometer attached to the bite, and calculated in terms of the cutting main component of force. The results were as shown in Tables 13 to 18.

Figure 5:
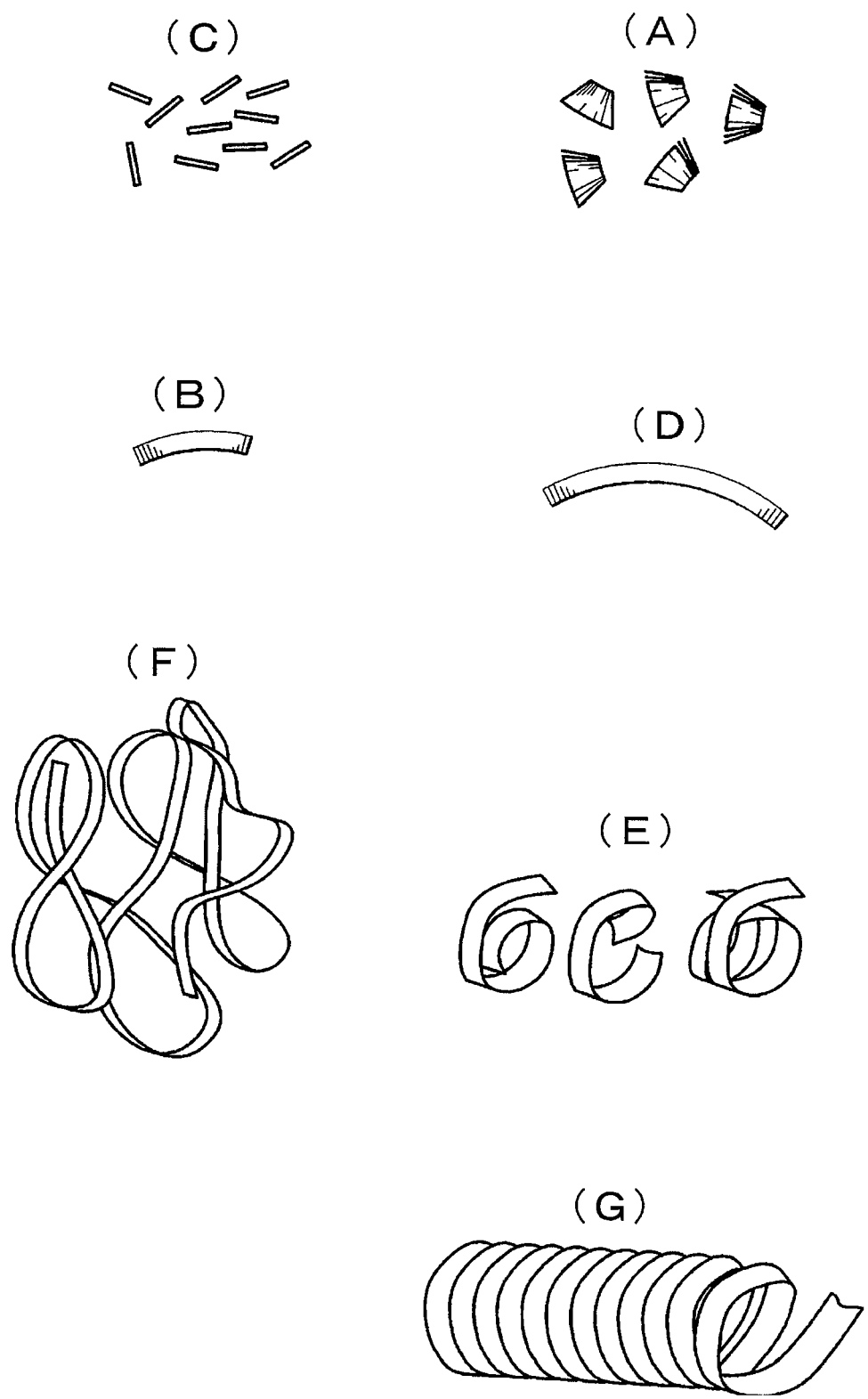
FIG. 5 is a perspective view showing a form of a cut chip generated in a cutting test.

Further, states of cut chips generated in the cutting test were observed. The chips were classified into seven by their shapes: (a) trapezoidal or triangular small segment shape (FIG. 5(A)), (b) tape shape having a length of 25 mm or less (FIG. 5(B)), (c) acicular shape (FIG. 5(C)), (d) tape shape having a length of 75 mm or less (excluding (b)) (FIG. 5(D)), (e) spiral shape having three turns (rolls) or less (FIG. 5(E)), (f) tape shape exceeding a length of 75 mm (FIG. 5(F)), and (g) spiral shape exceeding three turns (FIG. 5(G)), and subjected to evaluation of the machinability. The results were shown in Tables 13 to 18. In these Tables, the cut chip whose shape belongs to (a) was represented by the symbol "◉", (b) by the symbol "○", (c) by the symbol "●", (d) by the symbol "∇", (e) by the symbol "△", (f) by the symbol "x", and (g) by the symbol "xx". When the cut chips took the shapes of (f) and (g), handling (collection or reuse) of the cut chips become difficult, as well as the good cutting could not be carried out because troubles that the cut chips stuck to the bite damaged a cutting surface or the like were generated. When the cut chips took the shapes of (d) and (e), the great troubles as in (f) and (g) were not generated, but the handling of the cut chips was not easy as well, and when the cutting was continuously performed, the generated chips can be stuck to the bite or damage the cut surface or the like. In contrast, when the cut chips took the shapes of (a) to (c), the above-mentioned troubles were not generated, and the handling of the cut chips was easy in that a volume was not increased as in (f) and (g) (that is, because the volume was not increased). However, in regard to (c), the cut chips often slipped into a sliding surface of a machine tool such as a lathe to generate a mechanical obstacle according to the cutting conditions, or accompanied dangers, for example, of pricking fingers or eyes of an operator. Thus, in regard to evaluation of the machinability, (a) was the best, (b) was second best, (c) was good, (d) was slightly good, (e) was only acceptable, (f) was inadequate, and (g) was most inadequate. It was identified from the cutting main component of force and cutting chip shape that the embodiment materials were excellent.

Further, the following wear test was performed in order to compare and identify wear resistance of the embodiment materials and that of the comparative example materials.

First, annular test specimens having an outer diameter of 32 mm and a thickness of 10 mm (length of an axis direction) were obtained from the embodiment materials A and E and the comparative example materials A1, E1 and G1 by performing cutting and boring on these materials. Sequentially, in the state where each test specimen was fitted into a rotational shaft and simultaneously an SUS304 roll (having an outer diameter of 48 mm) come into rolling contact with the outer circumferential surface of the annular test specimen under a load of 50 kg, the rotational shaft was rotated at 209 rpm while multi-oil was dropped down the outer circumferential surface of the test specimen. And, when the number of rotations amounted to 100,000 times, the rotation of the test specimen was stopped. A weight difference between before and after the rotation, namely a wear loss (mg) was measured. As this wear loss become small, the copper alloy is excellent in wear resistance. The results were as shown in Tables 19, 20, 22, 23 and 24. It was identified that the embodiment materials were excellent in wear resistance and slidability.

Further, the following erosion corrosion tests I to III, dezincification corrosion test specified in "ISO 6509," and stress corrosion crack test specified in "JIS H3250" were performed in order to compare and identify corrosion resistance of the embodiment materials and that of the comparative example materials.

That is, in the erosion corrosion tests I to III, a erosion corrosion test was performed by striking specimens sampled from castings of the embodiment materials A, C, D and E and the comparative example materials A1, E1 and G1 with a test melting (30° C.) at a flow rate of 11 nm/sec in a direction perpendicular to the axes of the specimens from a nozzle having a diameter of 1.9 mm. Then, a mass loss (mg/cm$^2$) was measured after a predetermined time T had lapsed. As the test melting, a saline melting of 3% was used for the test I, a mixed saline melting of mixing $CuCl_2.2H_2O$ (0.13 g/L) with the saline melting of 3% was used for the test II, and a mixed melting of adding a very small amount of hydrochloric acid (HCl) to sodium hypochlorite (NaClO) was used for the test III. The mass loss was an amount per 1 cm$^2$ (mg/cm$^2$) extracting a specimen weight after impacting the test melting for the T time from a specimen weight before initiating the test, and the impact time was set as T=96 in any one of the tests I to III. The results of the erosion corrosion tests I to III were as shown in Tables 19 to 24.

Further, in the dezincification corrosion test of "ISO 6509," specimens sampled from castings of the embodiment materials A, C, D and E and the comparative example materials A1, E1 and G1 were attached to phenolic resins in the state where exposed specimen surfaces were perpendicular to an extension direction, and then the specimen surfaces were polished by an emery paper of up to No. 1200. The polished specimens were dried after ultrasonic cleaning in pure water. The corrosion test specimens obtained in this manner were immersed into a water melting of 1.0% copper (II) chloride dehydrate ($CuCl_2.2H_2O$), maintained for 24 hours under a temperature condition of 75° C. and withdrawn from the water melting. Then, the maximum value of dezincification corrosion depth, namely the maximum dezincification corrosion depth (μm), was measured. The results were as shown in Tables 19 to 24.

Further, in the stress corrosion crack test of "JIS H3250," plate-like specimens (width of 10 mm, length of 60 mm and thickness of 5 mm) sampled from the castings B and B1 were bent in a V shape of 45° (curved portion radius of 5 mm) (in order to apply tensile residual stress) and subjected to degreasing and drying. In this state, the specimens were maintained in an ammonia atmosphere (25°) in a desiccator in which ammonia water of 12.5% (diluting ammonia with the same amount of pure water) was contained. And at a time point when a predetermined holding time (exposure time) had lapsed, the specimens were taken out from the desiccator and cleaned with sulfuric acid of 10%. In this state, it was observed with a microscope (10-power) whether there was any crack in the corresponding specimen or not, thereby the specimens were evaluated. The results were as shown in Tables 21 and 23. In the corresponding Table, the specimen whose crack was shown when the holding time of 8 hours had lapsed in the ammonia atmosphere, but clearly shown when 24 hours had lapsed was represented by the symbol "Δ", and the specimen whose crack was never shown when 24 hours had lapsed was represented by the symbol "○". It was identified from these results of the corrosion resistance test that the embodiment materials were excellent in corrosion resistance.

Further, the following cold compression test was performed in order to compare and evaluate cold workability of the embodiment materials and that of the comparative example materials.

That is, from the castings A, B and A1, cylindrical specimens having a diameter 5 mm and a length of 7.5 mm were cut and sampled by a lathe, and subjected to compression by an Amsler universal testing machine and evaluation of cold compression workability by existence or non-existence of a crack according to relation with compressibility (work rate). The results were as shown in Tables 19, 20, 21 and 23. In these Tables, the specimen that generated the crack at the compressibility of 30% was considered to be bad in cold compression workability, thus being represented by the symbol "x", the specimen where the crack was not generated at the compressibility of 40% was considered to be excellent in cold compression workability, thus being represented by the symbol "○", and the specimen where the crack was not generated at the compressibility of 30% but it was generated at the compressibility of 40% was considered to be good in cold compression workability, thus being represented by the symbol "Δ". The good or bad of the cold compression workability could be evaluated by the good or bad of caulking workability. When the evaluation was given by the symbol "○", it was possible to perform caulking with ease and high precision. When given by the symbol "Δ", ordinary caulking was possible. When given by the symbol "x", it was impossible to perform proper caulking. It was identified that, among the embodiment materials, some were represented by the symbol "Δ", most of which were largely represented by the symbol "○", and thus the embodiment materials were excellent in cold compression workability, i.e. caulking workability.

Further, the following high-temperature compression test was performed in order to compare and evaluate hot forgeability of the embodiment materials and that of the comparative example materials. From the castings A, E and E1 and the plastic worked material G1, cylindrical specimens having a diameter of 15 mm and a height of 25 mm were sampled using a lathe. These specimens were maintained for 30 minutes at 700° C., and then subjected to hot compression after changing a work rate and evaluation of the hot forgeability from relation between the work rate and crack. The results were as shown in Tables 20, 22 and 24. It was identified that the embodiment materials were excellent in hot forgeability. In these Tables, the specimen where the crack was not generated at the work rate of 80% was considered to be excellent in hot forgeability, thus being represented by the symbol "○", the specimen where the crack was slightly generated at the work rate of 80%, but not generated at the work rate of 65% was considered to be good in hot forgeability, thus being represented by the symbol "Δ", and the specimen where the crack was remarkably generated at the work rate of 65% was considered to be bad in hot forgeability, thus being represented by the symbol "x".

Further, in order to compare and identify cold drawability with respect to the embodiment materials and the comparative example materials, the cold drawability was evaluated on the basis of the following. The rod-like castings B and B1 (diameter of 8 mm) were subjected to cold drawing. One capable of being cold-drawn without generating a crack up to the diameter of 6.4 mm by a single drawing (work rate of 36%) was evaluated to be excellent in cold drawability, one capable of being cold-drawn without generating a crack up to the diameter of 7.0 mm by a single drawing (work rate of 23.4%) was evaluated to be normal in cold drawability, and one capable of being cold-drawn with generating a crack when the cold drawing was performed once up to the diameter of 7.0 mm was evaluated to be bad in cold drawability. The results were as shown in Tables 21 and 23. One that was evaluated to be excellent in cold drawability was represented by the symbol "○", one that was evaluated to be normal in cold drawability was represented by the symbol "Δ", and one that was evaluated to be bad in cold drawability was represented by the symbol "x". As understood from Tables 21 and 23, it was identified that the embodiment materials were excellent in cold drawability compared with the comparative example materials.

Further, castability was evaluated with respect to the embodiment materials and the comparative example materials.

First, in terms of the castings B and B1, superiority or inferiority of the castability was evaluated by performing the following castability evaluation test. That is, in the castability evaluation test, when the casting B was obtained in the embodiment while a casting speed was varied in two steps, high and low, of 2 m/min and 1 m/min, (or when the casting B1 was obtained in the comparative example), the superiority or inferiority of the castability was evaluated by the high or low in the casting speed at which the wire free of defects was obtained by continuously casting a wire (rod) having a diameter of 8 mm under the same condition and apparatus as those employed to obtain the casting B in the embodiment (or to obtain the casting B1 in the comparative example). The results were as shown in Tables 21 and 23. One where the defect-free wire was obtained at the high casting speed of 2 m/min was considered to be excellent in castability, thus being represented by the symbol "○". One where the defect-free wire was not obtained at the high casting speed but it was obtained at the low casting speed of 1 m/min was considered to be normal in castability, thus being represented by the symbol "Δ". One where the defect-free cast wire B-1 was not obtained even at the low casting speed (1 m/min) was considered to be bad in castability, thus being represented by the symbol "x".

Figure 7:
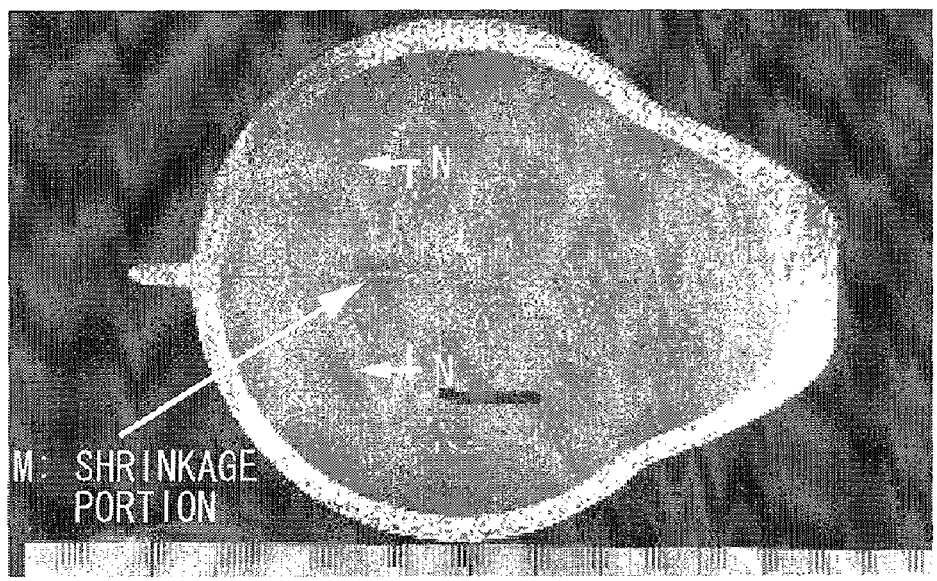
FIG. 7 is a plan view cutting and showing a bottom of the casting C, D, C1 or D1 (body of the tap water meter) shown in FIG. 6.
Figure 8:
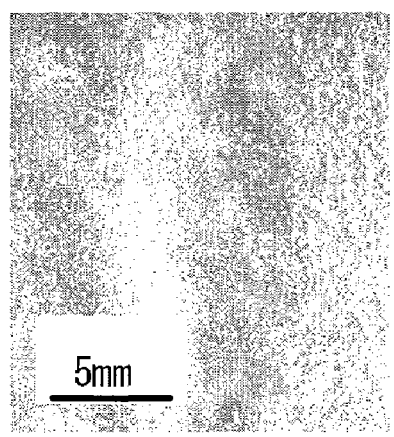
FIG. 8 is a magnified plan view of an inside important portion (a shrinkage portion corresponding to an M portion of FIG. 7) of a casting C, a copper alloy No. 72, of an embodiment.
Figure 9:
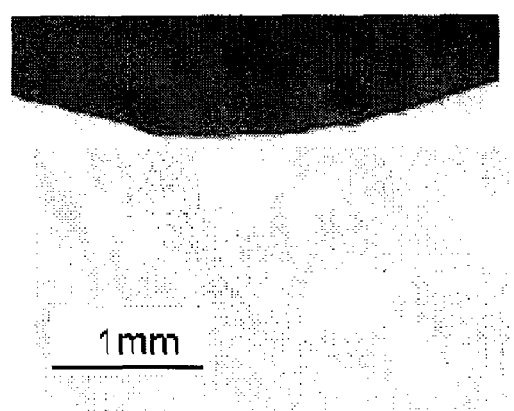
FIG. 9 is a cross-sectional view (corresponding to a cross-section view taken along line N-N of FIG. 7) of an important portion of a casting C, a copper alloy No. 72, of an embodiment.
Figure 10:
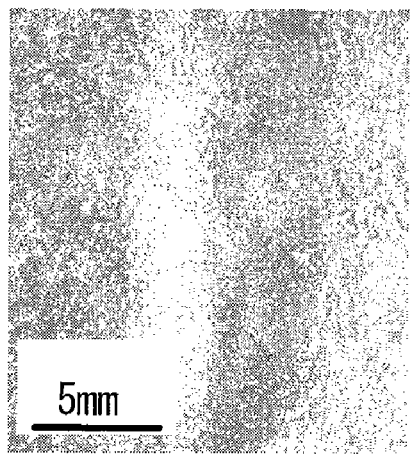
FIG. 10 is a magnified plan view of an inside important portion (a shrinkage portion corresponding to an M portion of FIG. 7) of a casting C, a copper alloy No. 73, of an embodiment.
Figure 11:
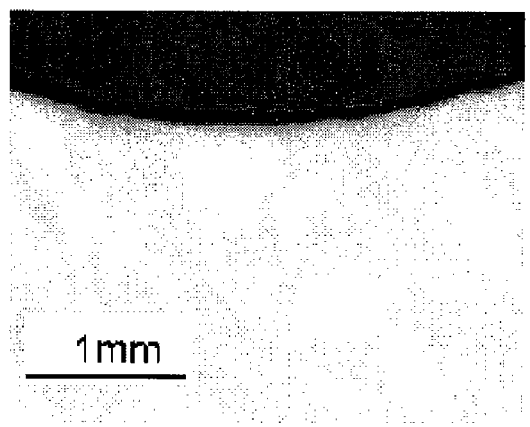
FIG. 11 is a cross-sectional view (corresponding to a cross-section view taken along line N-N of FIG. 7) of an important portion of a casting C, a copper alloy No. 73, of an embodiment.
Figure 12:
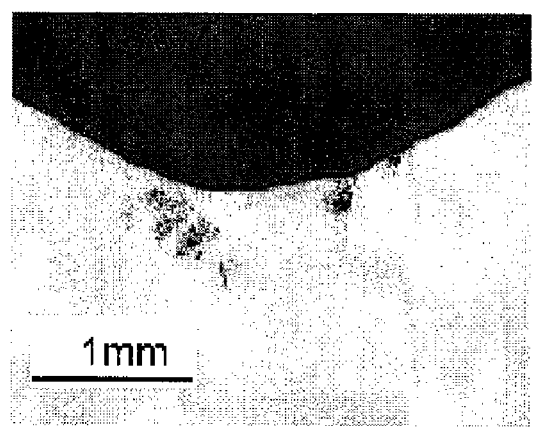
FIG. 12 is a magnified plan view of an inside important portion (a shrinkage portion corresponding to an M portion of FIG. 7) of a casting C1, a copper alloy No. 224, of a comparative example.
Figure 13:
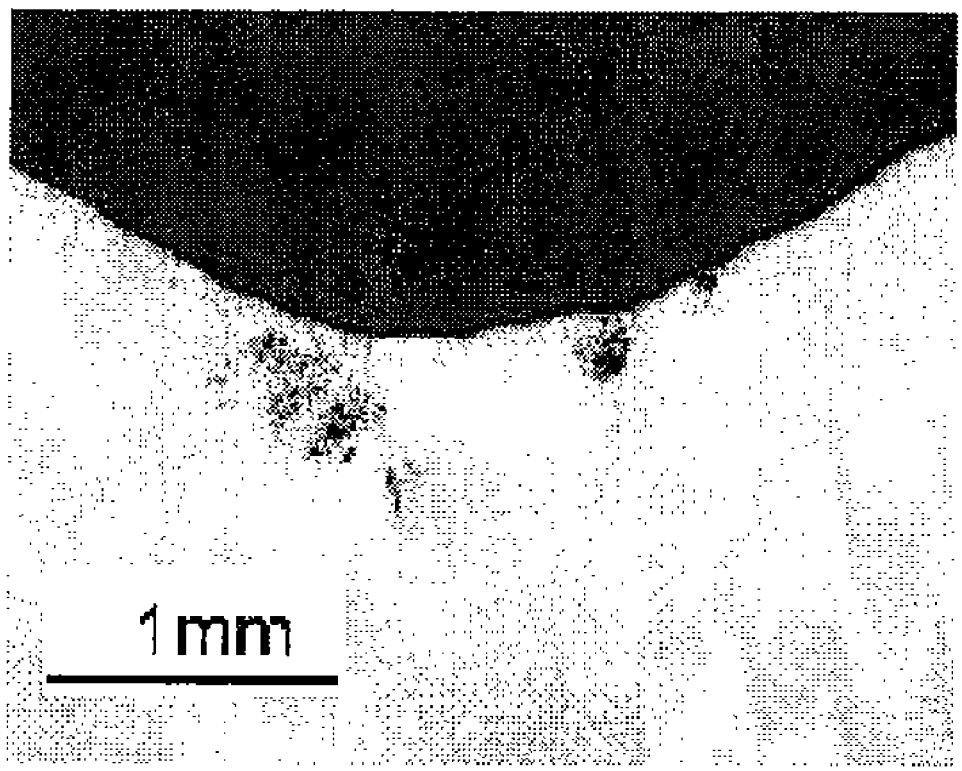
FIG. 13 is a cross-sectional view (corresponding to a cross-section view taken along line N-N of FIG. 7) of an important portion of a casting C1, a copper alloy No. 224, of an embodiment.

Second, a bottom L (see FIG. 6) of the casting C or C1 was cut off, and a shrinkage portion M (see FIG. 7) inside the cut-off portion was observed. The castability was evaluated by existence or non-existence of defects and a depth of shrinkage. The results were as shown in Tables 21 to 23. In these Tables, one where no defect was present in the shrinkage portion M and the shrinkage was shallow was considered to be excellent in castability, thus being represented by the symbol "○". Further, one where no clear defect was present in the shrinkage portion M and the shrinkage was not very deep was considered to be good in castability, thus being represented by the symbol "Δ". However, one where clear defects were present in the shrinkage portion M or the shrinkage was deep was considered to be bad in castability, thus being represented by the symbol "x". Examples of the shrinkage portion M are shown in FIGS. 8 to 13. That is, FIG. 8 is a cross-sectional view of the shrinkage portion M in the copper alloy No. 72 of the embodiment, and FIG. 9 is a magnified plan view of the corresponding shrinkage portion M. Further, FIG. 10 is a cross-sectional view of the shrinkage portion M in the copper alloy No. 73 of the embodiment, and FIG. 11 is a magnified plan view of the corresponding shrinkage portion M. FIG. 12 is a cross-sectional view of the shrinkage portion M in the copper alloy No. 224 of the comparative example, and FIG. 13 is a magnified plan view of the corresponding shrinkage portion M. As can be seen from FIGS. 8 to 13, the surfaces of the shrinkage portions M in the copper alloy Nos. 72 and 73 are very smooth and free of defects, while in the copper alloy No. 224, clear defects are present in the shrinkage portion M and the depth of shrinkage is deep. Further, since the copper alloy No. 224 has the almost same composition as those of the copper alloy Nos. 72 and 73 except that Zr is not contained, it can be understood from FIGS. 8 to 13 that grain refinement is facilitated by co-addition of Zr and P, and thus the castability is improved.

Third, the following semi-solid metal castability test was performed in order to compare and evaluate the embodiment materials and the comparative example materials with respect to semi-solid metal castability.

Figure 3:
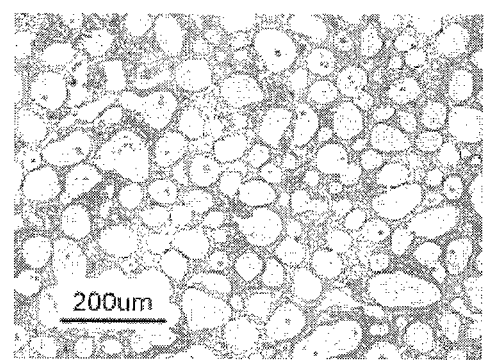
FIG. 3 is a photomicrograph of a semi-melted solidified state in a semi-solid metal castability test of a copper alloy No. 4 of an embodiment.
Figure 4:
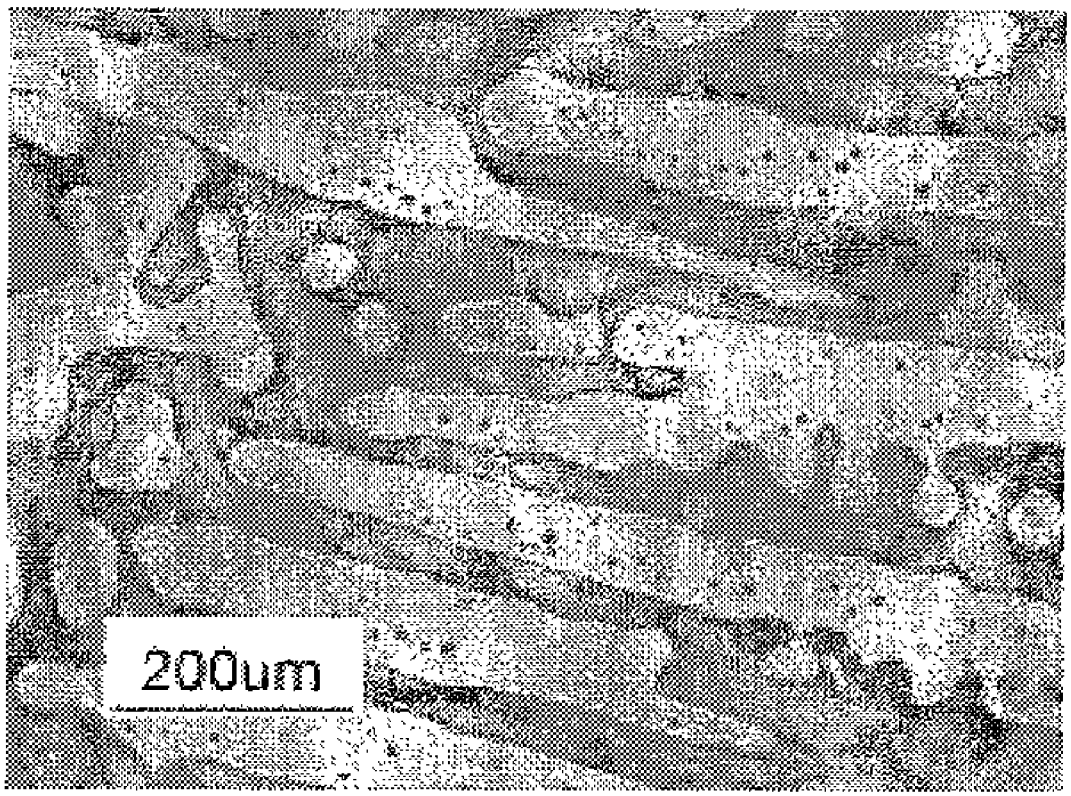
FIG. 4 is a photomicrograph of a semi-melted solidified state in a semi-solid metal castability test of a copper alloy No. 202 of a comparative example.

That is, raw materials used when the castings A, A1 and E1 were cast were charged into a crucible, heated up to a semi-melted state (solid phase fraction of about 60%), maintained for 5 minutes at that temperature, and subjected to quenching (water cooling). And, the semi-solid metal castability was evaluated by investigating the shape of a solid phase in the semi-melted state. The results were as shown in Tables 19, 23 and 24. It was identified that the embodiment materials met the conditions of (14) and (15) and were excellent in semi-solid metal castability. In these Tables, one where an average grain diameter of the corresponding solid phase was 150 μm or less, or an average of the maximum length of a grain was 300 μm or less was evaluated to be excellent in semi-solid metal castability, thus being represented by the symbol "○". One where a grain of the corresponding solid phase did not meet these conditions, but a remarkable dendrite network was not formed was evaluated to have good semi-solid metal castability enough to be industrially satisfactory, thus being represented by the symbol "Δ". One where a dendrite network was formed was evaluated to be bad in semi-solid metal castability, being represented by the symbol "x". Examples where the embodiment materials meet the conditions of (14) and (15) are shown. That is, FIG. 3 is a photomicrograph of a semi-melted solidified state in the semi-solid metal castability test of the copper alloy No. 4, the embodiment material, which clearly meets the conditions of (14) and (15). Further, FIG. 4 is a photomicrograph of a semi-melted solidified state in the semi-solid metal castability test of the copper alloy No. 202, the comparative example material, which does not meet the conditions of (14) and (15).

Further, with regard to the embodiment materials A to G and the comparative example materials A1 to G1, average grain diameters (μm) were measured when they were melted and solidified. In other words, in the state of cutting the embodiment materials and the comparative example materials and etching the cut surfaces with nitric acid, average diameters of grains (average grain diameters) were measured in macrostructures emerged on the etched surfaces. Further, with regard to the castings C, D, C1 and D1, in the state of cutting an inflow outlet J (see FIG. 6) of a tap water meter body and etching its cut surface with nitric acid, an average diameter of a grain on the etched surface was measured in the same manner as set forth above. This measurement was based on a comparison method of an average grain size test of a drawn copper product of JIS H0501. The cut surface was etched with nitric acid. Then, one whose grain diameter exceeded 0.5 mm was observed with naked eyes, one whose grain diameter was less than 0.5 mm was observed by 7.5 power magnification, and one whose grain diameter was less than 0.1 mm was etched with a mixed melting of hydrogen peroxide and ammonia water, and then observed by 75 power magnification by an optical microscope. The results were as shown in Tables 13 to 18. Any one of the embodiment materials was to meet the condition of (7). Further, in terms of the comparative example materials, it was identified that they all had the primary crystal of a phase when melted and solidified.

Figure 1:
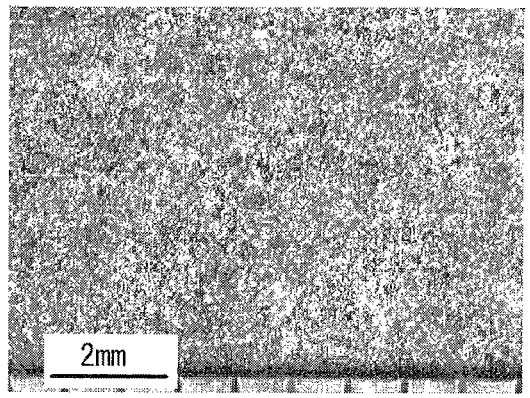
Figure 1:
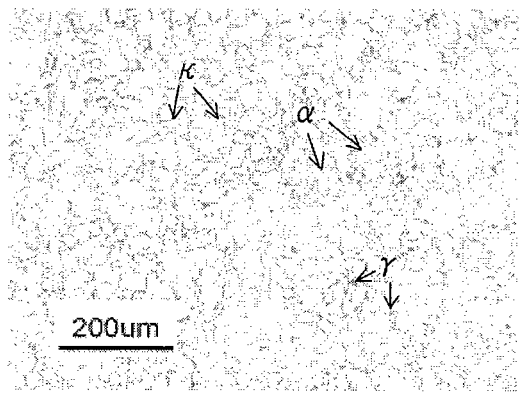
Figure 2:
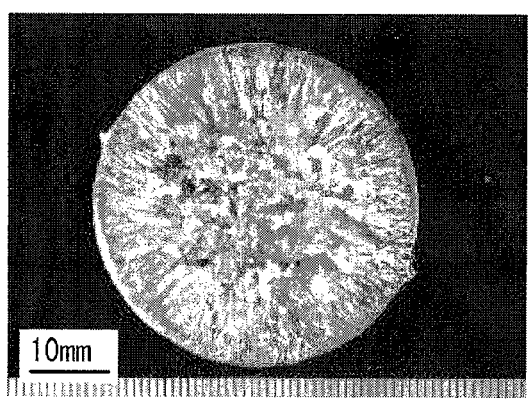
Figure 2:
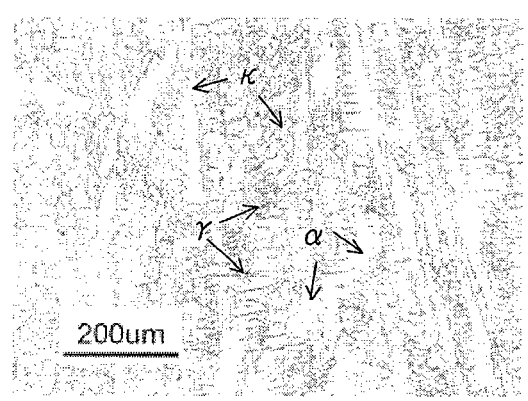

Further, it was identified that the embodiment materials met the conditions of (12) and (13). Their examples are shown in FIGS. 1 and 2. FIG. 1 is a macrostructure photograph of the copper alloy No. 79, the embodiment material (FIG. 1A) and a microstructure photograph (FIG. 1B). FIG. 2 is a macrostructure photograph of the copper alloy No. 228, the comparative example material (FIG. 2A) and a microstructure photograph (FIG. 2B). As being clear in FIGS. 1 and 2, it should be understood that the comparative example material No. 228 does not meet the conditions of (12) and (13), while the embodiment material No. 79 meets the conditions of (12) and (13).

It was identified from the foregoing that the embodiment materials were sharply improved in machinability, mechanical properties (strength, elongation etc.), wear resistance, castability, semi-solid metal castability, cold compression workability, hot forgeability and corrosion resistance by having each constituent element contained in the aforementioned range and meeting the conditions of (1) to (7) (with regard to the fifth to eighth copper alloys, additionally, the condition of (8)), as compared with the comparative example materials which failed to meet at least some of these conditions. Further, it was identified that the improvement of these properties could be effectively facilitated by meeting the condition of (10) to (15) in addition to the foregoing conditions (with regard to the fifth to eighth copper alloys, additionally, the conditions of (9) and (16)). It was identified that the above fact were equally true of the large-size casting F (No. 91), and the grain refinement effect by the co-addition of Zr and P and the resultant effect of the property improvement were guaranteed without a damage. Further, with regard to the large-size casting (No. 234) having the almost same composition as the copper alloy No. 91 except for not containing Zr, these effects were not present, and a difference from the small-size castings was clear.

Further, with regard to the castings C, C1 and D1 containing Pb, a lead leakage test was performed based on "JTS S3200-7:2004 Water Supply Equipment—Performance Tests for Leachability." That is, in this test, water (quality: pH 7.0±0.1, hardness: 45±5 mg/L, alkalinity: 35±5 mg/L, residual chlorine: 0.3±0.1 mg/L) where pH was adjusted, with a sodium hydroxide melting, to water adding a sodium hypochlorite melting, a sodium hydrogen carbonate melting and a calcium chloride melting at an proper amount was used as a leaching solution, and the castings C, C1 and D1 were subjected to predetermined cleaning and conditioning, and then a hollow portion of the corresponding castings C, C1 or D1 (namely, a tap water meter body itself, see FIG. 6) was filled with the leaching solution of 23° C. and sealed, and then the castings were left at rest for 16 hours with the solution retained at 23° C., and then an exudation amount (mg/L) of Pb contained the leaching solution was measured. The results were as shown in Tables 21, 23 and 24. It was identified that the exudation amount of Pb was extremely small in the embodiment materials, and the castings were possible to be used as the water-contact fittings such as the tap water meter without any problem.

Further, a runner portion K (see FIG. 6) was sampled from the casting C of the copper alloy No. 54, and a copper alloy was cast using the sampled runner portion as a raw material (Zr: 0.0063 mass %). That is, the corresponding runner portion K was remelted under a charcoal cover at 970° C., maintained for 5 minutes, and under the anticipation that an amount of oxidation loss of Zr when melted would amount to 0.001 mass %, further added a Cu—Zn—Zr alloy containing 3 mass % Zr as much as the amount of oxidation loss of Zr, then being cast into a metal mold. As a result, in the obtained casting, a content of Zr was almost equal (0.0061 mass %) to that of the raw material, the copper alloy No. 54, and an average grain diameter, that was measured, was 25 μm that was almost equal to that of the original copper alloy No. 54. It was identified from the above fact that the copper alloy of the present invention was capable of effectively using surplus or unnecessary portions such as the runner portion K generated in its casting as a recycling raw material without damaging the grain refinement effect. Therefore, it is possible to use the surplus or unnecessary portions such as the runner portion K as a supplementary raw material charged under the continuous operation, and to very efficiently or economically carry out the continuous operation.

The copper alloy of the present invention is subjected to the grain refinement in the melt-solidification step, so that it can resist the shrinkage when solidified and decrease the generation of the casting crack. Further, in terms of the hole or porosity generated in the process of solidification, they escape outside with ease, so that the sound casting free from the casting defects is obtained (because the casting defect such as the porosity is not present, and because the dendrite network is not formed, the casting has the smooth surface and the shrinkage cavity as shallow as possible). Therefore, according to the present invention, it is possible to provide the casting having very abundant practical use or the plastic worked material performing plastic working on the casting.

Further, the grains crystallized in the process of solidification takes the shape where the arm is divided, preferably such as the circular shape, elliptical shape, polygonal shape and criss cross shape rather than the branch-like structure which is typical for cast structure. As such, the fluidity of the molten metal is improved, so that the molten metal can spread to all the corners of the mold although the mold has a thin thickness and a complicated shape.

The copper alloy of the present invention can foster sharp improvement of the machinability, strength, wear resistance, slidability and wear resistance exerted by the constituent elements by means of the grain refinement and the uniform distribution of the phases (K and γ phases generated by Si) except the α phase or the Pb particle, and can be properly, practically used as water-contact fitting used in contact with tap water at all times or temporally (for example, water faucet fittings of water supply piping, valve cocks, joints, flanges, water faucet fittings, residential facilities and drain mechanisms, connecting fittings, water heater parts etc.), frictional engagement member performing relative movement in contact with the other member (rotational shaft etc.) at all times or temporally (for example, bearing, gear, cylinder, bearing retainer, impeller, valve, open-close valve, pumps parts, bearings etc.) or pressure sensor, temperature sensor, connector, compressor part, scroll compressor part, high-pressure valve, air conditioner value and open-close value, carburetor, cable fixture, mobile phone antenna part, terminal or these constituent members.

Further, according to the method of the present invention, the grain refinement can be realized by the co-addition effect of Zr and P without generating any problem caused by addition of Zr in the form of the oxide and/or sulfide, thereby being capable of casting the copper alloy casting in an efficient, favorable manner.

TABLE 1

| | Copper Alloy | | Alloy Composition (mass %) | | | | | Impurity | |
|---|---|---|---|---|---|---|---|---|---|
| | No. | Type | Cu | Zn | Si | Zr | P | Pb | Fe | Ni |
| Embodiment | 1 | A | 76.2 | 20.68 | 3.05 | 0.0007 | 0.07 | | | |
| | 2 | A | 75.8 | 21.10 | 3.03 | 0.0018 | 0.07 | | | |
| | 3 | A | 76.1 | 20.80 | 3.03 | 0.0058 | 0.06 | | | |
| | 4 | A | 75.8 | 21.09 | 3.03 | 0.0094 | 0.07 | | | |
| | 5 | A | 76.4 | 20.49 | 3.04 | 0.014 | 0.06 | | | |
| | 6 | A | 76.6 | 20.20 | 3.1 | 0.018 | 0.08 | | | |
| | 7 | A | 76 | 20.84 | 3.04 | 0.028 | 0.09 | | | |
| | 8 | A | 76 | 20.83 | 3.04 | 0.037 | 0.09 | | | |
| | 9 | A | 76.1 | 20.79 | 3.02 | 0.003 | 0.09 | | | |
| | 10 | A | 74.5 | 22.60 | 2.8 | 0.01 | 0.09 | | | |

TABLE 1-continued

| Copper Alloy | | Alloy Composition (mass %) | | | | | Impurity | |
|---|---|---|---|---|---|---|---|---|
| No. | Type | Cu | Zn | Si | Zr | P | Pb | Fe | Ni |
| 11 | A | 77.2 | 19.42 | 3.3 | 0.009 | 0.07 | | | |
| 12 | A | 81.6 | 14.47 | 3.85 | 0.017 | 0.06 | | | |
| 13 | A | 79.2 | 18.00 | 2.7 | 0.021 | 0.08 | | | |
| 14 | A | 78 | 18.88 | 3.04 | 0.009 | 0.07 | | | |
| 15 | A | 75.8 | 21.01 | 3.03 | 0.017 | 0.08 | | | 0.06 |
| 16 | A | 75.7 | 21.06 | 3.05 | 0.016 | 0.09 | | 0.04 | 0.04 |
| 17 | A | 75.8 | 21.02 | 3.06 | 0.017 | 0.08 | | 0.018 | 0.009 |
| 18 | A | 76 | 20.87 | 3.05 | 0.009 | 0.07 | 0.002 | | |
| 19 | A | 76 | 20.89 | 3.03 | 0.009 | 0.07 | 0.006 | | |
| 20 | A | 76.1 | 20.76 | 3.05 | 0.009 | 0.07 | 0.012 | | |
| 21 | A | 76.3 | 20.55 | 3.05 | 0.01 | 0.07 | 0.018 | | |
| 22 | A | 76.3 | 20.55 | 3.03 | 0.009 | 0.07 | 0.04 | | |
| 23 | A | 76.2 | 20.59 | 3.05 | 0.009 | 0.07 | 0.08 | | |

TABLE 2

| | Copper Alloy | | Alloy Composition (mass %) | | | | | | | | | |
|---|---|---|---|---|---|---|---|---|---|---|---|---|
| | No. | Type | Cu | Zn | Si | Zr | P | Pb | Sn | Sb | Al | Mn | Mg |
| Embodiment | 24 | A | 76.2 | 20.50 | 3.04 | 0.009 | 0.07 | 0.18 | | | | | |
| | 25 | A | 76.1 | 20.49 | 3.02 | 0.008 | 0.07 | 0.31 | | | | | |
| | 26 | A | 78.2 | 18.66 | 3.05 | 0.009 | 0.07 | 0.01 | | | | | |
| | 27 | A | 78 | 18.85 | 3.05 | 0.009 | 0.07 | 0.018 | | | | | |
| | 28 | A | 78.1 | 18.65 | 3.04 | 0.008 | 0.08 | 0.12 | | | | | |
| | 29 | A | 78 | 18.59 | 3.04 | 0.008 | 0.08 | 0.28 | | | | | |
| | 30 | A | 73.2 | 23.90 | 2.75 | 0.008 | 0.07 | 0.07 | | | | | |
| | 31 | A | 73.2 | 23.85 | 2.76 | 0.009 | 0.08 | 0.1 | | | | | |
| | 32 | A | 78.8 | 17.39 | 3.7 | 0.009 | 0.08 | 0.018 | | | | | |
| | 33 | A | 77.2 | 19.30 | 3.4 | 0.009 | 0.07 | 0.019 | | | | | |
| | 34 | A | 76.8 | 19.75 | 3.07 | 0.009 | 0.07 | | 0.3 | | | | |
| | 35 | A | 77.2 | 19.08 | 3.14 | 0.008 | 0.07 | | 0.5 | | | | |
| | 36 | A | 76.8 | 19.98 | 3.04 | 0.009 | 0.06 | | 0.11 | | | | |
| | 37 | A | 78.1 | 17.59 | 3.12 | 0.014 | 0.08 | | 1.1 | | | | |
| | 38 | A | 72.5 | 20.39 | 3.95 | 0.012 | 0.15 | | | | 0.3 | 2.7 | |
| | 39 | A | 76 | 18.20 | 3.68 | 0.016 | 0.1 | | | | 1.1 | 0.9 | |
| | 40 | A | 77.5 | 17.95 | 3.13 | 0.022 | 0.1 | | | | 1.3 | | |
| | 41 | A | 76.8 | 19.91 | 3.2 | 0.0007 | 0.08 | | | | | | 0.008 |
| | 42 | A | 76.5 | 20.26 | 3.12 | 0.0017 | 0.08 | | | | | | 0.035 |
| | 43 | A | 77.2 | 19.10 | 3.06 | 0.005 | 0.12 | 0.015 | 0.5 | | | | |
| | 44 | A | 76.5 | 20.08 | 3.03 | 0.011 | 0.09 | 0.09 | 0.2 | | | | |
| | 45 | A | 77.8 | 18.30 | 3.22 | 0.011 | 0.08 | | | 0.09 | 0.5 | | |
| | 46 | A | 74.5 | 18.05 | 3.98 | 0.0055 | 0.09 | | 0.4 | | 0.04 | 2.9 | 0.032 |

TABLE 3

| | Copper Alloy | | Alloy Composition (mass %) | | | | | | | | |
|---|---|---|---|---|---|---|---|---|---|---|---|
| | No. | Type | Cu | Zn | Si | Zr | P | Pb | Bi | Se | Sn |
| Embodiment | 47 | B | 76 | 20.88 | 3.04 | 0.009 | 0.07 | | | | |
| | 48 | B | 77.8 | 18.95 | 3.18 | 0.009 | 0.06 | | | | |
| | 49 | B | 76 | 20.89 | 3.01 | 0.038 | 0.06 | | | | |
| | 50 | B | 78.1 | 18.85 | 2.96 | 0.01 | 0.08 | | | | |
| | 51 | B | 76 | 20.86 | 3.05 | 0.009 | 0.06 | 0.018 | | | |
| | 52 | B | 77 | 19.38 | 3.05 | 0.009 | 0.06 | | | | 0.5 |
| | 53 | C | 76 | 20.88 | 3.05 | 0.0019 | 0.07 | | | | |
| | 54 | C | 76 | 20.93 | 3 | 0.0063 | 0.06 | | | | |
| | 55 | C | 76.2 | 20.70 | 3.03 | 0.0092 | 0.06 | | | | |
| | 56 | C | 76.2 | 20.72 | 3 | 0.013 | 0.07 | | | | |
| | 57 | C | 76.3 | 20.52 | 3.06 | 0.039 | 0.08 | | | | |
| | 58 | C | 82.5 | 13.51 | 3.94 | 0.019 | 0.035 | | | | |
| | 59 | C | 75.9 | 21.01 | 3.01 | 0.009 | 0.07 | | | | |
| | 60 | C | 76 | 20.84 | 3.02 | 0.008 | 0.07 | | 0.06 | | |
| | 61 | C | 75.8 | 20.76 | 3.01 | 0.016 | 0.05 | | 0.19 | 0.17 | |
| | 62 | C | 76 | 20.82 | 3.1 | 0.008 | 0.07 | 0.006 | | | |
| | 63 | C | 75.9 | 20.98 | 3.03 | 0.009 | 0.07 | 0.013 | | | |

TABLE 3-continued

| Copper Alloy | | Alloy Composition (mass %) | | | | | | | |
|---|---|---|---|---|---|---|---|---|---|
| No. | Type | Cu | Zn | Si | Zr | P | Pb | Bi | Se | Sn |
| 64 | C | 76.4 | 20.44 | 3.05 | 0.01 | 0.08 | 0.018 | | | |
| 65 | C | 76.4 | 20.33 | 3.1 | 0009 | 0.08 | 0.08 | | | |
| 66 | C | 76.1 | 20.56 | 3.08 | 0.008 | 0.07 | 0.18 | | | |
| 67 | C | 76 | 20.58 | 3.04 | 0.008 | 0.06 | 0.31 | | | |
| 68 | C | 76.2 | 20.65 | 3.08 | 0.009 | 0.06 | 0.003 | | | |
| 69 | C | 78.8 | 18.28 | 2.81 | 0.01 | 0.08 | 0.018 | | | |
| 70 | C | 76.9 | 19.66 | 3.04 | 0.008 | 0.09 | | | | 0.3 |

TABLE 4

| | Copper Alloy | | Alloy Composition (mass %) | | | | | | | | | | | | | |
|---|---|---|---|---|---|---|---|---|---|---|---|---|---|---|---|---|
| | No. | Type | Cu | Zn | Si | Zr | P | Pb | Bi | Se | Te | Sn | Sb | As | Al | Mn |
| Embodiment | 71 | C | 77.8 | 18.76 | 2.85 | 0.008 | 0.08 | | | | | 0.5 | | | | |
| | 72 | C | 76.7 | 20.15 | 3.06 | 0.008 | 0.08 | | | | | | | | | |
| | 73 | C | 76.6 | 20.25 | 3.07 | 0.004 | 0.08 | | | | | | | | | |
| | 74 | D | 76.4 | 20.50 | 3.02 | 0.0064 | 0.07 | | | | | | | | | |
| | 75 | D | 76 | 20.92 | 3 | 0.0093 | 0.07 | | | | | | | | | |
| | 76 | D | 81.4 | 14.50 | 4.05 | 0.02 | 0.035 | | | | | | | | | |
| | 77 | D | 76.9 | 19.64 | 3.08 | 0.009 | 0.07 | | | | | 0.3 | | | | |
| | 78 | D | 77.4 | 18.87 | 3.14 | 0.009 | 0.08 | | | | | 0.5 | | | | |
| | 79 | E | 76.1 | 20.77 | 3.05 | 0.0061 | 0.07 | | | | | | | | | |
| | 80 | E | 76.2 | 20.58 | 3.08 | 0.0075 | 0.07 | | 0.06 | | | | | | | |
| | 81 | E | 75.6 | 20.97 | 2.99 | 0.018 | 0.05 | | 0.19 | 0.18 | | | | | | |
| | 82 | E | 74.9 | 21.95 | 2.89 | 0.0035 | 0.11 | | | | | 0.15 | | | | |
| | 83 | E | 78.8 | 17.28 | 3.76 | 0.0035 | 0.13 | | | | | | 0.03 | | | |
| | 84 | E | 76.5 | 20.23 | 3.11 | 0.0015 | 0.03 | | | | | | | 0.13 | | |
| | 85 | E | 75.2 | 21.19 | 3.12 | 0.0035 | 0.09 | | | | | | | | | 0.4 |
| | 86 | E | 70.9 | 20.88 | 4.48 | 0.0085 | 0.13 | | | | | | | | | 3.6 |
| | 87 | E | 82.1 | 12.60 | 3.8 | 0.014 | 0.04 | | 0.25 | | | | | | 1.2 | |
| | 88 | E | 73.2 | 20.76 | 3.82 | 0.0095 | 0.12 | 0.19 | | | | | | | | 1.9 |
| | 89 | E | 74.8 | 20.16 | 3.5 | 0.018 | 0.08 | 0.14 | | | 0.04 | | | | 0.2 | 1.1 |
| | 90 | E | 75 | 19.92 | 3.5 | 0.018 | 0.08 | | 0.18 | | | | | | 0.1 | 1.2 |
| | 91 | F | 75.8 | 21.00 | 3.1 | 0.019 | 0.08 | | | | | | | | | |
| | 92 | G | 75.8 | 21.11 | 3.02 | 0.006 | 0.06 | | | | | | | | | |

TABLE 5

| | Copper Alloy | | Alloy Composition and Metal Structure(Phase Structure) | | | | | | | | | | | | | |
|---|---|---|---|---|---|---|---|---|---|---|---|---|---|---|---|---|
| | No. | Type | f0 | f1 | f2 | f3 | f6 | f7 | f8 | f9 | f4 | [α] | [β] | [γ] + [κ] | [μ] | f5 |
| Embodiment | 1 | A | 65.3 | 100.0 | 4357 | 44 | 65.3 | 65.3 | 27.0 | 27.0 | 100 | 73 | 0 | 27 | | 27 |
| | 2 | A | 65.0 | 38.9 | 1683 | 43 | 65.0 | 65.0 | 25.0 | 25.0 | 100 | 75 | 0 | 25 | | 25 |
| | 3 | A | 65.3 | 10.3 | 522 | 51 | 65.3 | 65.3 | 25.0 | 25.0 | 100 | 75 | 0 | 25 | | 25 |
| | 4 | A | 65.0 | 7.4 | 322 | 43 | 65.0 | 65.0 | 25.0 | 25.0 | 100 | 75 | 0 | 25 | | 25 |
| | 5 | A | 65.6 | 4.3 | 217 | 51 | 65.6 | 65.6 | 26.0 | 26.0 | 100 | 74 | 0 | 26 | | 26 |
| | 6 | A | 65.5 | 4.4 | 172 | 39 | 65.5 | 65.5 | 27.0 | 27.0 | 100 | 73 | 0 | 27 | | 27 |
| | 7 | A | 65.1 | 3.2 | 109 | 34 | 65.1 | 65.1 | 25.0 | 25.0 | 100 | 75 | 0 | 25 | | 25 |
| | 8 | A | 65.1 | 2.4 | 82 | 34 | 65.1 | 65.1 | 26.0 | 26.0 | 100 | 74 | 0 | 26 | | 26 |
| | 9 | A | 65.3 | 30.0 | 1007 | 34 | 65.3 | 65.3 | 25.0 | 25.0 | 100 | 75 | 0 | 205 | | 25 |
| | 10 | A | 64.4 | 9.0 | 280 | 31 | 64.4 | 64.4 | 21.0 | 21.0 | 100 | 79 | 0 | 21 | | 21 |
| | 11 | A | 65.4 | 7.8 | 367 | 47 | 65.4 | 65.4 | 40.0 | 40.0 | 100 | 60 | 0 | 40 | | 40 |
| | 12 | A | 67.9 | 3.5 | 226 | 64 | 67.9 | 67.9 | 70.0 | 70.0 | 100 | 30 | 0 | 70 | | 70 |
| | 13 | A | 69.5 | 3.8 | 129 | 34 | 69.5 | 69.5 | 10.5 | 10.5 | 95 | 86 | 0 | 9 | 5 | 10.5 |
| | 14 | A | 67.2 | 7.8 | 338 | 43 | 67.2 | 67.2 | 18.3 | 18.3 | 99 | 81 | 0 | 18 | 1 | 18.3 |
| | 15 | A | 65.0 | 4.7 | 178 | 38 | 65.0 | 65.0 | 25.0 | 25.0 | 100 | 75 | 0 | 25 | | 25 |
| | 16 | A | 64.8 | 5.6 | 191 | 34 | 64.8 | 64.8 | 26.0 | 26.0 | 100 | 74 | 0 | 26 | | 26 |
| | 17 | A | 64.9 | 4.7 | 180 | 38 | 64.9 | 64.9 | 25.0 | 25.0 | 100 | 75 | 0 | 25 | | 25 |
| | 18 | A | 65.1 | 7.8 | 339 | 44 | 65.3 | 65.0 | 27.1 | 24.9 | 100 | 74 | 0 | 26 | 0 | 26 |
| | 19 | A | 65.2 | 7.8 | 337 | 43 | 65.4 | 65.0 | 27.9 | 24.1 | 100 | 74 | 0 | 26 | 0 | 26 |
| | 20 | A | 65.2 | 7.8 | 339 | 44 | 65.5 | 64.9 | 28.7 | 23.3 | 100 | 74 | 0 | 26 | 0 | 26 |
| | 21 | A | 65.4 | 7.0 | 305 | 44 | 65.8 | 65.0 | 29.4 | 22.6 | 100 | 74 | 0 | 26 | 0 | 26 |

TABLE 5-continued

| Copper Alloy | | Alloy Composition and Metal Structure(Phase Structure) | | | | | | | | | | | | | |
|---|---|---|---|---|---|---|---|---|---|---|---|---|---|---|---|
| No. | Type | f0 | f1 | f2 | f3 | f6 | f7 | f8 | f9 | f4 | [α] | [β] | [γ] + [κ] | [μ] | f5 |
| 22 | A | 65.5 | 7.8 | 337 | 43 | 66.1 | 64.9 | 31.0 | 21.0 | 100 | 74 | 0 | 26 | 0 | 26 |
| 23 | A | 65.4 | 7.8 | 339 | 44 | 66.2 | 64.5 | 33.1 | 18.9 | 100 | 74 | 0 | 26 | 0 | 26 | f0 = [Cu] − 3.5[Si] − 3[P] + 0.5([Pb] + 0.8([Bi] + [Se]) + 0.6[Te]) − 0.5([Sn] + [As] + [Sb]) − 1.8[Al] + 2[Mn] + [Mg]
f1 = [P]/[Zr] f2 = [Si]/[Zr] f3 = [Si]/[P] f4 = [α] + [γ] + [κ] f5 = [γ] + [κ] + 0.3[μ] − [β]
f6 = [Cu] − 3.5[Si] − 3[P] + 3([Pb] + 0.8([Bi] + [Se]) + 0.6[Te])$^{1/2}$
f7 = [Cu] − 3.5[Si] − 3[P] − 3([Pb] + 0.8([Bi] + [Se]) + 0.6[Te])$^{1/2}$
f8 = [γ] + [κ] + 0.3[μ] − [β] + 25([Pb] + 0.8([Bi] + [Se]) + 0.6[Te])$^{1/2}$
f9 = [γ] + [κ] + 0.3[μ] − [β] − 25([Pb] + 0.8([Bi] + [Se]) + 0.6[Te])$^{1/2}$

TABLE 6

| | Copper Alloy | | Alloy Composition and Metal Structure(Phase Structure) | | | | | | | | | | | | | |
|---|---|---|---|---|---|---|---|---|---|---|---|---|---|---|---|---|
| | No. | Type | f0 | f1 | f2 | f3 | f6 | f7 | f8 | f9 | f4 | [α] | [β] | [γ] + [κ] | [μ] | f5 |
| Embodiment | 24 | A | 65.4 | 7.8 | 338 | 43 | 66.7 | 64.2 | 36.6 | 15.4 | 100 | 74 | 0 | 26 | 0 | 26 |
| | 25 | A | 65.5 | 8.8 | 378 | 43 | 67.1 | 63.8 | 38.9 | 11.1 | 100 | 75 | 0 | 25 | 0 | 25 |
| | 26 | A | 67.3 | 7.8 | 339 | 44 | 67.6 | 67.0 | 20.8 | 15.8 | 99 | 81 | 0 | 18 | 1 | 18.3 |
| | 27 | A | 67.1 | 7.8 | 339 | 44 | 67.5 | 66.7 | 21.7 | 14.9 | 99 | 81 | 0 | 18 | 1 | 18.3 |
| | 28 | A | 67.3 | 10.0 | 380 | 38 | 68.3 | 66.2 | 27.0 | 9.6 | 99 | 81 | 0 | 18 | 1 | 18.3 |
| | 29 | A | 67.3 | 10.0 | 380 | 38 | 68.8 | 65.7 | 31.5 | 5.1 | 99 | 81 | 0 | 18 | 1 | 18.3 |
| | 30 | A | 63.4 | 8.8 | 344 | 39 | 64.2 | 62.6 | 20.6 | 7.4 | 98 | 82 | 2 | 16 | 0 | 14 |
| | 31 | A | 63.4 | 8.9 | 307 | 35 | 64.3 | 62.4 | 21.9 | 6.1 | 98 | 82 | 2 | 16 | 0 | 14 |
| | 32 | A | 65.6 | 8.9 | 411 | 46 | 66.0 | 65.2 | 58.4 | 51.6 | 100 | 45 | 0 | 55 | 0 | 55 |
| | 33 | A | 65.1 | 7.8 | 378 | 49 | 65.5 | 64.7 | 42.4 | 35.6 | 100 | 61 | 0 | 39 | 0 | 39 |
| | 34 | A | 65.7 | 7.8 | 341 | 44 | 65.7 | 65.7 | 26.0 | 26.0 | 100 | 74 | 0 | 26 | 0 | 26 |
| | 35 | A | 65.8 | 8.8 | 393 | 45 | 65.8 | 65.8 | 34.0 | 34.0 | 100 | 66 | 0 | 34 | 0 | 34 |
| | 36 | A | 65.9 | 6.7 | 338 | 51 | 65.9 | 65.9 | 25.0 | 25.0 | 100 | 75 | 0 | 25 | 0 | 25 |
| | 37 | A | 66.4 | 5.7 | 223 | 39 | 66.4 | 66.4 | 35.0 | 35.0 | 100 | 65 | 0 | 35 | 0 | 35 |
| | 38 | A | 63.1 | 12.5 | 329 | 26 | 63.1 | 63.1 | 29.0 | 29.0 | 100 | 71 | 0 | 29 | | 29 |
| | 39 | A | 62.6 | 6.3 | 230 | 37 | 62.6 | 62.6 | 34.0 | 34.0 | 100 | 66 | 0 | 34 | | 34 |
| | 40 | A | 63.9 | 4.5 | 142 | 31 | 63.9 | 63.9 | 44.0 | 44.0 | 100 | 56 | 0 | 44 | | 44 |
| | 41 | A | 65.4 | 114.3 | 4571 | 40 | 65.4 | 65.4 | 26.3 | 26.3 | 99 | 73 | 0 | 26 | 1 | 26.3 |
| | 42 | A | 65.4 | 47.1 | 1835 | 39 | 65.4 | 65.4 | 30.0 | 30.0 | 100 | 70 | 0 | 30 | | 30 |
| | 43 | A | 65.9 | 24.0 | 612 | 26 | 66.3 | 65.5 | 37.1 | 30.9 | 100 | 66 | 0 | 34 | | 34 |
| | 44 | A | 65.6 | 8.2 | 275 | 34 | 66.5 | 64.7 | 36.5 | 21.5 | 100 | 71 | 0 | 29 | | 29 |
| | 45 | A | 65.3 | 7.3 | 293 | 40 | 65.3 | 65.3 | 42.0 | 42.0 | 100 | 58 | 0 | 42 | | 42 |
| | 46 | A | 65.9 | 16.4 | 724 | 44 | 65.9 | 65.9 | 29.0 | 29.0 | 100 | 71 | 0 | 29 | | 29 | f0 = [Cu] − 3.5[Si] − 3[P] + 0.5([Pb] + 0.8([Bi] + [Se]) + 0.6[Te]) − 0.5([Sn] + [As] + [Sb]) − 1.8[Al] + 2[Mn] + [Mg]
f1 = [P]/[Zr] f2 = [Si]/[Zr] f3 = [Si]/[P] f4 = [α] + [γ] + [κ] f5 = [γ] + [κ] + 0.3[μ] − [β]
f6 = [Cu] − 3.5[Si] − 3[P] + 3([Pb] + 0.8([Bi] + [Se]) + 0.6[Te])$^{1/2}$
f7 = [Cu] − 3.5[Si] − 3[P] − 3([Pb] + 0.8([Bi] + [Se]) + 0.6[Te])$^{1/2}$
f8 = [γ] + [κ] + 0.3[μ] − [β] + 25([Pb] + 0.8([Bi] + [Se]) + 0.6[Te])$^{1/2}$
f9 = [γ] + [κ] + 0.3[μ] − [β] − 25([Pb] + 0.8([Bi] + [Se]) + 0.6[Te])$^{1/2}$

TABLE 7

| | Copper Alloy | | Alloy Composition and Metal Structure(Phase Structure) | | | | | | | | | | | | | |
|---|---|---|---|---|---|---|---|---|---|---|---|---|---|---|---|---|
| | No. | Type | f0 | f1 | f2 | f3 | f6 | f7 | f8 | f9 | f4 | [α] | [β] | [γ] + [κ] | [μ] | f5 |
| Embodiment | 47 | B | 65.2 | 7.8 | 300 | 43 | 65.2 | 65.2 | 26.0 | 26.0 | 100 | 74 | 0 | 26 | | 26 |
| | 48 | B | 66.5 | 6.7 | 303 | 53 | 66.5 | 66.5 | 29.0 | 29.0 | 100 | 71 | 0 | 29 | | 29 |
| | 49 | B | 65.3 | 1.6 | 79 | 50 | 65.3 | 65.3 | 25.0 | 25.0 | 100 | 75 | 0 | 25 | | 25 |
| | 50 | B | 67.5 | 8.0 | 305 | 37 | 67.5 | 67.5 | 18.6 | 18.6 | 98 | 80 | 0 | 18 | 2 | 18.6 |
| | 51 | B | 65.2 | 6.7 | 304 | 51 | 65.6 | 64.8 | 29.4 | 22.7 | 100 | 74 | 0 | 26 | | 26 |
| | 52 | B | 65.9 | 6.7 | 339 | 51 | 65.9 | 65.9 | 28.0 | 28.0 | 100 | 72 | 0 | 28 | | 28 |
| | 53 | C | 65.1 | 36.8 | 1605 | 44 | 65.1 | 65.1 | 26.0 | 26.0 | 100 | 74 | 0 | 26 | | 26 |
| | 54 | C | 65.3 | 9.5 | 476 | 50 | 65.3 | 65.3 | 25.0 | 25.0 | 100 | 75 | 0 | 25 | | 25 |
| | 55 | C | 65.4 | 6.5 | 329 | 51 | 65.4 | 65.4 | 26.0 | 26.0 | 100 | 74 | 0 | 26 | | 26 |
| | 56 | C | 65.5 | 5.4 | 231 | 43 | 65.5 | 65.5 | 25.0 | 25.0 | 100 | 75 | 0 | 25 | | 25 |
| | 57 | C | 65.4 | 2.1 | 78 | 38 | 65.4 | 65.4 | 27.0 | 27.0 | 100 | 73 | 0 | 27 | | 27 |
| | 58 | C | 68.6 | 1.8 | 207 | 113 | 68.6 | 68.6 | 81.5 | 81.5 | 95 | 15 | 0 | 80 | 5 | 81.5 |
| | 59 | C | 65.2 | 7.8 | 300 | 43 | 65.2 | 65.2 | 26.0 | 26.0 | 100 | 74 | 0 | 26 | | 26 |
| | 60 | C | 65.3 | 8.8 | 378 | 43 | 65.9 | 64.6 | 31.5 | 20.5 | 100 | 74 | 0 | 26 | 0 | 26 |
| | 61 | C | 65.3 | 3.1 | 188 | 60 | 66.9 | 63.7 | 38.4 | 11.6 | 100 | 75 | 0 | 25 | 0 | 25 |
| | 62 | C | 64.9 | 8.8 | 388 | 44 | 65.2 | 64.7 | 28.9 | 25.1 | 100 | 73 | 0 | 27 | | 27 |
| | 63 | C | 65.1 | 7.8 | 337 | 43 | 65.4 | 64.7 | 28.9 | 23.1 | 100 | 74 | 0 | 26 | | 26 |

TABLE 7-continued

| Copper Alloy | | Alloy Composition and Metal Structure(Phase Structure) | | | | | | | | | | | | |
|---|---|---|---|---|---|---|---|---|---|---|---|---|---|---|
| No. | Type | f0 | f1 | f2 | f3 | f6 | f7 | f8 | f9 | f4 | [α] | [β] | [γ] + [κ] | [μ] | f5 |
| 64 | C | 65.5 | 8.0 | 305 | 38 | 65.9 | 65.1 | 28.4 | 21.6 | 100 | 75 | 0 | 25 | | 25 |
| 65 | C | 65.4 | 8.9 | 344 | 39 | 66.2 | 64.5 | 34.1 | 19.9 | 100 | 73 | 0 | 27 | | 27 |
| 66 | C | 65.2 | 8.8 | 385 | 44 | 66.5 | 63.9 | 37.6 | 16.4 | 100 | 73 | 0 | 27 | | 27 |
| 67 | C | 65.3 | 7.5 | 380 | 51 | 67.0 | 63.7 | 39.9 | 12.1 | 100 | 74 | 0 | 26 | | 26 |
| 68 | C | 65.2 | 6.7 | 342 | 51 | 65.4 | 65.1 | 28.4 | 25.6 | 100 | 73 | 0 | 27 | | 27 |
| 69 | C | 68.7 | 8.0 | 281 | 35 | 69.1 | 68.3 | 16.4 | 9.6 | 100 | 87 | 0 | 13 | | 13 |
| 70 | C | 65.8 | 11.3 | 380 | 34 | 65.8 | 65.8 | 28.0 | 28.0 | 100 | 72 | 0 | 28 | | 28 | f0 = [Cu] − 3.5[Si] − 3[P] + 0.5([Pb] + 0.8([Bi] + [Se]) + 0.6[Te]) − 0.5([Sn] + [As] + [Sb]) − 1.8[Al] + 2[Mn] + [Mg]
f1 = [P]/[Zr] f2 = [Si]/[Zr] f3 = [Si]/[P] f4 = [α] + [γ] + [κ] f5 = [γ] + [κ] + 0.3[μ] − [β]
f6 = [Cu] − 3.5[Si] − 3[P] + 3([Pb] + 0.8([Bi] + [Se]) + 0.6[Te])$^{1/2}$
f7 = [Cu] − 3.5[Si] − 3[P] − 3([Pb] + 0.8([Bi] + [Se]) + 0.6[Te])$^{1/2}$
f8 = [γ] + [κ] + 0.3[μ] − [β] + 25([Pb] + 0.8([Bi] + [Se]) + 0.6[Te])$^{1/2}$
f9 = [γ] + [κ] + 0.3[μ] − [β] − 25([Pb] + 0.8([Bi] + [Se]) + 0.6[Te])$^{1/2}$

TABLE 8

| Copper Alloy | | Alloy Composition and Metal Structure (Phase Structure) | | | | | | | | | | | | |
|---|---|---|---|---|---|---|---|---|---|---|---|---|---|---|
| No. | Type | f0 | f1 | f2 | f3 | f6 | f7 | f8 | f9 | f4 | [α] | [β] | [γ]+[κ] | [μ] | f5 |

Embodiment

| No. | Type | f0 | f1 | f2 | f3 | f6 | f7 | f8 | f9 | f4 | [α] | [β] | [γ]+[κ] | [μ] | f5 |
|---|---|---|---|---|---|---|---|---|---|---|---|---|---|---|---|
| 71 | C | 67.3 | 10 | 356 | 36 | 67.3 | 67.3 | 20.0 | 20.0 | 100 | 80 | 0 | 20 | | 20 |
| 72 | C | | 10.0 | 383 | 38 | | | | | | | | | | |
| 73 | C | | 20.0 | 768 | 38 | | | | | | | | | | |
| 74 | D | 65.6 | 10.9 | 472 | 43 | 65.6 | 65.6 | 25.0 | 25.0 | 100 | 75 | 0 | 25 | | 25 |
| 75 | D | 65.3 | 7.5 | 323 | 43 | 65.3 | 65.3 | 25.0 | 25.0 | 100 | 75 | 0 | 25 | | 25 |
| 76 | D | 67.1 | 1.8 | 203 | 116 | 67.1 | 67.1 | 89.5 | 89.5 | 95 | 7 | 0 | 88 | 5 | 89.5 |
| 77 | D | 65.8 | 7.8 | 342 | 44 | 65.8 | 65.8 | 26.0 | 26.0 | 100 | 74 | 0 | 26 | 0 | 26 |
| 78 | D | 65.9 | 8.9 | 349 | 39 | 65.9 | 65.9 | 34.0 | 34.0 | 100 | 66 | 0 | 34 | 0 | 34 |
| 79 | E | 65.2 | 11.5 | 500 | 44 | 65.2 | 65.2 | 26.0 | 26.0 | 100 | 74 | 0 | 26 | | 26 |
| 80 | E | 65.2 | 9.3 | 411 | 44 | 65.9 | 64.6 | 32.5 | 21.5 | 100 | 73 | 0 | 27 | 0 | 27 |
| 81 | E | 65.2 | 2.8 | 166 | 60 | 66.8 | 63.5 | 38.6 | 11.4 | 100 | 75 | 0 | 25 | 0 | 25 |
| 82 | E | 64.4 | 31.4 | 826 | 26 | 64.4 | 64.4 | 22.0 | 22.0 | 100 | 78 | 0 | 22 | 0 | 22 |
| 83 | E | 65.2 | 37.1 | 1074 | 29 | 65.2 | 65.2 | 54.0 | 54.0 | 100 | 46 | 0 | 54 | | 54 |
| 84 | E | 65.5 | 20.0 | 2073 | 104 | 65.5 | 65.5 | 30.0 | 30.0 | 100 | 70 | 0 | 30 | | 30 |
| 85 | E | 64.8 | 25.7 | 891 | 35 | 64.8 | 64.8 | 26.0 | 26.0 | 100 | 74 | 0 | 26 | | 26 |
| 86 | E | 62 | 15.3 | 527 | 34 | 62.0 | 62.0 | 30.0 | 30.0 | 100 | 70 | 0 | 30 | | 30 |
| 87 | E | 66.6 | 2.9 | 271 | 95 | 68.0 | 65.3 | 95.2 | 72.8 | 100 | 16 | 0 | 84 | | 84 |
| 88 | E | 63.4 | 12.6 | 402 | 32 | 64.7 | 62.1 | 44.9 | 23.1 | 100 | 66 | 0 | 34 | | 34 |
| 89 | E | 64.2 | 4.4 | 194 | 44 | 65.5 | 63.0 | 41.1 | 20.9 | 100 | 69 | 0 | 31 | | 31 |
| 90 | E | 64.8 | 4.4 | 194 | 44 | 66.0 | 63.7 | 39.5 | 20.5 | 100 | 70 | 0 | 30 | | 30 |
| 91 | F | | | | | 0.0 | 0.0 | 0.0 | 0.0 | | | | | | |
| 92 | G | 65.1 | 10 | 503 | 50 | 65.1 | 65.1 | 25.0 | 25 | 100 | 75 | 0 | 25 | | 25 | f0 = [Cu]−3.5[Si]−3[P]+0.5([Pb]+0.8([Bi]+[Se])+0.6[Te])−0.5([Sn]+[As]+[Sb])−1.8[Al]+2[Mn]+[Mg]
f1 = [P]/[Zr]
f2 = [Si]/[Zr]
f3 = [Si]/[P]
f4 = [α]+[γ]+[κ]
f5 = [γ]+[κ]+0.3[μ]−[β]
f6 = [Cu]−3.5[Si]−3[P]+3([Pb]+0.8([Bi]+[Se])+0.6[Te])$^{1/2}$
f7 = [Cu]−3.5[Si]−3[P]−3([Pb]+0.8([Bi]+[Se])+0.6[Te])$^{1/2}$
f8 = [γ]+[κ]+0.3[μ]−[β]+25([Pb]+0.8([Bi]+[Se])+0.6[Te])$^{1/2}$
f9 = [γ]+[κ]+0.3[μ]−[β]−25([Pb]+0.8([Bi]+[Se])+0.6[Te])$^{1/2}$

TABLE 9

| | Copper Alloy | | Alloy Composition (mass %) | | | | | | |
|---|---|---|---|---|---|---|---|---|---|
| | No. | Type | Cu | Zn | Si | Zr | P | Pb | Bi | Sn |
| Comparative Example | 201 | A1 | 76.5 | 20.47 | 3.03 | | 0.07 | | | |
| | 202 | A1 | 75.9 | 20.99 | 3.04 | 0.0002 | 0.07 | | | |
| | 203 | A1 | 75 | 21.87 | 3 | 0.05 | 0.08 | | | |
| | 204 | A1 | 75.6 | 21.29 | 3.1 | 0.005 | 0.005 | | | |
| | 205 | A1 | 78.8 | 18.90 | 2.2 | 0.028 | 0.07 | | | |
| | 206 | A1 | 78.1 | 18.83 | 3.05 | 0.009 | 0.008 | | | |
| | 207 | A1 | 73 | 24.16 | 2.76 | 0.0002 | 0.07 | 0.01 | | |

TABLE 9-continued

| Copper Alloy | | Alloy Composition (mass %) | | | | | | | |
|---|---|---|---|---|---|---|---|---|---|
| No. | Type | Cu | Zn | Si | Zr | P | Pb | Bi | Sn |
| 208 | A1 | 69.4 | 27.83 | 2.65 | 0.017 | 0.1 | | | |
| 209 | A1 | 79.6 | 18.24 | 2.1 | 0.003 | 0.06 | | | |
| 210 | A1 | 68.5 | 29.31 | 2.1 | 0.013 | 0.08 | | | |
| 211 | A1 | 79.9 | 16.06 | 4.04 | | | | | |
| 212 | A1 | 73.8 | 23.44 | 2.53 | 0.15 | 0.08 | | | |
| 213 | A1 | 69.3 | 28.74 | 1.9 | 0.008 | 0.05 | | | |
| 214 | A1 | 70.1 | 27.03 | 2.77 | 0.018 | 0.08 | | | |
| 215 | A1 | 84.6 | 5.57 | | | 0.03 | 5.2 | | 4.6 |
| 216 | A1 | 86.3 | 6.40 | | | | | 2.7 | 4.6 |
| 217 | B1 | 78 | 18.96 | 2.96 | 0 | 0.08 | | | |
| 218 | B1 | 77.1 | 19.27 | 3.06 | 0.0003 | 0.07 | | | 0.5 |
| 219 | C1 | 82.5 | 15.15 | 2.25 | 0.006 | 0.09 | | | |
| 220 | C1 | 80.3 | 15.68 | 4.02 | | | | | |
| 221 | C1 | 76.2 | 20.07 | 3.1 | 0.01 | 0.07 | 0.55 | | |
| 222 | C1 | 76.4 | 20.45 | 3.05 | 0.0002 | 0.08 | 0.018 | | |
| 223 | C1 | 77.8 | 18.77 | 2.86 | 0.0003 | 0.07 | | | 0.5 |

TABLE 10

| | Copper Alloy | | Alloy Composition (mass %) | | | | | | Impurity | |
|---|---|---|---|---|---|---|---|---|---|---|---|
| | No. | Type | Cu | Zn | Si | Zr | P | Pb | Sn | Fe | Ni |
| Comparative Example | 224 | C1 | 76.6 | 20.27 | 3.05 | | 0.08 | | | | |
| | 225 | D1 | 76.2 | 20.79 | 3.01 | | | | | | |
| | 226 | D1 | 84.8 | 5.50 | | | | 4.8 | 4.9 | | |
| | 227 | E1 | 70.3 | 27.09 | 2.5 | 0.012 | 0.1 | | | | |
| | 228 | E1 | 76 | 20.96 | 3.04 | | | | | | |
| | 229 | E1 | 73 | 22.91 | 3.98 | 0.015 | 0.1 | | | | |
| | 230 | E1 | 85.8 | 8.59 | 5.5 | 0.011 | 0.1 | | | | |
| | 231 | E1 | 76.6 | 19.83 | 3.11 | 0.018 | 0.09 | | | 0.35 | |
| | 232 | E1 | 75.8 | 20.74 | 3.05 | 0.018 | 0.08 | | | | 0.31 |
| | 233 | E1 | 75.8 | 20.64 | 3.05 | 0.018 | 0.08 | | | 0.13 | 0.28 |
| | 234 | F1 | 75.8 | 21.02 | 3.1 | | 0.08 | | | | |
| | 235 | G1 | 60.9 | 35.80 | | | | 3.1 | 0.2 | | |
| | 236 | G1 | 58.8 | 38.90 | | | | 2 | 0.3 | | |

TABLE 11

| | Copper Alloy | | Alloy Composition and Metal Structure (Phase Structure) | | | | | | | | | | | | | |
|---|---|---|---|---|---|---|---|---|---|---|---|---|---|---|---|---|
| | No. | Type | f0 | f1 | f2 | f3 | f6 | f7 | f8 | f9 | f4 | [α] | [β] | [γ] + [κ] | [μ] | f5 |
| Comparative Example | 201 | A1 | 65.9 | | | | 65.9 | 65.9 | 25.0 | 25.0 | 100 | 75 | 0 | 25 | | 25 |
| | 202 | A1 | 65.1 | 350.0 | 15200 | 43 | 65.1 | 65.1 | 25.0 | 25.0 | 100 | 75 | 0 | 25 | | 25 |
| | 203 | A1 | 64.3 | 1.6 | 60 | 38 | 64.3 | 64.3 | 24.0 | 24.0 | 100 | 76 | 0 | 24 | | 24 |
| | 204 | A1 | 64.7 | 1.0 | 620 | 620 | 64.7 | 64.7 | 29.0 | 29.0 | 100 | 71 | 0 | 29 | | 29 |
| | 205 | A1 | 70.9 | 2.5 | 79 | 31 | 70.9 | 70.9 | 3.0 | 3.0 | 100 | 97 | 0 | 3 | 0 | 3 |
| | 206 | A1 | 67.4 | 0.9 | 339 | 381 | 67.4 | 67.4 | 18.3 | 18.3 | 99 | 81 | 0 | 18 | 1 | 18.3 |
| | 207 | A1 | 63.1 | 350.0 | 13800 | 39 | 63.4 | 62.8 | 16.5 | 11.5 | 98 | 82 | 2 | 16 | 0 | 14 |
| | 208 | A1 | 59.8 | 5.9 | 156 | 27 | 59.8 | 59.8 | −12.0 | −12.0 | 70 | 52 | 30 | 18 | | −12 |
| | 209 | A1 | 72.1 | 20.0 | 700 | 35 | 72.1 | 72.1 | 2.5 | 2.5 | 95 | 94 | 0 | 1 | 5 | 2.5 |
| | 210 | A1 | 60.9 | 6.2 | 162 | 26 | 60.9 | 60.9 | −9.0 | −9.0 | 85 | 79 | 15 | 6 | | −9 |
| | 211 | A1 | 65.8 | | | | 65.8 | 65.8 | 86 | 86 | 100 | 14 | 0 | 86 | | 86 |
| | 212 | A1 | 64.7 | 0.5 | 17 | 32 | 64.7 | 64.7 | 14.0 | 14.0 | 100 | 86 | 0 | 14 | | 14 |
| | 213 | A1 | 62.5 | 6.3 | 238 | 38 | 62.5 | 62.5 | −5.0 | −5.0 | 95 | 95 | 5 | 0 | | −5 |
| | 214 | A1 | 60.2 | 4.4 | 154 | 35 | 60.2 | 60.2 | −12.0 | −12.0 | 75 | 62 | 25 | 13 | | −12 |
| | 215 | A1 | 84.8 | | | | 91.7 | 78.0 | 57.0 | −57.0 | | — | | | | 0 |
| | 216 | A1 | 85.4 | | | | 89.8 | 80.9 | 36.7 | −36.7 | | — | | | | 0 |
| | 217 | B1 | 67.4 | | | 37 | 67.4 | 67.4 | 18.6 | 18.6 | 98 | 80 | 0 | 18 | 2 | 18.6 |
| | 218 | B1 | 65.9 | 233.3 | 10200 | 44 | 65.9 | 65.9 | 27.0 | 27.0 | 100 | 73 | 0 | 27 | | 27 |
| | 219 | C1 | 74.4 | 15.0 | 375 | 25 | 74.4 | 74.4 | 0.0 | 0.0 | 100 | 100 | 0 | 0 | | 0 |
| | 220 | C1 | 66.2 | | | | 66.2 | 66.2 | 85.0 | 85.0 | 100 | 15 | 0 | 85 | | 85 |
| | 221 | C1 | 65.4 | 7.0 | 310 | 44 | 67.6 | 63.2 | 46.5 | 9.5 | 100 | 72 | 0 | 28 | | 28 |

TABLE 11-continued

| Copper Alloy | | Alloy Composition and Metal Structure (Phase Structure) | | | | | | | | | | | | |
|---|---|---|---|---|---|---|---|---|---|---|---|---|---|---|
| No. | Type | f0 | f1 | f2 | f3 | f6 | f7 | f8 | f9 | f4 | [α] | [β] | [γ] + [κ] | [μ] | f5 |
| 222 | C1 | 65.5 | 400 | 15250 | 38 | 65.9 | 65.1 | 29.4 | 22.6 | 100 | 74 | 0 | 26 | | 26 |
| 223 | C1 | 67.3 | 233.3 | 9533 | 41 | 67.3 | 67.3 | 20.0 | 20.0 | 100 | 80 | 0 | 20 | | 20 | f0 = [Cu] − 3.5[Si] − 3[P] + 0.5([Pb] + 0.8([Bi] + [Se]) + 0.6[Te]) − 0.5([Sn] + [As] + [Sb]) − 1.8[Al] + 2[Mn] + [Mg]
f1 = [P]/[Zr]
f2 = [Si]/[Zr]
f3 = [Si]/[P]
f4 = [α] + [γ] + [κ]
f5 = [γ] + [κ] + 0.3[μ] − [β]
f6 = [Cu] − 3.5[Si] − 3[P] + 3([Pb] + 0.8([Bi] + [Se]) + 0.6[Te])$^{1/2}$
f7 = [Cu] − 3.5[Si] − 3[P] − 3([Pb] + 0.8([Bi] + [Se]) + 0.6[Te])$^{1/2}$
f8 = [γ] + [κ] + 0.3[μ] − [β] + 25([Pb] + 0.8([Bi] + [Se]) + 0.6[Te])$^{1/2}$
f9 = [γ] + [κ] + 0.3[μ] − [β] − 25([Pb] + 0.8([Bi] + [Se]) + 0.6[Te])$^{1/2}$

TABLE 12

| | Copper Alloy | | Alloy Composition and Metal Structure (Phase Structure) | | | | | | | | | | | | |
|---|---|---|---|---|---|---|---|---|---|---|---|---|---|---|---|
| | No. | Type | f0 | f1 | f2 | f3 | f6 | f7 | f8 | f9 | f4 | [α] | [β] | [γ] + [κ] | [μ] | f5 |
| Comparative Example | 224 | C1 | | | | 38 | | | | | | | | | | |
| | 225 | D1 | 65.7 | | | | 65.7 | 65.7 | 25.0 | 25.0 | 100 | 75 | 0 | 25 | | 25 |
| | 226 | D1 | 84.8 | | | | 91.3 | 78.2 | 54.8 | −54.8 | | — | | | | 0 |
| | 227 | E1 | 61.3 | 8.3 | 208 | 25 | 61.3 | 61.3 | 4.0 | 4.0 | 90 | 78 | 9 | 13 | | 4 |
| | 228 | E1 | 65.4 | | | | 65.4 | 65.4 | 26.0 | 26.0 | 100 | 74 | 0 | 26 | | 26 |
| | 229 | E1 | 58.8 | 6.7 | 265 | 40 | 58.8 | 58.8 | −24.0 | −24.0 | 65 | 54 | 35 | 11 | | −24 |
| | 230 | E1 | 66.3 | 9.1 | 500 | 55 | 66.3 | 66.3 | 89.0 | 89.0 | 90 | 4 | 0 | 86 | 10 | 89 |
| | 231 | E1 | 65.4 | 5.0 | 173 | 35 | 65.4 | 65.4 | 29.0 | 29.0 | 100 | 71 | 0 | 29 | | 29 |
| | 232 | E1 | 64.9 | 4.4 | 169 | 38 | 64.9 | 64.9 | 26.0 | 26.0 | 10 | 74 | 0 | 26 | | 26 |
| | 233 | E1 | 64.9 | 4.4 | 169 | 38 | 64.9 | 64.9 | 26.0 | 26.0 | 100 | 74 | 0 | 26 | | 26 |
| | 234 | F1 | | | | | | | | | | | | | | |
| | 235 | G1 | 62.4 | | | | 67.6 | 57.1 | 44.0 | −44.0 | | — | | | | 0 |
| | 236 | G1 | 59.7 | | | | 63.9 | 55.4 | 35.4 | −35.4 | | — | | | | 0 | f0 = [Cu] − 3.5[Si] − 3[P] + 0.5([Pb] + 0.8([Bi] + [Se]) + 0.6[Te]) − 0.5([Sn] + [As] + [Sb]) − 1.8[Al] + 2[Mn] + [Mg]
f1 = [P]/[Zr]
f2 = [Si]/[Zr]
f3 = [Si]/[P]
f4 = [α] + [γ] + [κ]
f5 = [γ] + [κ] + 0.3[μ] − [β]
f6 = [Cu] − 3.5[Si] − 3[P] + 3([Pb] + 0.8([Bi] + [Se]) + 0.6[Te])$^{1/2}$
f7 = [Cu] − 3.5[Si] − 3[P] − 3([Pb] + 0.8([Bi] + [Se]) + 0.6[Te])$^{1/2}$
f8 = [γ] + [κ] + 0.3[μ] − [β] + 25([Pb] + 0.8([Bi] + [Se]) + 0.6[Te])$^{1/2}$
f9 = [γ] + [κ] + 0.3[μ] − [β] − 25([Pb] + 0.8([Bi] + [Se]) + 0.6[Te])$^{1/2}$

TABLE 13

| | Copper Alloy | | Average Grain Diameter (μm) | Machinability | | | | Tensile Strength (N/mm$^2$) | Yield Strength (N/mm$^2$) | Elongation (%) | Fatigue Strength (N/mm$^2$) |
|---|---|---|---|---|---|---|---|---|---|---|---|
| | | | | Type of chips | | Cutting main stress (N) | | | | | |
| | No. | Type | | 80 m/min | 160 m/min | 80 m/min | 160 m/min | | | | |
| Embodiment | 1 | A | 85 | | | | | | | | |
| | 2 | A | 40 | | | | | | | | |
| | 3 | A | 25 | ◉ | ○ | | | 532 | 245 | 44 | 253 |
| | 4 | A | 15 | ◉ | ○ | | | 535 | 268 | 45 | 258 |
| | 5 | A | 25 | ◉ | ○ | | | 523 | 256 | 44 | 254 |
| | 6 | A | 30 | ◉ | ○ | | | | | | |
| | 7 | A | 55 | | | | | 492 | 219 | 42 | |
| | 8 | A | 90 | | | | | | | | |
| | 9 | A | 40 | | | | | 498 | 236 | 30 | |
| | 10 | A | 25 | ◉ | ○ | | | | | | |
| | 11 | A | 20 | | | | | | | | |
| | 12 | A | 65 | | | | | | | | |
| | 13 | A | 80 | | | | | | | | |
| | 14 | A | 45 | ○ | Δ | 122 | 133 | | | | |
| | 15 | A | 65 | | | | | 485 | 206 | 39 | |

TABLE 13-continued

| | Copper Alloy | | Average Grain Diameter (μm) | Machinability | | | | Tensile Strength (N/mm²) | Yield Strength (N/mm²) | Elongation (%) | Fatigue Strength (N/mm²) |
|---|---|---|---|---|---|---|---|---|---|---|---|
| | | | | Type of chips | | Cutting main stress (N) | | | | | |
| | No. | Type | | 80 m/min | 160 m/min | 80 m/min | 160 m/min | | | | |
| | 16 | A | 70 | | | | | | | | |
| | 17 | A | 30 | | | | | | | | |
| | 18 | A | 20 | ◎ | ○ | 115 | 127 | | | | |
| | 19 | A | 20 | ◎ | ○ | 111 | 118 | | | | |
| | 20 | A | 20 | ◎ | ○ | 110 | 118 | | | | |
| | 21 | A | 20 | ◎ | ◎ | 110 | 117 | | | | |
| | 22 | A | 20 | ◎ | ◎ | 109 | 116 | | | | |
| | 23 | A | 20 | ◎ | ◎ | 108 | 114 | 530 | 266 | 43 | 254 |

TABLE 14

| | Copper Alloy | | Average Grain Diameter (μm) | Machinability | | | | Tensile Strength (N/mm²) | Yield Strength (N/mm²) | Elongation (%) | Fatigue Strength (N/mm²) |
|---|---|---|---|---|---|---|---|---|---|---|---|
| | | | | Type of chips | | Cutting main stress (N) | | | | | |
| | No. | Type | | 80 m/min | 160 m/min | 80 m/min | 160 m/min | | | | |
| Embodiment | 24 | A | 20 | ◎ | ◎ | 106 | 112 | | | | |
| | 25 | A | 20 | ● | ◎ | 104 | 109 | 522 | 251 | 38 | |
| | 26 | A | 45 | ○ | ○ | 115 | 124 | | | | |
| | 27 | A | 45 | ◎ | ○ | 114 | 123 | | | | |
| | 28 | A | 45 | ◎ | ○ | 111 | 119 | | | | |
| | 29 | A | 45 | ◎ | ◎ | 109 | 115 | | | | |
| | 30 | A | 40 | ○ | ○ | 114 | 124 | | | | |
| | 31 | A | 40 | ◎ | ○ | 110 | 118 | | | | |
| | 32 | A | 35 | ◎ | ○ | 113 | 122 | | | | |
| | 33 | A | 25 | ◎ | ◎ | 111 | 119 | | | | |
| | 34 | A | 15 | | | | | 528 | 272 | 40 | 262 |
| | 35 | A | 20 | ◎ | ○ | 116 | 127 | 520 | 260 | 34 | |
| | 36 | A | 20 | ◎ | ○ | 117 | 129 | | | | |
| | 37 | A | 20 | | | | | 443 | 256 | 13 | |
| | 38 | A | 25 | ○ | △ | | | 642 | 302 | 30 | 304 |
| | 39 | A | 45 | | | | | | | | |
| | 40 | A | 30 | ○ | △ | | | 554 | 256 | 33 | |
| | 41 | A | 60 | | | | | | | | |
| | 42 | A | 20 | | | | | | | | |
| | 43 | A | 20 | ◎ | ○ | 114 | 123 | 525 | 261 | 34 | 252 |
| | 44 | A | 20 | ◎ | ◎ | 111 | 116 | | | | |
| | 45 | A | 15 | | | | | | | | |
| | 46 | A | 15 | | | | | 612 | 288 | 32 | |

TABLE 15

| | Copper Alloy | | Average Grain Diameter (μm) | Machinability | | | | Tensile Strength (N/mm²) | Yield Strength (N/mm²) | Elongation (%) | Fatigue Strength (N/mm²) |
|---|---|---|---|---|---|---|---|---|---|---|---|
| | | | | Type of chips | | Cutting main stress (N) | | | | | |
| | No. | Type | | 80 m/min | 160 m/min | 80 m/min | 160 m/min | | | | |
| Embodiment | 47 | B | 15 | ◎ | ○ | 115 | 128 | 720 | 640 | 17 | 336 |
| | 48 | B | 15 | ◎ | ○ | 116 | 128 | 735 | 655 | 15 | |
| | 49 | B | 150 | | | | | 698 | 599 | 14 | |
| | 50 | B | 25 | ○ | ○ | 119 | 134 | 705 | 613 | 19 | |
| | 51 | B | 15 | ◎ | ◎ | 110 | 117 | 715 | 632 | 16 | |
| | 52 | B | 15 | ◎ | ○ | 117 | 129 | 730 | 651 | 15 | |
| | 53 | C | 35 | | | | | 501 | 234 | 30 | |
| | 54 | C | 20 | | | | | 524 | 262 | 32 | |
| | 55 | C | 15 | | | | | 534 | 278 | 34 | |
| | 56 | C | 25 | | | | | 515 | 250 | 33 | |
| | 57 | C | 80 | | | | | 468 | 203 | 28 | |

TABLE 15-continued

| Copper Alloy | | Average Grain Diameter | Machinability | | | | Tensile Strength | Yield Strength | Elongation | Fatigue Strength |
| | | | Type of chips | | Cutting main stress (N) | | | | | |
| No. | Type | (μm) | 80 m/min | 160 m/min | 80 m/min | 160 m/min | (N/mm²) | (N/mm²) | (%) | (N/mm²) |
|---|---|---|---|---|---|---|---|---|---|---|
| 58 | C | 80 | | | | | 546 | 245 | 27 | |
| 59 | C | 15 | | | | | 526 | 257 | 32 | |
| 60 | C | 25 | | | | | 522 | 252 | 40 | |
| 61 | C | 25 | | | | | | | | |
| 62 | C | 15 | | | | | 521 | 250 | 33 | |
| 63 | C | 15 | | | | | | | | |
| 64 | C | 20 | | | | | 525 | 255 | 32 | |
| 65 | C | 15 | | | | | | | | |
| 66 | C | 20 | | | | | | | | |
| 67 | C | 15 | | | | | 521 | 250 | 31 | |
| 68 | C | 20 | | | | | | | | |
| 69 | C | 70 | | | | | | | | |
| 70 | C | 20 | | | | | | | | |

TABLE 16

| | Copper Alloy | | Average Grain Diameter | Machinability | | | | Tensile Strength | Yield Strength | Elongation | Fatigue Strength |
| | | | | Type of chips | | Cutting main stress (N) | | | | | |
| | No. | Type | (μm) | 80 m/min | 160 m/min | 80 m/min | 160 m/min | (N/mm²) | (N/mm²) | (%) | (N/mm²) |
|---|---|---|---|---|---|---|---|---|---|---|---|
| Embodiment | 71 | C | 30 | | | | | 488 | 235 | 34 | |
| | 72 | C | 20 | | | | | 528 | 289 | 32 | |
| | 73 | C | 22 | | | | | 523 | 285 | 33 | |
| | 74 | D | 30 | | | | | 514 | 240 | 34 | |
| | 75 | D | 20 | | | | | 516 | 254 | 36 | |
| | 76 | D | 80 | | | | | 522 | 235 | 26 | |
| | 77 | D | 15 | | | | | | | | |
| | 78 | D | 20 | | | | | | | | |
| | 79 | E | 25 | | | | | 520 | 256 | 33 | |
| | 80 | E | 25 | ◎ | ◎ | 109 | 116 | 518 | 248 | 28 | |
| | 81 | E | 25 | ◎ | ◎ | 107 | 113 | | | | |
| | 82 | E | 25 | | | | | | | | |
| | 83 | E | 30 | ○ | Δ | | | | | | |
| | 84 | E | 50 | | | | | | | | |
| | 85 | E | 30 | ◎ | ○ | | | | | | |
| | 86 | E | 65 | | | | | | | | |
| | 87 | E | 55 | | | | | | | | |
| | 88 | E | 20 | ◎ | ○ | | | | | | |
| | 89 | E | 30 | ◎ | ○ | 116 | 124 | 598 | 276 | 26 | 272 |
| | 90 | E | 30 | ◎ | ○ | 117 | 126 | | | | |
| | 91 | F | 50 | | | | | 477 | 245 | 27 | |
| | 92 | G | 15 | | | | | 536 | 284 | 38 | |

TABLE 17

| | Copper Alloy | | Average Grain Diameter | Machinability | | | | Tensile Strength | Yield Strength | Elongation | Fatigue Strength |
| | | | | Type of chips | | Cutting main stress (N) | | | | | |
| | No. | Type | (μm) | 80 m/min | 160 m/min | 80 m/min | 160 m/min | (N/mm²) | (N/mm²) | (%) | (N/mm²) |
|---|---|---|---|---|---|---|---|---|---|---|---|
| Comparative Example | 201 | A1 | 1500 | | | | | 435 | 170 | 36 | 156 |
| | 202 | A1 | 600 | ◎ | Δ | | | 433 | 174 | 34 | 254 |
| | 203 | A1 | 220 | | | | | 440 | 188 | 32 | 176 |
| | 204 | A1 | 350 | ◎ | Δ | | | | | | |
| | 205 | A1 | 100 | X | XX | 175 | 203 | | | | |
| | 206 | A1 | 400 | □ | X | 130 | 152 | | | | |
| | 207 | A1 | 600 | □ | X | 122 | 142 | | | | |

TABLE 17-continued

| Copper Alloy | | Average Grain Diameter | Machinability | | | | Tensile Strength | Yield Strength | Elongation | Fatigue Strength |
| | | | Type of chips | | Cutting main stress (N) | | | | | |
| No. | Type | (μm) | 80 m/min | 160 m/min | 80 m/min | 160 m/min | (N/mm²) | (N/mm²) | (%) | (N/mm²) |
|---|---|---|---|---|---|---|---|---|---|---|
| 208 | A1 | 600 | X | XX | 173 | 201 | | | | |
| 209 | A1 | 300 | XX | XX | 179 | 212 | | | | |
| 210 | A1 | 400 | | | | | | | | |
| 211 | A1 | 1200 | | | | | | | | |
| 212 | A1 | 200 | Δ | XX | 135 | 178 | | | | |
| 213 | A1 | 250 | XX | XX | 205 | 226 | | | | |
| 214 | A1 | 500 | | | | | | | | |
| 215 | A1 | 1000 | ● | ◎ | 99 | 110 | 296 | 95 | 25 | |
| 216 | A1 | 1200 | ◎ | ○ | 110 | 121 | 282 | 94 | 21 | |
| 217 | B1 | 450 | Δ | Δ | 128 | 147 | 650 | 558 | 15 | |
| 218 | B1 | 350 | ○ | Δ | 126 | 142 | 684 | 572 | 6 | |
| 219 | C1 | 300 | | | | | | | | |
| 220 | C1 | 1000 | | | | | | | | |
| 221 | C1 | 20 | | | | | | | | |
| 222 | C1 | 600 | | | | | 418 | 184 | 23 | |
| 223 | C1 | 500 | | | | | 394 | 178 | 25 | |

TABLE 18

| | Copper Alloy | | Average Grain Diameter | Machinability | | | | Tensile Strength | Yield Strength | Elongation | Fatigue Strength |
| | | | | Type of chips | | Cutting main stress (N) | | | | | |
| | No. | Type | (μm) | 80 m/min | 160 m/min | 80 m/min | 160 m/min | (N/mm²) | (N/mm²) | (%) | (N/mm²) |
|---|---|---|---|---|---|---|---|---|---|---|---|
| Comparative Example | 224 | C1 | 400 | | | | | 441 | 194 | 30 | |
| | 225 | D1 | 2000 | | | | | 412 | 166 | 22 | |
| | 226 | D1 | 1200 | | | | | 232 | 80 | 22 | |
| | 227 | E1 | 90 | X | X | | | | | | |
| | 228 | E1 | 1500 | | | | | 426 | 170 | 24 | |
| | 229 | E1 | 800 | | | | | | | | |
| | 230 | E1 | 200 | X | XX | | | | | | |
| | 231 | E1 | 400 | Δ | □ | | | 430 | 174 | 25 | |
| | 232 | E1 | 350 | | | | | 438 | 188 | 26 | |
| | 233 | E1 | 350 | | | | | | | | |
| | 234 | F1 | 2500 | | | | | 408 | 162 | 25 | |
| | 235 | G1 | 25 | ● | ● | 96 | 101 | 387 | 165 | 39 | |
| | 236 | G1 | 35 | ● | ◎ | 102 | 109 | 398 | 175 | 36 | |

TABLE 19

| | Copper Alloy | | Maximum Corrosion Depth (μm) | Mass loss (mg/cm²) Erosion Corrosion Test | | | Hot Forgeability | Wear resistance Wear loss (mg) | Cold Compression Workability | Semi-solid metal castability |
| | | | | I | II | III | | | | |
| | No. | Type | | | | | | | | |
|---|---|---|---|---|---|---|---|---|---|---|
| Embodiment | 1 | A | | | | | | | Δ | |
| | 2 | A | | | | | | | | Δ |
| | 3 | A | 10 or less | 28 | 42 | 148 | ○ | | ○ | ○ |
| | 4 | A | 10 or less | 27 | 43 | 149 | ○ | | ○ | ○ |
| | 5 | A | | | | | | | ○ | ○ |
| | 6 | A | | 2 | | | | 27 | | |
| | 7 | A | | | | | | | | |
| | 8 | A | 10 or less | 28 | 43 | 152 | | | Δ | |
| | 9 | A | | | | | | | | |
| | 10 | A | | | | | | | | Δ |
| | 11 | A | | ○ | | | ○ | | | ○ |
| | 12 | A | 10 or less | 25 | 41 | 149 | Δ | | | Δ |
| | 13 | A | 10 or less | | | | | | | Δ |
| | 14 | A | | | | | | | | |
| | 15 | A | | | | | | | | |

TABLE 19-continued

| Copper Alloy | | Maximum Corrosion | Mass loss (mg/cm²) Erosion Corrosion Test | | | Hot Forgeability | Wear resistance Wear loss (mg) | Cold Compression Workability | Semi-solid metal castability |
|---|---|---|---|---|---|---|---|---|---|
| No. | Type | Depth (μm) | I | II | III | | | | |
| 16 | A | | | | | | | | |
| 17 | A | | | | | | | | |
| 18 | A | | | | | | | | |
| 19 | A | | | | | | | | |
| 20 | A | | | | | | | | |
| 21 | A | | | | | | | | |
| 22 | A | | | | | | | | |
| 23 | A | | ○ | | | ○ | | ○ | |

TABLE 20

| | Copper Alloy | | Maximum Corrosion | Mass loss (mg/cm²) Erosion Corrosion Test | | | Hot Forgeability | Wear resistance Wear loss (mg) | Cold Compression Workability |
|---|---|---|---|---|---|---|---|---|---|
| | No. | Type | Depth (μm) | I | II | III | | | |
| Embodiment | 24 | A | 10 or less | 26 | 44 | 152 | ○ | 28 | ○ |
| | 25 | A | | Δ | | | Δ | | |
| | 26 | A | | | | | | | |
| | 27 | A | | | | | | | |
| | 28 | A | | Δ | | | Δ | | |
| | 29 | A | | | | | | | |
| | 30 | A | | | | | | | |
| | 31 | A | | | | | | | |
| | 32 | A | | | | | | | |
| | 33 | A | | | | | | | |
| | 34 | A | 10 or less | 20 | 35 | 126 | ○ | | |
| | 35 | A | | 119 | 34 | 124 | ○ | | |
| | 36 | A | 10 or less | 27 | 41 | 139 | | | |
| | 37 | A | 10 or less | 16 | 33 | 121 | | | |
| | 38 | A | | | | | | 1.4 | |
| | 39 | A | | | | | | 2.5 | |
| | 40 | A | | 1 | | | | 11 | |
| | 41 | A | 10 or less | | | | | | |
| | 42 | A | | | | | | | |
| | 43 | A | 10 or less | 19 | 35 | 124 | ○ | | |
| | 44 | A | 10 or less | 21 | 27 | 134 | | | |
| | 45 | A | | 1 | | | | 16 | |
| | 46 | A | 30 | 23 | 37 | 141 | | 1.8 | |

TABLE 21

| | Copper Alloy | | Pb leakage amount | Maximum Corrosion Depth | Mass loss (mg/cm²) Erosion Corrosion Test | | | Stress Corrosion | Cold | Cold Compression | Castability | |
|---|---|---|---|---|---|---|---|---|---|---|---|---|
| | No. | Type | (mg/L) | (μm) | I | II | III | Crackability | Drawability | Workability | Casting B | Casting C |
| Embodiment | 47 | B | | 10 or less | | | | ○ | ○ | ○ | ○ | B |
| | 48 | B | | | | | | ○ | ○ | ○ | ○ | B |
| | 49 | B | | | | | | ○ | Δ | Δ | Δ | B |
| | 50 | B | | | | | | ○ | ○ | ○ | ○ | B |
| | 51 | B | | | | | | ○ | ○ | ○ | ○ | B |
| | 52 | B | | | | | | ○ | ○ | ○ | ○ | B |
| | 53 | C | | | | | | | | | | ○ |
| | 54 | C | | 10 or less | 28 | 42 | 147 | | | | | ○ |
| | 55 | C | | 10 or less | 27 | 42 | 146 | | | | | ○ |
| | 56 | C | | | | | | | | | | ○ |
| | 57 | C | | | | | | | | | | Δ |
| | 58 | C | | 10 or less | 25 | 40 | 149 | | | | | Δ |

TABLE 21-continued

| Copper Alloy | | Pb leakage amount | Maximum Corrosion Depth | Mass loss (mg/cm²) Erosion Corrosion Test | | | Stress Corrosion | Cold | Cold Compression | Castability | |
|---|---|---|---|---|---|---|---|---|---|---|---|
| No. | Type | (mg/L) | (μm) | I | II | III | Crackability | Drawability | Workability | Casting B | Casting C |
| 59 | C | 0.001 or less | 10 or less | 28 | 43 | 148 | | | | | ○ |
| 60 | C | | | | | | | | | | ○ |
| 61 | C | | | | | | | | | | ○ |
| 62 | C | 0.001 or less | | | | | | | | | ○ |
| 63 | C | 0.001 or less | | | | | | | | | ○ |
| 64 | C | 0.002 | | | | | | | | | ○ |
| 65 | C | 0.006 | | | | | | | | | ○ |
| 66 | C | 0.009 | 10 or less | 27 | 52 | 150 | | | | | ○ |
| 67 | C | 0.014 | | | | | | | | | ○ |
| 68 | C | 0.001 or less | | | | | | | | | ○ |
| 69 | C | 0.009 | | | | | | | | | Δ |
| 70 | C | | 10 or less | 21 | 34 | 124 | | | | | ○ |

TABLE 22

| | Copper Alloy | | Maximum Corrosion Depth (μm) | Mass loss (mg/cm²) Erosion Corrosion Test | | | Hot Forgeability | Wear Resistance Wear loss (mg) | Castability | |
|---|---|---|---|---|---|---|---|---|---|---|
| | No. | Type | | I | II | III | | | Casting B | Casting C |
| Embodiment | 71 | C | | 119 | 34 | 125 | | | | ○ |
| | 72 | C | | | | | | | | |
| | 73 | C | | | | | | | | |
| | 74 | D | 10 or less | 28 | 43 | 150 | | | | |
| | 75 | D | 10 or less | 28 | 45 | 149 | | | | |
| | 76 | D | 10 or less | 24 | 43 | 153 | | | | |
| | 77 | D | 10 or less | 22 | 37 | 126 | | | | |
| | 78 | D | | 220 | 34 | 126 | | | | |
| | 79 | E | | | | | | | | |
| | 80 | E | 10 or less | 26 | 43 | 150 | ○ | | | |
| | 81 | E | | | | | | | | |
| | 82 | E | | 224 | 38 | 132 | | | | |
| | 83 | E | 10 or less | | | | | | | |
| | 84 | E | 10 or less | | | | | | | |
| | 85 | E | | ○ | | | ○ | 18 | | |
| | 86 | E | | | | | | 1.5 | | |
| | 87 | E | | 1 | | | | 12 | | |
| | 88 | E | | | | | | 2.3 | | |
| | 89 | E | | | | | | 2.2 | | |
| | 90 | E | | | | | | 2.4 | | |
| | 91 | F | | | | | | | | |
| | 92 | G | | | | | | | | |

TABLE 23

| | Copper Alloy | | Pb leakage amount (mg/L) | Maximum Corrosion Depth (μm) | Mass loss (mg/cm²) Erosion Corrosion Test | | | Stress Corrosion Crackability | Hot Forgeability | Wear resistance Wear loss (mg) | Cold Drawability | Cold Compression Workability | Forgeability | | Semi-solid metal castability |
|---|---|---|---|---|---|---|---|---|---|---|---|---|---|---|---|
| | No. | Type | | | I | II | III | | | | | | Casting B1 | Casting C1 | |
| Comparative | 201 | A1 | | | | | | | | | | | | | X |
| | 202 | A1 | | | | | | Δ | | | Δ | Δ | | | X |
| | 203 | A1 | | | | | | | | | | Δ | | | X |

TABLE 23-continued

| | Copper Alloy No. | Type | Pb leakage amount (mg/L) | Maximum Corrosion Depth (μm) | Mass loss (mg/cm²) Erosion Corrosion Test I | II | III | Stress Corrosion Crackability | Hot Forgeability | Wear resistance Wear loss (mg) | Cold Drawability | Cold Compression Workability | Forgeability Casting B1 | Casting C1 | Semi-solid metal castability |
|---|---|---|---|---|---|---|---|---|---|---|---|---|---|---|---|
| Example | 204 | A1 | | 180 | 36 | 52 | 178 | | | | | | | | |
| | 205 | A1 | | 10 or less | 26 | 44 | 143 | | Δ | 280 | | | | | |
| | 206 | A1 | | | | | | | | | | | | | |
| | 207 | A1 | | | | | | | | | | | | | |
| | 208 | A1 | | 250 | | | | | | | | | | | |
| | 209 | A1 | | | | | | | Δ | | | | | | |
| | 210 | A1 | | 300 | 45 | 63 | 256 | | | | | | | | |
| | 211 | A1 | | | | | | | | | | | | | |
| | 212 | A1 | | | | | | | | | | | | | |
| | 213 | A1 | | 250 | 42 | 57 | 215 | | | 320 | | | | | X |
| | 214 | A1 | | 400 | 48 | 71 | 303 | | | | | | | | |
| | 215 | A1 | | 10 or less | 18 | 33 | 118 | | | | | | | | |
| | 216 | A1 | | 10 or less | 18 | 34 | 120 | | | | | | | | |
| | 217 | B1 | | | | | | | | | ○ | Δ | X | | |
| | 218 | B1 | | | | | | Δ | X | | X | X | Δ | | |
| | 219 | C1 | | | | | | | | | | | | X | X |
| | 220 | C1 | | | | | | | | | | | | X | |
| | 221 | C1 | 0.031 | | | | | | | | | | | ○ | |
| | 222 | C1 | 0.003 | | | | | | | | | | | Δ | |
| | 223 | C1 | | | | | | | | | | | | X | |

TABLE 24

| | Copper Alloy No. | Type | Pb leakage amount (mg/L) | Maximum Corrosion Depth (μm) | Mass loss (mg/cm²) Erosion Corrosion Test I | II | III | Hot forgeability | Wear resistance Wear loss (mg) | Semi-solid metal castability |
|---|---|---|---|---|---|---|---|---|---|---|
| Comparative Example | 224 | C1 | | | | | | | | |
| | 225 | D1 | | | | | | | | |
| | 226 | D1 | 0.34 | | | | | | | |
| | 227 | E1 | | | | | | | | X |
| | 228 | E1 | | | | | | | | |
| | 229 | E1 | | | | | | | | X |
| | 230 | E1 | | | | | | | | X |
| | 231 | E1 | | 60 | 31 | 47 | 162 | Δ | | |
| | 232 | E1 | | | | | | | | |
| | 233 | E1 | | | | | | | | |
| | 234 | F1 | | | | | | | | |
| | 235 | G1 | | 800 | 64 | 118 | 423 | X | 600 | |
| | 236 | G1 | | 1000 | 67 | 116 | 445 | ○ | 520 | |

INDUSTRIAL APPLICABILITY

In particular, the copper alloy of the present invention can be properly used for the following applications.

1. General mechanical parts that require castability, conductivity, thermal conductivity and high mechanical property.

2. Electric terminals that require high conductivity and thermal conductivity, connectors, and electric parts on which brazing and welding can be easily performed.

3. Instrument parts that require excellent castability.

4. Water supply fittings, construction fittings and daily necessities which require excellent mechanical property.

5. Marine propellers, shafts, bearings, valve seats, valve rods, fasting fittings, clamps, connecting fittings, door knobs, pipe clamps and cams which require high strength and hardness and excellent corrosion resistance and toughness.

6. Valves, stems, bushes, worm gears, arms, cylinder parts, valve seats, bearings for stainless steel shafts and pump impellers which require high strength, hardness and wear resistance.

7. Valves, pump bodies, impellers, hydrants, mixed faucets, tap water valves, joints, sprinkler, cocks, tap water meter, water stop faucets, sensor parts, scroll type compressor parts, high-pressure valves and sleeve pressure containers which require pressure resistance, wear resistance, machinability and castability.

8. Sliding parts, hydraulic cylinders, cylinders, gears, fishing reels and aircraft clamps which require excellent hardness and wear resistance.

9. Bolts, nuts and piping connectors which require excellent strength, corrosion resistance and wear resistance.

10. Chemical mechanical parts and industrial valves which are suitable for a simple shaped large-size casting and require high strength and excellent corrosion resistance and wear resistance.

11. Welding pipes of a desalination apparatus, water supply pipes, heat exchanger pipes, heat exchanger pipe plates, gas piping tubes, elbows, marine structural members, welding members and welding materials which require bonding strength, build-up spraying, lining, overlay, corrosion resistance and castability.

12. Water-contact fittings (joint flanges)

nipples, hose nipples, sockets, elbows, cheeses, plugs, bushings, unions, joints, and flanges.

13. Water-contact fittings (valve cocks)

stop valves, a strainers, slith valves, gate valves, check valves, glove values, diaphragm valves, pinch valves, ball valves, needle valves, miniature valves, relief valves, plug cocks, handle cocks, gland cocks, two-way cocks, three-way cocks, four-way cocks, gas cocks, ball valves, safety valves, relief valves, pressure reducing valves, electromagnetic valves, steam traps, water meters (tap water meters), and flowmeters.

14. Water-contact fittings (water faucet fittings)

water faucets (hydrants, water sprinkling faucets, water stop faucets, swing cocks, mixed faucets and corporation faucets), spouts, branch faucets, check valves, branch valves, flash valves, switch cocks, showers, shower hooks, plugs, zarubos, watering nozzles, sprinklers.

15. Water-contact fittings (residential facility (residential equipment facility) drain mechanisms)

traps, fireplug valves, and water supply ports

16. Pumps impellers, cases, connecting fittings and slide bushes

17. Automobile related equipment valve and joints; pressure switch sensors, temperature sensors and connectors; bearing parts; compressor parts; carburetor parts; and cable fixtures.

18. Home appliances mobile phone antenna parts, terminal connectors, lead screws, motor bearings (fluid bearings), copier shaft rollers, valve seam nuts for air conditioners, and sensor parts.

19. Frictional engagement members piston shoes of hydraulic Pneumatic cylinders, bush sliding parts, cable fixtures, high-pressure valve joints, toothed wheel gear shafts, bearing parts, pump bearings, valve shoes, hexagon cap nuts, and header hydrate parts.

What is claimed is:

1. A casted copper alloy,
consisting essentially of Cu: 69 to 88 mass %, Si: 2 to 5 mass %, Zr: 0.0005 to 0.04 mass %, P: 0.01 to 0.25 mass %, and Zn: the balance;
having relation of, in terms of a content of an element a, [a] mass %, $f0=[Cu]-3.5[Si]-3[P]=61$ to 71, $f1=[P]/[Zr]=0.7$ to 200, $f2=[Si]/[Zr]=75$ to 5000, and $f3=[Si]/[P]=12$ to 240;
wherein the copper alloy has a metal structure that contains α phase and one or more additional phases selected from the group consisting of (i) K phase, (ii) γ phase, (iii) K phase and γ phase, (iv) β phase, and (v) μ phase, and having relation of, in terms of a content of a phase b, [b]%, in an area rate, $f4=[\alpha]+[\gamma]+[K]\geq 85$ and $f5=[\gamma]+[K]+0.3[\mu]-[\beta]=5$ to 95; and
the copper alloy has an average grain diameter of 200 μm or less in a macrostructure obtained when melted and solidified during casting.

2. The copper alloy as claimed in claim 1,
additionally containing at least one component selected from Pb: 0.005 to 0.45 mass %, Bi: 0.005 to 0.45 mass %, Se: 0.03 to 0.45 mass %, and Te: 0.01 to 0.45 mass %;
having relation of, in terms of the content of the element a, [a] mass %, $f0=[Cu]-3.5[Si]-3[P]+0.5([Pb]+0.8([Bi]+[Se])+0.6[Te])=61$ to 71, $f1=[P]/[Zr]=0.7$ to 200, $f2=[Si]/[Zr]=75$ to 5000, $f3=[Si]/[P]=12$ to 240, $f6=[Cu]-3.5[Si]-3[P]+3([Pb]+0.8([Bi]+[Se])+0.6[Te])^{1/2}\geq 2\,62$, and $f7=[Cu]-3.5[Si]-3[P]-3([Pb]+0.8([Bi]+[Se])+0.6[Te])^{1/2}\leq 68.5$, wherein [a]=0 as to a non-contained element a;
wherein the metal structure contains α phase and one or more additional phases selected from the group consisting of (i) K phase, (ii) γ phase, (iii) K phase and γ phase, (iv) β phase, and (v) μ phase, and having relation of, in terms of the content of the phase b, [b]%, in an area rate, $f4=[\alpha]+[\gamma]+[K]\geq 85$ and $f5=[\gamma]+[K]+0.3[\mu]-[\beta]=5$ to 95, wherein [b]=0 as to a non-contained phase b; and
the copper alloy has an average grain diameter of 200 μm or less in the macrostructure obtained when melted and solidified during casting.

3. The copper alloy as claimed in claim 2,
additionally containing at least one component selected from Sn: 0.05 to 1.5 mass %, As: 0.02 to 0.25 mass % and Sb: 0.02 to 0.25 mass %;
having relation of, in terms of the content of the element a, [a] mass %, $f0=[Cu]-3.5[Si]-3[P]+0.5([Pb]+0.8([Bi]+[Se])+0.6[Te])-0.5([Sn]+[As]+[Sb])=61$ to 71, $f1=[P]/[Zr]=0.7$ to 200, $f2=[Si]/[Zr]=75$ to 5000, $f3=[Si]/[P]=12$ to 240, $f6=[Cu]-3.5[Si]-3[P]+3([Pb]+0.8([Bi]+[Se])+0.6[Te])^{1/2}\geq 62$, and $f7=[Cu]-3.5[Si]-3[P]-3([Pb]+0.8([Bi]+[Se])+0.6[Te])^{1/2}\leq 68.5$, wherein [a]=0 as to the non-contained element a;
wherein the metal structure contains α phase and one or more additional phases selected from the group consisting of (i) K phase, (ii) γ phase, (iii) K phase and γ phase, (iv) β phase, and (v) μ phase, and having relation of, in terms of the content of the phase b, [b]%, in an area rate, $f4=[\alpha]+[\gamma]+[K]\geq 85$ and $f5=[\gamma]+[K]+0.3[\mu]-[D]\,5$ to 95, wherein [b]=0 as to the non-contained phase b; and
the copper alloy has an average grain diameter of 200 μm or less in the macrostructure obtained when melted and solidified during casting.

4. The copper alloy as claimed in claim 3,
additionally containing at least one component selected from Al : 0.02 to 1.5 mass %, Mn: 0.2 to 4 mass %, and Mg : 0.001 to 0.2 mass %;
having relation of, in terms of the content of the element a, [a] mass %, $f0=[Cu]-3.5[Si]-3[P]+0.5([Pb]+0.8([Bi]+[Se])+0.6[Te])-0.5([Sn]+[As]+[Sb])-1.8[Al]+2[Mn]+[Mg]=61$ to 71, $f1=[P]/[Zr]=0.7$ to 200, $f2=[Si]/[Zr]=75$ to 5000, and $f3=[Si]/[P]=12$ to 240, wherein [a]=0 as to the non-contained element a;
wherein the metal structure contains a phase and one or more additional phases selected from the group consisting of (i) K phase, (ii) γ phase, (iii) K phase and γ phase, (iv) β phase, and (v) μ phase, and having relation of, in terms of the content of the phase b, [b]%, in an area rate, $f4=[\alpha]+[\gamma]+[K]\geq 85$ and $f5=[\gamma]+[K]+0.3[\mu]-[\beta]=5$ to 95, wherein [b]=0 as to the non-contained phase b; and
the copper alloy has an average grain diameter of 200 μm or less in the macrostructure obtained when the copper alloy is melted and solidified during casting.

5. The copper alloy as claimed in claim 4,
having relation of, between the content of the element a, [a] mass %, and the content of the phase b, [b]%, in an area rate, $f8=[\gamma]+[K]+0.3[\mu]-[\beta]+25([Pb]+0.8([Bi]+[Se])+0.6[Te])^{1/2} \geqq 10$, and $f9=[\gamma]+[K]+0.3[\mu]-[\beta]-25([Pb]+0.8([Bi]+[Se])+0.6[Te])^{1/2} \leqq 70$, wherein [a]=[b]=0 as to the non-contained element a and phase b.

6. The copper alloy as claimed in claim 3,
having relation of, between the content of the element a, [a] mass %, and the content of the phase b, [b]%, in an area rate, $f8=[\gamma]+[K]+0.3[\mu]-[\beta]+25([Pb]+0.8([Bi]+[Se])+0.6[Te])^{1/2} \geqq 10$, and $f9=[\gamma]+[K]+0.3[\mu]-[\beta]-25([Pb]+0.8([Bi]+[Se])+0.6[Te])^{1/2} \leqq 70$, wherein [a]=[b]=0 as to the non-contained element a and phase b.

7. The copper alloy as claimed in claim 6, having any one of a casting obtained in a casting process and a plastic worked material additionally performing plastic working on the casting at least once.

8. The copper alloy as claimed in claim 3,
wherein, when any one of Fe and Ni is contained as an inevitable impurity, a content of any one of Fe and Ni is less than 0.3 mass %; and when Fe and Ni are contained as an inevitable impurity, a total content of Fe and Ni is less than 0.35 mass %.

9. The copper alloy as claimed in claim 4,
wherein, when any one of Pb and Bi is contained, any one of Pb and Bi particles having a fine uniform size is uniformly distributed in a matrix.

10. The copper alloy as claimed in claim 3, having any one of a casting obtained in a casting process and a plastic worked material additionally performing plastic working on the casting at least once.

11. The copper alloy as claimed in claim 10,
wherein, when the plastic worked material is cut by a lathe using a bite of a rake angle of −6° and a nose radius of 0.4 mm under a condition of a cutting speed of 80 to 160 m/min, a cutting depth of 1.5 mm and a feed speed of 0.11 mm/rev, a generated cut chip is a cut worked material taking a small segment shape of a trapezoidal or triangular shape, and a tape or acicular shape having a length of 25 mm or less.

12. The copper alloy as claimed in claim 10,
wherein, the casting is a wire, a rod, or a hollow bar cast by horizontal continuous casting, upward casting or up-casting.

13. The copper alloy as claimed in claim 10,
wherein, the copper alloy forms a frictional engagement member performing relative movement in contact with water at all times or temporarily.

14. The copper alloy as claimed in claim 13,
wherein, the copper alloy forms a gear, a sliding bush, a cylinder, a piston shoe, a bearing, a bearing part, a bearing member, a shaft, a roller, a rotary joint part, a bolt, a nut, or a screw shaft.

15. The copper alloy as claimed in claim 10,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

16. The copper alloy as claimed in claim 2,
having relation of, between the content of the element a, [a] mass %, and the content of the phase b, [b]%, in an area rate, $f8=[\gamma]+[K]+0.3[\mu]-[\beta]+25([Pb]+0.8([Bi]+[Se])+0.6[Te])^{1/2} \geqq 10$, and $f9=[\gamma]+[K]+0.3[\mu]-[\beta]-25([Pb]+0.8([Bi]+[Se])+0.6[Te])^{1/2} \leqq 70$, wherein [a]=[b]=0 as to the non-contained element a and phase b.

17. The copper alloy as claimed in claim 16,
wherein, the α phase of a matrix is finely divided, and at least one of the K and γ phases are uniformly distributed in the matrix.

18. The copper alloy as claimed in claim 16, having any one of a casting obtained in a casting process and a plastic worked material additionally performing plastic working on the casting at least once.

19. The copper alloy as claimed in claim 2,
wherein, when any one of Pb and Bi is contained, any one of Pb and Bi particles having a fine uniform size is uniformly distributed in a matrix.

20. The copper alloy as claimed in claim 2,
additionally containing at least one component selected from Al : 0.02 to 1.5 mass %, Mn: 0.2 to 4 mass %, and Mg : 0.001 to 0.2 mass %;
having relation of, in terms of the content of the element a, [a] mass %, $f0=[Cu]-3.5[Si]-3[P]+0.5([Pb]+0.8([Bi]+[Se])+0.6[Te])-0.5([Sn]+[As]+[Sb])-1.8[Al]+2[Mn]+[Mg]=61$ to 71, $f1=[P]/[Zr]=0.7$ to 200, $f2=[Si]/[Zr]=75$ to 5000, and $f3=[Si]/[P]=12$ to 240, wherein [a]=0 as to the non-contained element a;
wherein the metal structure contains a phase and one or more additional phases selected from the group consisting of (i) K phase, (ii) γ phase, (iii) K phase and γ phase, (iv) β phase, and (v) μ phase, and having relation of, in terms of the content of the phase b, [b]%, in an area rate, $f4=[\alpha]+[\gamma]+[K] \geqq 85$ and $f5=[\gamma]+[K]+0.3[\mu]-[\beta]=5$ to 95, wherein [b]=0 as to the non-contained phase b; and
the copper alloy has an average grain diameter of 200 μm or less in the macrostructure obtained when the copper alloy is melted and solidified during casting.

21. The copper alloy as claimed in claim 20,
having relation of, between the content of the element a, [a] mass %, and the content of the phase b, [b]%, in an area rate, $f8=[\gamma]+[K]+0.3[\mu]-[\beta]+25([Pb]+0.8([Bi]+[Se])+0.6[Te])^{1/2} \geqq 10$, and $f9=[\gamma]+[K]+0.3[\mu]-[\beta]-25([Pb]+0.8([Bi]+[Se])+0.6[Te])^{1/2} \leqq 70$, wherein [a]=[b]=0 as to the non-contained element a and phase b.

22. The copper alloy as claimed in claim 20, having any one of a casting obtained in a casting process and a plastic worked material additionally performing plastic working on the casting at least once.

23. The copper alloy as claimed in claim 22,
wherein, when the plastic worked material is cut by a lathe using a bite of a rake angle of −6° and a nose radius of 0.4 mm under a condition of a cutting speed of 80 to 160 m/min, a cutting depth of 1.5 mm and a feed speed of 0.11 mm/rev, a generated cut chip is a cut worked material taking a small segment shape of a trapezoidal or triangular shape, and a tape or acicular shape having a length of 25 mm or less.

24. The copper alloy as claimed in claim 22,
wherein, the copper alloy forms a frictional engagement member performing relative movement in contact with water at all times or temporarily.

25. The copper alloy as claimed in claim 24,
wherein, the copper alloy forms a gear, a sliding bush, a cylinder, a piston shoe, a bearing, a bearing part, a bearing member, a shaft, a roller, a rotary joint part, a bolt, a nut, or a screw shaft.

26. The copper alloy as claimed in claim 22,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

27. The copper alloy as claimed in claim 22,
wherein, the casting is a wire, a rod, or a hollow bar cast by horizontal continuous casting, upward casting or up-casting.

28. The copper alloy as claimed in claim 2,
wherein, when any one of Fe and Ni is contained as an inevitable impurity, a content of any one of Fe and Ni is less than 0.3 mass %; and when Fe and Ni are contained as an inevitable impurity, a total content of Fe and Ni is less than 0.35 mass %.

29. The copper alloy as claimed in claim 2,
wherein, the α phase of a matrix is finely divided, and at least one of the K and γ phases are umiformly distributed in the matrix.

30. The copper alloy as claimed in claim 2, having any one of a casting obtained in a casting process and a plastic worked material additionally performing plastic working on the casting at least once.

31. The copper alloy as claimed in claim 30,
wherein, when the plastic worked material is cut by a lathe using a bite of a rake angle of −6° and a nose radius of 0.4 mm under a condition of a cutting speed of 80 to 160 m/min, a cutting depth of 1.5 mm and a feed speed of 0.11 mm/rev, a generated cut chip is a cut worked material taking a small segment shape of a trapezoidal or triangular shape, and a tape or acicular shape having a length of 25 mm or less.

32. The copper alloy as claimed in claim 30,
wherein, the casting is a wire, a rod, or a hollow bar cast by horizontal continuous casting, upward casting or up-casting.

33. The copper alloy as claimed in claim 32,
wherein, the copper alloy is a water-contact fitting used in contact with water at all times or temporarily.

34. The copper alloy as claimed in claim 33, wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

35. The copper alloy as claimed in claim 32, wherein, the copper alloy forms a frictional engagement member performing relative movement in contact with water at all times or temporarily.

36. The copper alloy as claimed in claim 30,
wherein, the plastic worked material is a hot extruded material, a hot forged material or a hot rolled material.

37. The copper alloy as claimed in claim 30, wherein, the plastic worked material is a wire, a rod, or a hollow bar formed by stretching or cold drawing the casting, wherein the casting is a wire, a rod, or a hollow bar cast by horizontal continuous casting, upward casting or up-casting.

38. The copper alloy as claimed in claim 30,
wherein, the casting is a casting, a semi-melted casting, a semi-melted formed material, a molten metal forged material or a die cast formed material where at least a dendrite network has a divided crystalline structure in a semi-melted state of a solid phase fraction of 30 to 80% and the two dimensional grain shape of the solid phase has any one of a circular shape, a non-circular shape near to the circular shape, an elliptical shape, a criss-cross shape, an acicular shape and a polygonal shape.

39. The copper alloy as claimed in claim 38,
wherein, in the solid phase fraction of 60%, an average grain diameter of the solid phase is less than 150 μpm, or an average maximum length of the corresponding solid phase is less than 200 μm, or the average grain diameter of the solid phase is less than 150 μm and an average maximum length of the corresponding solid phase is less than 200 μm.

40. The copper alloy as claimed in claim 39,
wherein, the copper alloy is cast to a near net shape.

41. The copper alloy as claimed in claim 40,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

42. The copper alloy as claimed in claim 38,
wherein, the copper alloy is cast to a near net shape.

43. The copper alloy as claimed in claim 42,
wherein, the copper alloy is a water-contact fitting used in contact with water at all times or temporarily.

44. The copper alloy as claimed in claim 43,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

45. The copper alloy as claimed in claim 42,
wherein, the copper alloy forms a frictional engagement member performing relative movement in contact with water at all times or temporarily.

46. The copper alloy as claimed in claim 38,
wherein, the copper alloy is a water-contact fitting used in contact with water at all times or temporarily.

47. The copper alloy as claimed in claim 46,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

48. The copper alloy as claimed in claim 38,
wherein, the copper alloy forms a frictional engagement member performing relative movement in contact with water at all times or temporarily.

49. The copper alloy as claimed in claim 38,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

50. The copper alloy as claimed in claim 30,
wherein, the copper alloy is a water-contact fitting used in contact with water at all times or temporarily.

51. The copper alloy as claimed in claim 50,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

52. The copper alloy as claimed in claim 30,
wherein, the copper alloy forms a frictional engagement member performing relative movement in contact with water at all times or temporarily.

53. The copper alloy as claimed in claim 52,
wherein, the copper alloy forms a gear, a sliding bush, a cylinder, a piston shoe, a bearing, a bearing part, a bearing member, a shaft, a roller, a rotary joint part, a bolt, a nut, or a screw shaft.

54. The copper alloy as claimed in claim 30,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

55. The copper alloy as claimed in claim 1,
additionally containing at least one component selected from Sn: 0.05 to 1.5 mass %, As: 0.02 to 0.25 mass % and Sb: 0.02 to 0.25 mass %;
having relation of, in terms of the content of the element a, [a] mass %, $f0=[Cu]-3.5[Si]-3[P]-0.5([Sn]+[As]+[Sb])=61$ to 71, $f1=[P]/[Zr]=0.7$ to 200, $f2=[Si]/[Zr]=75$ to 5000, and $f3=[Si]/[P]=12$ to 240, wherein [a]=0 as to a non-contained element a;
wherein the metal structure contains α phase and one or more additional phases selected from the group consisting of (i) K phase, (ii) γ phase, (iii) K phase and γ phase, (iv) β phase, and (v) μ phase, and having relation of, in terms of the content of the phase b, [b]%, in an area rate, $f4=[\alpha]+[\gamma]+[K]\geqq 85$ and $f5=[\gamma]+[K]+0.3[\mu]-[\beta]=5$ to 95, wherein [b]=0 as to a non-contained phase b; and
the copper alloy has an average grain diameter of 200 μm or less in the macrostructure obtained when melted and solidified during casting.

56. The copper alloy as claimed in claim 55,
additionally containing at least one component selected from Al : 0.02 to 1.5 mass%, Mn: 0.2 to 4 mass %, and Mg : 0.001 to 0.2 mass %;
having relation of, in terms of the content of the element a, [a] mass%, $f0=[Cu]-3.5[Si]-3[P]+0.5([Pb]+0.8([Bi]+[Se])+0.6[Te])-0.5([Sn]+[As]+[Sb])-1.8[Al]+2[Mn]+[Mg]=61$ to 71, $f1=[P]/[Zr]=0.7$ to 200, $f2=[Si]/[Zr]=75$ to 5000, and $f3=[Si]/[P]=12$ to 240, wherein [a]=0 as to the non-contained element a;
wherein the metal structure contains a phase and one or more additional phases selected from the group consisting of (i) K phase, (ii) γphase, (iii) K phase and γ phase, (iv) β phase, and (v) μ phase, and having relation of, in terms of the content of the phase b, [b]%, in an area rate, $f4=[\alpha]+[\gamma]+[K]\geqq 85$ and $f5'[\gamma]+[K]+0.3[\mu]-[\beta]=5$ to 95, wherein [b]=0 as to the non-contained phase b; and
the copper alloy has an average grain diameter of 200 μm or less in the macrostructure obtained when the copper alloy is melted and solidified during casting.

57. The copper alloy as claimed in claim 55,
wherein, when any one of Fe and Ni is contained as an inevitable impurity, a content of any one of Fe and Ni is less than 0.3 mass %; and when Fe and Ni are contained as an inevitable impurity, a total content of Fe and Ni is less than 0.35 mass %.

58. The copper alloy as claimed in claim 57, having any one of a casting obtained in a casting process and a plastic worked material additionally performing plastic working on the casting at least once.

59. The copper alloy as claimed in claim 55,
wherein, when melted and solidified during casting, a primary crystal is the α phase.

60. The copper alloy as claimed in claim 55,
wherein, when melted and solidified during casting, a peritectic reaction is generated.

61. The copper alloy as claimed in claim 55,
wherein, when melted and solidified, the copper alloy comprises a dendrite network having a divided crystalline structure, and further comprises a two-dimensional grain shape selected from the group consisting of a circular shape, a non-circular shape near to the circular shape, an elliptical shape, a criss-cross shape, an acicular shape and a polygonal shape.

62. The copper alloy as claimed in claim 55,
wherein, the α phase of a matrix is finely divided, and at least one of the K and γ phases are uniformly distributed in the matrix.

63. A method of producing a copper alloy as claimed in claim 55, wherein, in a casting process, Zr is added in a form of a copper alloy material containing Zr, and Zr is prevented from being added in a form of an oxide, or a sulfide, or an oxide and a sulfide, when casting.

64. The method as claimed in claim 63,
wherein, the copper alloy material containing Zr is a copper alloy that additionally contains at least one component selected from P, Mg, Al, Sn, Mn and B based on a Cu-Zr alloy and a Cu-Zn-Zr alloy.

65. The copper alloy as claimed in claim 1,
additionally containing at least one component selected from Al: 0.02 to 1.5 mass %, Mn: 0.2 to 4 mass %, and Mg: 0.001 to 0.2 mass %;
having relation of, in terms of the content of the element a, [a] mass %, f0=[Cu]−3.5[Si]−3[P]+0.5([Pb]+0.8([Bi]+[Se])+0.6[Te])−0.5([Sn]+[As]+[Sb])−1.8[Al]+2[Mn]+[Mg]=61 to 71, f1=[P]/[Zr]=0.7 to 200, f2=[Si]/[Zr]=75 to 5000, and f3=[Si]/[P]=12 to 240, wherein [a]=0 as to the non-contained element a;
wherein the metal structure contains α phase and one or more additional phases selected from the group consisting of (i) K phase, (ii) γ phase, (iii) K phase and γ phase, (iv) β phase, and (v) μ phase, and having relation of, in terms of the content of the phase b, [b]%, in an area rate, f4=[α]+[γ]+[K]≧85 and f5=[γ]+[K]+0.3[μ]−[β]=5 to 95, wherein [b]=0 as to the non-contained phase b; and
the copper alloy has an average grain diameter of 200 μm or less in the macrostructure obtained when the copper alloy is melted and solidified during casting.

66. The copper alloy as claimed in claim 65,
wherein, when any one of Fe and Ni is contained as an inevitable impurity, a content of any one of Fe and Ni is less than 0.3 mass %; and when Fe and Ni are contained as an inevitable impurity, a total content of Fe and Ni is less than 0.35 mass %.

67. The copper alloy as claimed in claim 65,
wherein, when melted and solidified during casting, a primary crystal is the α phase.

68. The copper alloy as claimed in claim 65,
wherein, when melted and solidified during casting, a peritectic reaction is generated.

69. The copper alloy as claimed in claim 65,
wherein, the α phase of a matrix is finely divided, and at least one of the K and γ phases are uniformly distributed in the matrix.

70. The copper alloy as claimed in claim 55, having any one of a casting obtained in a casting process and a plastic worked material additionally performing plastic working on the casting at least once.

71. The copper alloy as claimed in claim 70,
wherein, when the plastic worked material is cut by a lathe using a bite of a rake angle of −6° and a nose radius of 0.4 mm under a condition of a cutting speed of 80 to 160 m/min, a cutting depth of 1.5 mm and a feed speed of 0.11 mm/rev, a generated cut chip is a cut worked material taking a small segment shape of a trapezoidal or triangular shape, and a tape or acicular shape having a length of 25 mm or less.

72. The copper alloy as claimed in claim 71,
wherein, the casting is a wire, a rod, or a hollow bar cast by horizontal continuous casting, upward casting or up-casting.

73. The copper alloy as claimed in claim 72,
wherein, the copper alloy is a water-contact fitting used in contact with water at all times or temporarily.

74. The copper alloy as claimed in claim 73,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

75. The copper alloy as claimed in claim 72,
wherein, the copper alloy forms a frictional engagement member performing relative movement in contact with water at all times or temporarily.

76. The copper alloy as claimed in claim 70,
wherein, the plastic worked material is a hot extruded material, a hot forged material or a hot rolled material.

77. The copper alloy as claimed in claim 70, wherein, the plastic worked material is a wire, a rod, or a hollow bar formed by stretching or cold drawing the casting, wherein the casting is a wire, a rod, or a hollow bar cast by horizontal continuous casting, upward casting or up-casting.

78. The copper alloy as claimed in claim 70,
wherein, the casting is a casting, a semi-melted casting, a semi-melted formed material, a molten metal forged material or a die cast formed material where at least a dendrite network has a divided crystalline structure in a semi-melted state of a solid phase fraction of 30 to 80% and the two dimensional grain shape of the solid phase has any one of a circular shape, a non-circular shape near to the circular shape, an elliptical shape, a criss-cross shape, an acicular shape and a polygonal shape.

79. The copper alloy as claimed in claim 78,
wherein, in the solid phase fraction of 60%, an average grain diameter of the solid phase is less than 150 μm, or an average maximum length of the corresponding solid phase is less than 200 μm, or the average grain diameter of the solid phase is less than 150 μm and an average maximum length of the corresponding solid phase is less than 200 μm.

80. The copper alloy as claimed in claim 79,
wherein, the copper alloy is cast to a near net shape.

81. The copper alloy as claimed in claim 80,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

82. The copper alloy as claimed in claim 78,
wherein, the copper alloy is cast to a near net shape.

83. The copper alloy as claimed in claim 82,
wherein, the copper alloy is a water-contact fitting used in contact with water at all times or temporarily.

84. The copper alloy as claimed in claim 83,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

85. The copper alloy as claimed in claim 82,
wherein, the copper alloy forms a frictional engagement member performing relative movement in contact with water at all times or temporarily.

86. The copper alloy as claimed in claim 78,
wherein, the copper alloy is a water-contact fitting used in contact with water at all times or temporarily.

87. The copper alloy as claimed in claim 86,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

88. The copper alloy as claimed in claim 78,
wherein, the copper alloy forms a frictional engagement member performing relative movement in contact with water at all times or temporarily.

89. The copper alloy as claimed in claim 78,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

90. The copper alloy as claimed in claim 70,
wherein, the copper alloy is a water-contact fitting used in contact with water at all times or temporarily.

91. The copper alloy as claimed in claim 90,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

92. The copper alloy as claimed in claim 70,
wherein, the copper alloy forms a frictional engagement member performing relative movement in contact with water at all times or temporarily.

93. The copper alloy as claimed in claim 92,
wherein, the copper alloy forms a gear, a sliding bush, a cylinder, a piston shoe, a bearing, a bearing part, a bearing member, a shaft, a roller, a rotary joint part, a bolt, a nut, or a screw shaft.

94. The copper alloy as claimed in claim 70,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

95. The copper alloy as claimed in claim 65, having any one of a casting obtained in a casting process and a plastic worked material additionally performing plastic working on the casting at least once.

96. The copper alloy as claimed in claim 95,
wherein, when the plastic worked material is cut by a lathe using a bite of a rake angle of −6° and a nose radius of 0.4 mm under a condition of a cutting speed of 80 to 160 m/min, a cutting depth of 1.5 mm and a feed speed of 0.11 mm/rev, a generated cut chip is a cut worked material taking a small segment shape of a trapezoidal or triangular shape, and a tape or acicular shape having a length of 25 mm or less.

97. The copper alloy as claimed in claim 95,
wherein, the casting is a wire, a rod, or a hollow bar cast by horizontal continuous casting, upward casting or up-casting.

98. The copper alloy as claimed in claim 95,
wherein, the copper alloy forms a frictional engagement member performing relative movement in contact with water at all times or temporarily.

99. The copper alloy as claimed in claim 98,
wherein, the copper alloy forms a gear, a sliding bush, a cylinder, a piston shoe, a bearing, a bearing part, a bearing member, a shaft, a roller, a rotary joint part, a bolt, a nut, or a screw shaft.

100. The copper alloy as claimed in claim 95,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

101. A method of producing a copper alloy as claimed in claim 65, wherein, in a casting process, Zr is added in a form of a copper alloy material containing Zr, and Zr is prevented from being added in a form of an oxide, or a sulfide, or an oxide and a sulfide, when casting.

102. The method as claimed in claim 101,
wherein, the copper alloy material containing Zr is a copper alloy that additionally contains at least one component selected from P, Mg, Al, Sn, Mn and B based on a Cu-Zr alloy and a Cu-Zn-Zr alloy.

103. The copper alloy as claimed in claim 1,
wherein, when any one of Fe and Ni is contained as an inevitable impurity, a content of any one of Fe and Ni is less than 0.3 mass %; and when Fe and Ni are contained as an inevitable impurity, a total content of Fe and Ni is less than 0.35 mass %.

104. The copper alloy as claimed in claim 103,
wherein, the α phase of a matrix is finely divided, and at least one of the K and γ phases are uniformly distributed in the matrix.

105. The copper alloy as claimed in claim 103, having any one of a casting obtained in a casting process and a plastic worked material additionally performing plastic working on the casting at least once.

106. A method of producing a copper alloy as claimed in claim 103, wherein, in a casting process, Zr is added in a form of a copper alloy material containing Zr, and Zr is prevented from being added in a form of an oxide, or a sulfide, or an oxide and a sulfide, when casting.

107. The method as claimed in claim 106,
wherein, the copper alloy material containing Zr is a copper alloy that additionally contains at least one component selected from P, Mg, Al, Sn, Mn and B based on a Cu-Zr alloy and a Cu-Zn-Zr alloy.

108. The copper alloy as claimed in claim 1,
wherein, when melted and solidified during casting, a primary crystal is the α phase.

109. The copper alloy as claimed in claim 1,
wherein, when melted and solidified, the copper alloy comprises a dendrite network having a divided crystalline structure, and further comprises a two-dimensional grain shape selected from the group consisting of a circular shape, a non-circular shape near to the circular shape, an elliptical shape, a criss-cross shape, an acicular shape and a polygonal shape.

110. The copper alloy as claimed in claim 1,
wherein, the α phase of a matrix is finely divided, and at least one of the K and γ phases are uniformly distributed in the matrix.

111. The copper alloy as claimed in claim 1, having any one of a casting obtained in a casting process and a plastic worked material additionally performing plastic working on the casting at least once.

112. The copper alloy as claimed in claim 111,
wherein, when the plastic worked material is cut by a lathe using a bite of a rake angle of −6° and a nose radius of 0.4 mm under a condition of a cutting speed of 80 to 160 m/min, a cutting depth of 1.5 mm and a feed speed of 0.11 mm/rev, a generated cut chip is a cut worked material taking a small segment shape of a trapezoidal or triangular shape, and a tape or acicular shape having a length of 25 mm or less.

113. The copper alloy as claimed in claim 111,
wherein, the casting is a wire, a rod, or a hollow bar cast by horizontal continuous casting, upward casting or up-casting.

114. The copper alloy as claimed in claim 113,
wherein, the copper alloy is a water-contact fitting used in contact with water at all times or temporarily.

115. The copper alloy as claimed in claim 114, wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

116. The copper alloy as claimed in claim 113,
wherein, the copper alloy forms a frictional engagement member performing relative movement in contact with water at all times or temporarily.

117. The copper alloy as claimed in claim 111,
wherein, the plastic worked material is a hot extruded material, a hot forged material or a hot rolled material.

118. The copper alloy as claimed in claim 111, wherein, the plastic worked material is a wire, a rod, or a hollow bar formed by stretching or cold drawing the casting, wherein the casting is a wire, a rod, or a hollow bar cast by horizontal continuous casting, upward casting or up-casting.

119. The copper alloy as claimed in claim 111,
wherein, the casting is a casting, a semi-melted casting, a semi-melted formed material, a molten metal forged material or a die cast formed material where at least a dendrite network has a divided crystalline structure in a semi-melted state of a solid phase fraction of 30 to 80% and the two dimensional grain shape of the solid phase has any one of a circular shape, a non-circular shape near to the circular shape, an elliptical shape, a criss-cross shape, an acicular shape and a polygonal shape.

120. The copper alloy as claimed in claim 119,
wherein, in the solid phase fraction of 60%, an average grain diameter of the solid phase is less than 150 μm, or an average maximum length of the corresponding solid phase is less than 200 μm, or the average grain diameter of the solid phase is less than 150 μm and an average maximum length of the corresponding solid phase is less than 200 μm.

121. The copper alloy as claimed in claim 120,
wherein, the copper alloy is cast to a near net shape.

122. The copper alloy as claimed in claim 121,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

123. The copper alloy as claimed in claim 119,
wherein, the copper alloy is cast to a near net shape.

124. The copper alloy as claimed in claim 123,
wherein, the copper alloy is a water-contact fitting used in contact with water at all times or temporarily.

125. The copper alloy as claimed in claim 124,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

126. The copper alloy as claimed in claim 123,
wherein, the copper alloy forms a frictional engagement member performing relative movement in contact with water at all times or temporarily.

127. The copper alloy as claimed in claim 119,
wherein, the copper alloy is a water-contact fitting used in contact with water at all times or temporarily.

128. The copper alloy as claimed in claim 127,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

129. The copper alloy as claimed in claim 119,
wherein, the copper alloy forms a frictional engagement member performing relative movement in contact with water at all times or temporarily.

130. The copper alloy as claimed in claim 119,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

131. The copper alloy as claimed in claim 111,
wherein, the copper alloy is a water-contact fitting used in contact with water at all times or temporarily.

132. The copper alloy as claimed in claim 131,
wherein the copper alloy forms a nipple, a hose nipple, a socket, an elbow, a cheese, a plug, a bushing, a union, a joint, a flange, a stop valve, a strainer, a slith valve, a gate valve, a check valve, a glove value, a diaphragm valve, a pinch valve, a ball valve, a needle valve, a miniature valve, a relief valve, a plug cock, a handle cock, a gland cock, a two-way cock, a three-way cock, a four-way cock, a gas cock, a ball valve, a safety valve, a relief valve, a pressure reducing valve, an electromagnetic valve, a steam trap, a tap water meter, a flowmeter, a hydrant, a water sprinkling faucet, a water stop faucet, a swing cock, a mixed faucet, a corporation faucet, a spout, a branch faucet, a check valve, a branch valve, a flash valve, a switch cock, a shower, a shower hook, a plug, a zarubo, a watering nozzle, a sprinkler, a heating pipe for a water heater, a heating pipe for a heat exchanger, a heating pipe for a boiler, a trap, a fireplug valve, a water supply port, an impeller, an impeller shaft or a pump case.

133. The copper alloy as claimed in claim 111,
wherein, the copper alloy forms a frictional engagement member performing relative movement in contact with water at all times or temporarily.

134. The copper alloy as claimed in claim 133,
wherein, the copper alloy forms a gear, a sliding bush, a cylinder, a piston shoe, a bearing, a bearing part, a bearing member, a shaft, a roller, a rotary joint part, a bolt, a nut, or a screw shaft.

135. The copper alloy as claimed in claim 111,
wherein, the copper alloy forms a pressure sensor, a temperature sensor, a connector, a compressor part, a scroll compressor part, a high pressure valve, a valve open-close value for an air conditioner, a carburetor part, a cable fixture, a mobile phone antenna part, or a terminal.

136. A method of producing a copper alloy as claimed in claim 1,
wherein, in a casting process, Zr is added in a form of a copper alloy material containing Zr, and Zr is prevented from being added in a form of an oxide, or a sulfide, or an oxide and a sulfide, when casting.

137. The method as claimed in claim 136,
wherein, the copper alloy material containing Zr is a copper alloy that additionally contains at least one component selected from P, Mg, Al, Sn, Mn and B based on a Cu-Zr alloy and a Cu-Zn-Zr alloy.

138. A casted copper alloy,
consisting essentially of Cu: 69 to 88 mass %, Si: 2 to 5 mass %, Zr: 0.0005 to 0.04 mass %, P: 0.01 to 0.25 mass %, and Zn: the balance;
having relation of, in terms of a content of an element a, [a] mass %, f0=[Cu]−3.5[Si]−3[P]=61 to 71, f1=[P]/[Zr]=0.7 to 200, f2=[Si]/[Zr]=75 to 5000, and f3=[Si]/[P]=12 to 240;
wherein the copper alloy has a metal structure that contains α phase and one or more additional phases selected from the group consisting of (i) K phase, (ii) γ phase, (iii) K phase and γ phase, (iv) β phase, and (v) μ phase, and having relation of, in terms of a content of a phase b, [b]%, in an area rate, f4=[α]+[γ]30 [K]≧85 and f5=[γ]+[K]+0.3[μ]−[β]=5 to 95; and
the copper alloy has an average grain diameter of 200 μm or less in a macrostructure obtained when melted and solidified during casting, wherein, when melted and solidified during casting, a peritectic reaction is generated.

139. The copper alloy as claimed in claim 138, having any one of a casting obtained in a casting process and a plastic worked material additionally performing plastic working on the casting at least once.

140. A casted copper alloy,
consisting essentially of Cu: 69 to 88 mass %, Si: 2 to 5 mass %, Zr: 0.0005 to 0.04 mass %, P: 0.01 to 0.25 mass%, and Zn: the balance;
having relation of, in terms of a content of an element a, [a] mass %, f0=[Cu]−3.5[Si]−3[P]=61 to 71, f1=[P]/[Zr]=0.7 to 200, f2=[Si]/[Zr]=75 to 5000, and f3=[Si]/[P]=12 to 240;
wherein the copper alloy has a metal structure that contains a phase and one or more additional phases selected from the group consisting of (i) K phase, (ii) γ phase, (iii) K phase and γ phase, (iv) β phase, and (v) μ phase, and having relation of, in terms of a content of a phase b, [b]%, in an area rate, f4=[α]+[γ]+[K] ≧85 and f5=[γ]+[K]+0.3[μ]−[β]=5 to 95; and
the copper alloy has an average grain diameter of 200 μm or less in a macrostructure obtained when melted and solidified during casting, wherein the copper alloy is provided when a cooling rate in the melt-solidification of casting has a range from $10^{-2}$ to $10^{4\circ}$ C/sec, when casting starts at 20 to 250° C. higher than a liquidus temperature of the copper alloy or below 1150° C., and when Zr is added in a form of Cu-Zr alloy or Cu-Zn-Zr alloy, before casting.

* * * * *